United States Patent
Donega et al.

(10) Patent No.: US 11,724,102 B2
(45) Date of Patent: *Aug. 15, 2023

(54) TREATMENT OF ACUTE MEDICAL CONDITIONS

(71) Applicant: Galvani Bioelectronics Limited, Middlesex (GB)

(72) Inventors: Matteo Donega, Middlesex (GB); Daniel John Chew, Middlesex (GB); Margarita J. Vervoordeldonk, Maarssen (NL); Isha Gupta, Middlesex (GB)

(73) Assignee: Galvani Bioelectronics Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,829

(22) Filed: Jul. 25, 2022

(65) Prior Publication Data
US 2022/0409890 A1    Dec. 29, 2022

Related U.S. Application Data

(63) Continuation of application No. 16/955,331, filed as application No. PCT/GB2018/053730 on Dec. 20, 2018, now Pat. No. 11,452,867.
(Continued)

(51) Int. Cl.
*A61N 1/00* (2006.01)
*A61N 1/05* (2006.01)
(Continued)

(52) U.S. Cl.
CPC ......... *A61N 1/0556* (2013.01); *A61N 1/0553* (2013.01); *A61N 1/36053* (2013.01);
(Continued)

(58) Field of Classification Search
None
See application file for complete search history.

(56) References Cited

U.S. PATENT DOCUMENTS 6,442,431 B1 * 8/2002 Veraart ............... A61N 1/0543
  607/54
8,831,739 B2 * 9/2014 McCreery ............... A61N 1/05
  607/116
(Continued)

FOREIGN PATENT DOCUMENTS

EP    1 897 586 A1    3/2008
WO   2012 083259 A2   6/2012
(Continued)

OTHER PUBLICATIONS

Douglas B. McCreery et al., "Charge Density and Charge Per Phase as Cofactors in Neural Injury Induced by Electrical Stimulation," in IEEE Transactions on Biomedical Engineering, vol. 37, No. 10, pp. 996-1001, Oct. 1990, DOI: 10.1109/10.102812.
(Continued)

*Primary Examiner* — John R Downey
*Assistant Examiner* — Anant A Gupta
(74) *Attorney, Agent, or Firm* — Banner & Witcoff, Ltd.

(57) ABSTRACT

Electrical stimulation of neural activity in the neural innervation of the spleen that is associated with neurovascular bundles provides a useful way to treat acute medical conditions, such as trauma, hemorrhaging and shock.

16 Claims, 45 Drawing Sheets

Related U.S. Application Data

(60) Provisional application No. 62/608,420, filed on Dec. 20, 2017.

(51) Int. Cl.
*A61N 1/36* (2006.01)
*A61N 1/378* (2006.01)

(52) U.S. Cl.
CPC ..... *A61N 1/36057* (2013.01); *A61N 1/36071* (2013.01); *A61N 1/36114* (2013.01); *A61N 1/36135* (2013.01); *A61N 1/36171* (2013.01); *A61N 1/3787* (2013.01)

(56) References Cited

U.S. PATENT DOCUMENTS

| | | | |
|---|---|---|---|
| 10,363,420 B2* | 7/2019 | Fried | A61B 5/4836 |
| 11,446,496 B2* | 9/2022 | Vervoordeldonk | A61N 1/0556 |
| 11,452,867 B2* | 9/2022 | Donega | A61N 1/0556 |
| 2004/0236382 A1 | 11/2004 | Dinsmoor et al. | |
| 2005/0075701 A1* | 4/2005 | Shafer | A61N 1/36017 607/72 |
| 2005/0075702 A1* | 4/2005 | Shafer | A61N 1/36071 607/72 |
| 2006/0217707 A1 | 9/2006 | Daniel et al. | |
| 2009/0054955 A1 | 2/2009 | Kopell et al. | |
| 2009/0118780 A1 | 5/2009 | DiLorenzo | |
| 2010/0125304 A1 | 5/2010 | Faltys | |
| 2011/0106208 A1 | 5/2011 | Faltys et al. | |
| 2011/0190849 A1 | 8/2011 | Faltys et al. | |
| 2011/0313488 A1 | 12/2011 | Hincapie Ordonez et al. | |
| 2013/0085537 A1 | 4/2013 | Mashiach | |
| 2014/0288551 A1 | 9/2014 | Bharmi et al. | |
| 2015/0174397 A1 | 6/2015 | Bhadra et al. | |
| 2015/0258341 A1 | 9/2015 | Ternes et al. | |
| 2016/0015978 A1 | 1/2016 | Cakmak | |
| 2016/0015988 A1 | 1/2016 | Perryman et al. | |
| 2016/0067497 A1 | 3/2016 | Levine et al. | |
| 2017/0095679 A1 | 4/2017 | Sobotka et al. | |
| 2017/0113046 A1 | 4/2017 | Fried et al. | |
| 2017/0165480 A1* | 6/2017 | O'Mahony | A61M 16/024 |
| 2018/0161577 A1 | 6/2018 | Goedeke et al. | |
| 2019/0290913 A1 | 9/2019 | Blancou et al. | |

FOREIGN PATENT DOCUMENTS

| | | |
|---|---|---|
| WO | 2013086461 A1 | 6/2013 |
| WO | 2014 153223 A1 | 9/2014 |
| WO | 2014 197625 A1 | 12/2014 |
| WO | 2016 170510 A1 | 10/2016 |

OTHER PUBLICATIONS

Modin A. et al., "Repeated Renal and Splenic Sympathetic Nerve Stimulation in Anaesthetized Pigs: Maintained Overflow of Neuropeptide Y in Controls but not After Reserpine," Journal of the Autonomic Nervous Systems, Elsevier, Amsterdamn, NL, vol. 49, No. 2, Oct. 1, 1994, pp. 123-134, XP024325768, ISSN: 0165-1838, DOI: 10.1016/0165-1838(94)90132-5.

Modin A. et al., "Comparison of the Acute Influence of Neuropeptide Y and Sympathetic Stimulation on the Composition of Blood Cells in the Splenic Vein in Vivo," Regulatory Peptides, Elsevier Science BV, NL, vol. 47, No. 2, Sep. 3, 1993, pp. 159-169,XP025209233, ISSN: 0167-0115, DOI: 10.1016/0167-0115(93)90420-D.

William M. Reichert, "Indwelling Neural Implants: Strategies for Contending with the In Vivo Environment," Frontiers in Neuroengineering, Boca Raton (FL): CRC Press/Taylor & Francis <http://www.crcpress.com/>; 2008, ISBN-13: 978-0-8493-9362-4.

"Important Safety Instructions" for the St. Jude Medical Infinity™ DBS System—<https://www.neuromodulation.abbott/us/en/products/dbs-therapy-movement-disorders/st-jude-medical-infinity-dbs-system.html#isi <https://www.neuromodulation.abbott/us/en/products/dbs-therapymovement-disorders/st-jude-medical-infinity-dbssystem.html>, accessed Jan. 27, 2022.

Stuart F. Cogan et al., "Tissue damage thresholds during therapeutic electrical stimulation," Journal of Neural Engineering, Apr. 2016; 13(2): 021001. doi:10.1088/1741-2560/13/2/021001.

* cited by examiner

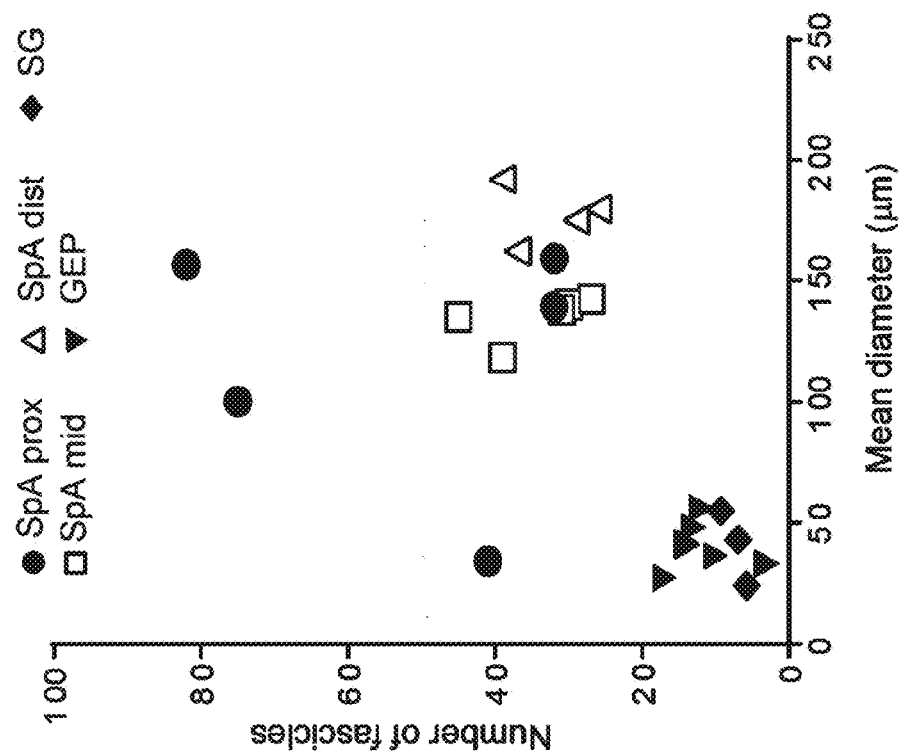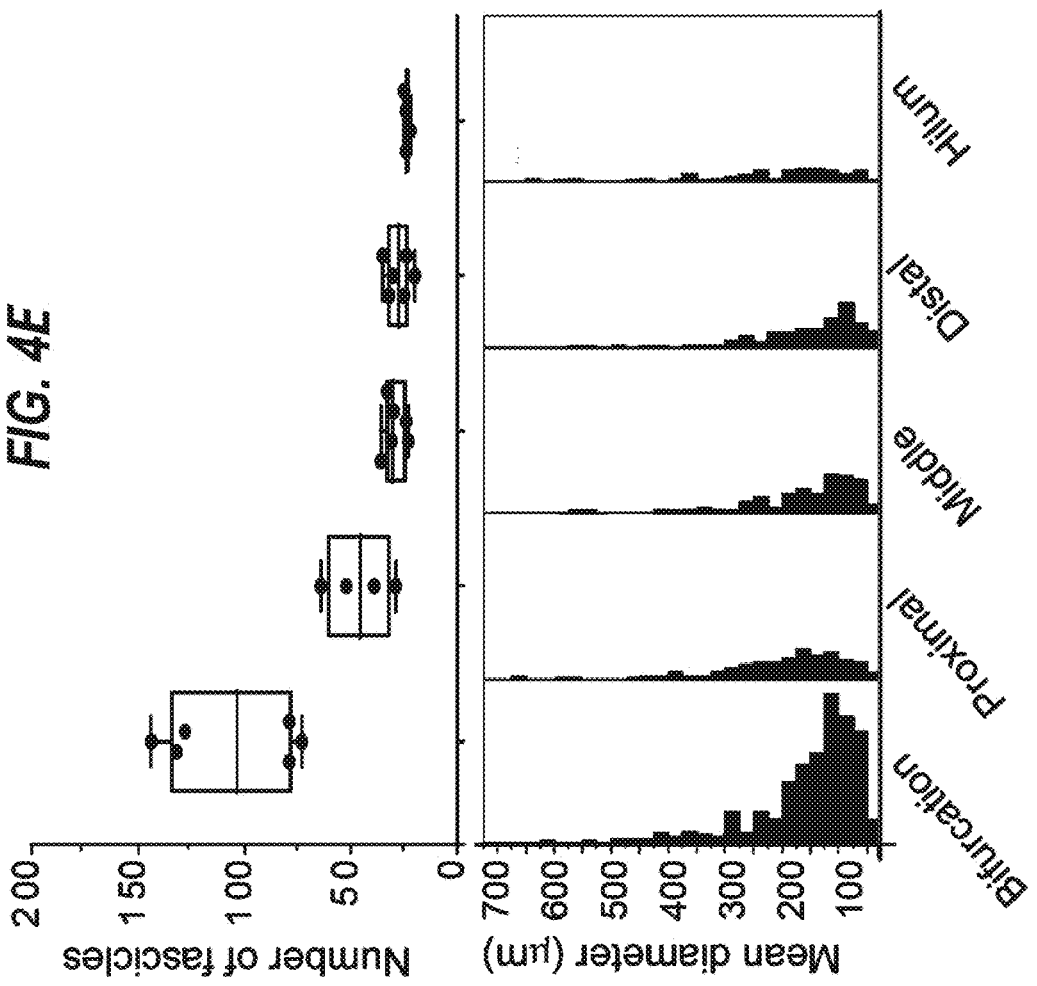

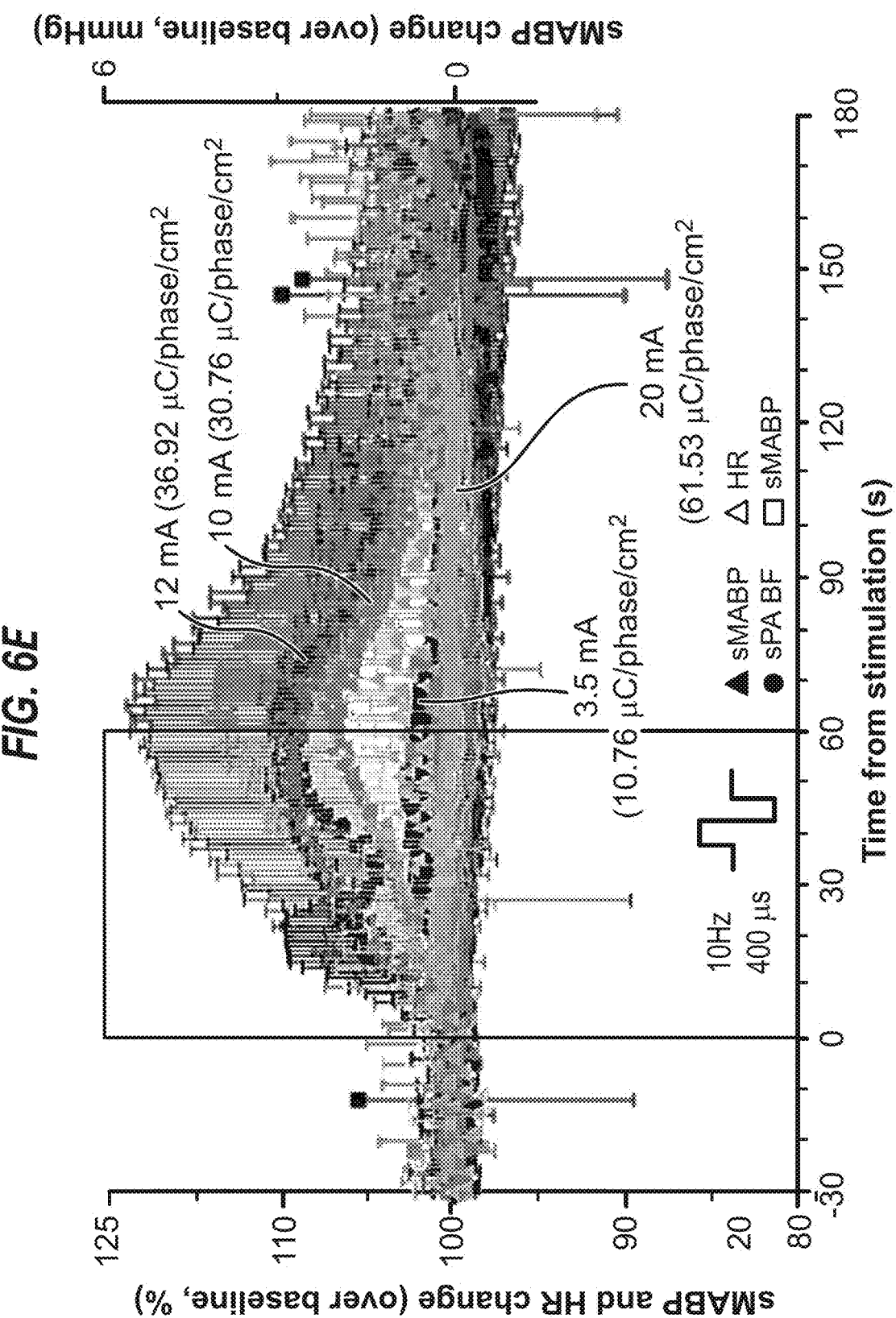

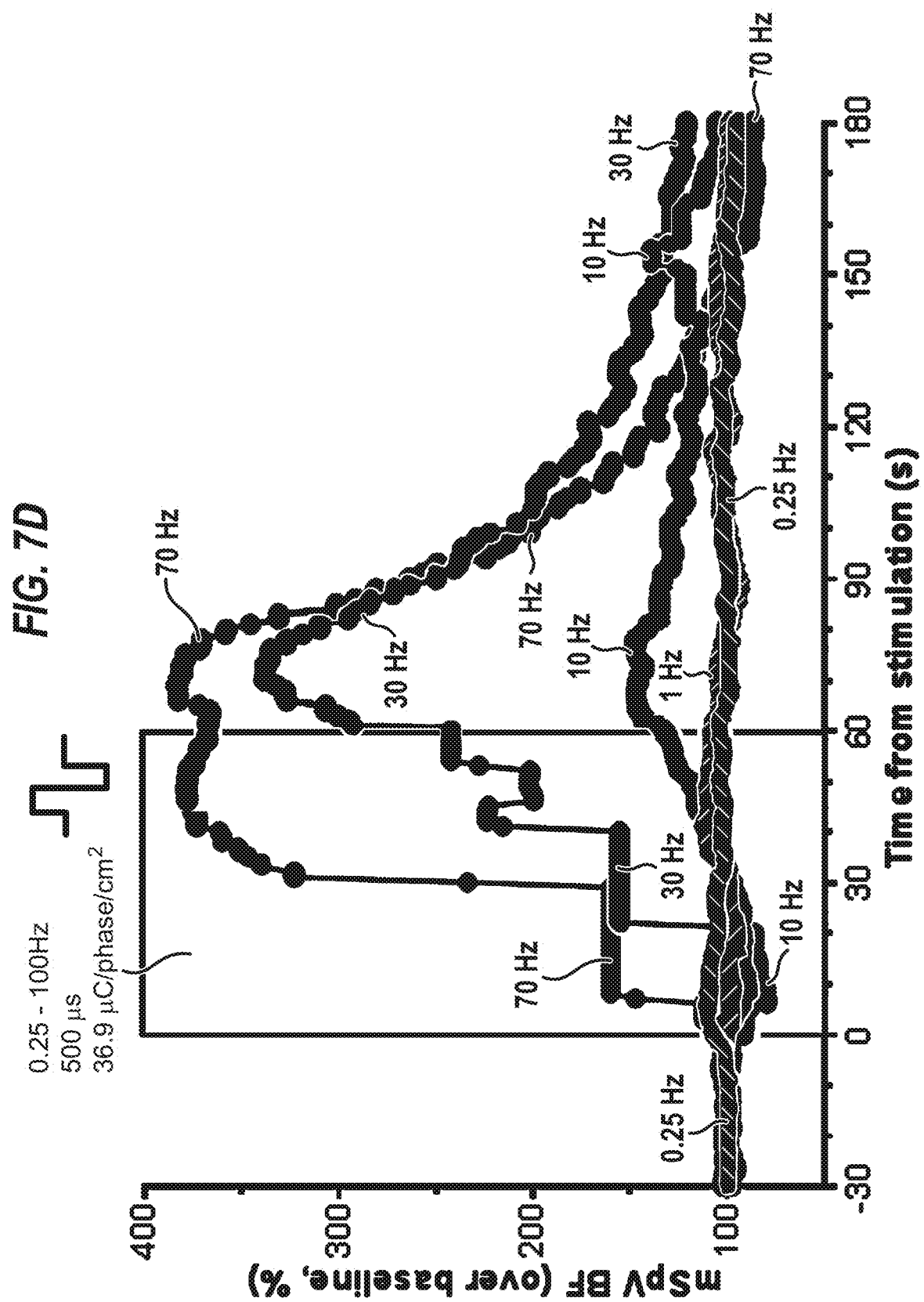

Cadaver III

Cadaver III

Cadaver III

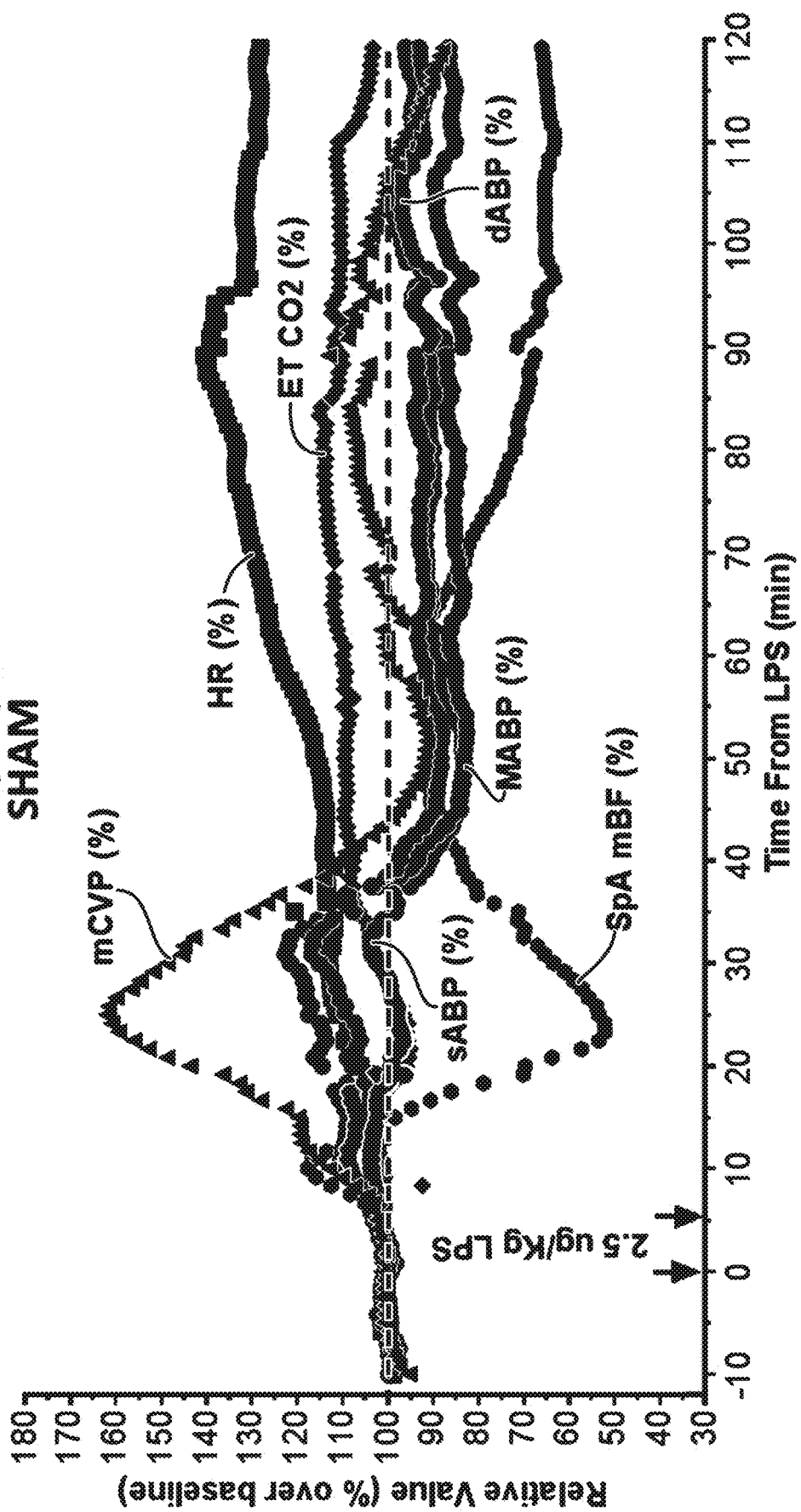

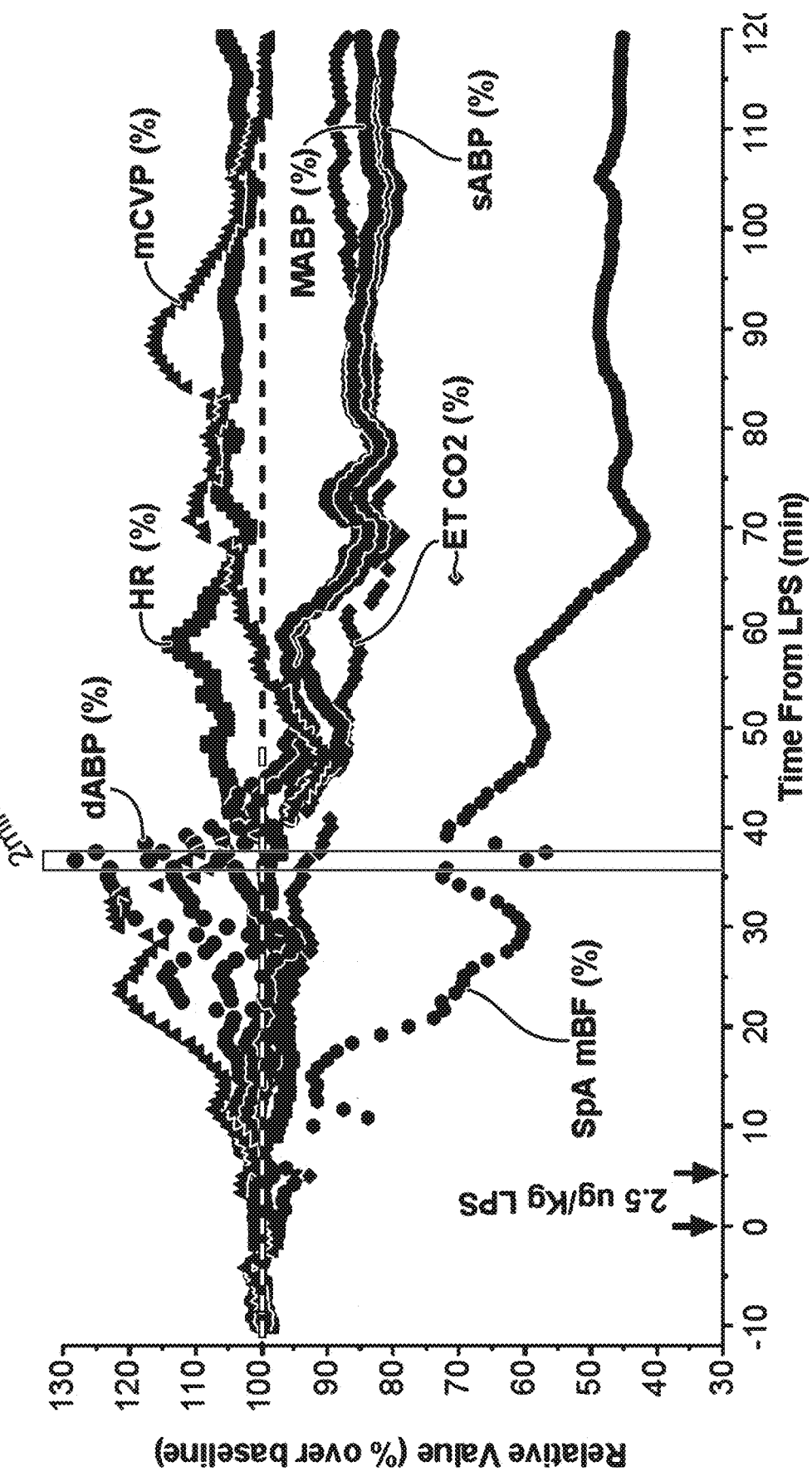

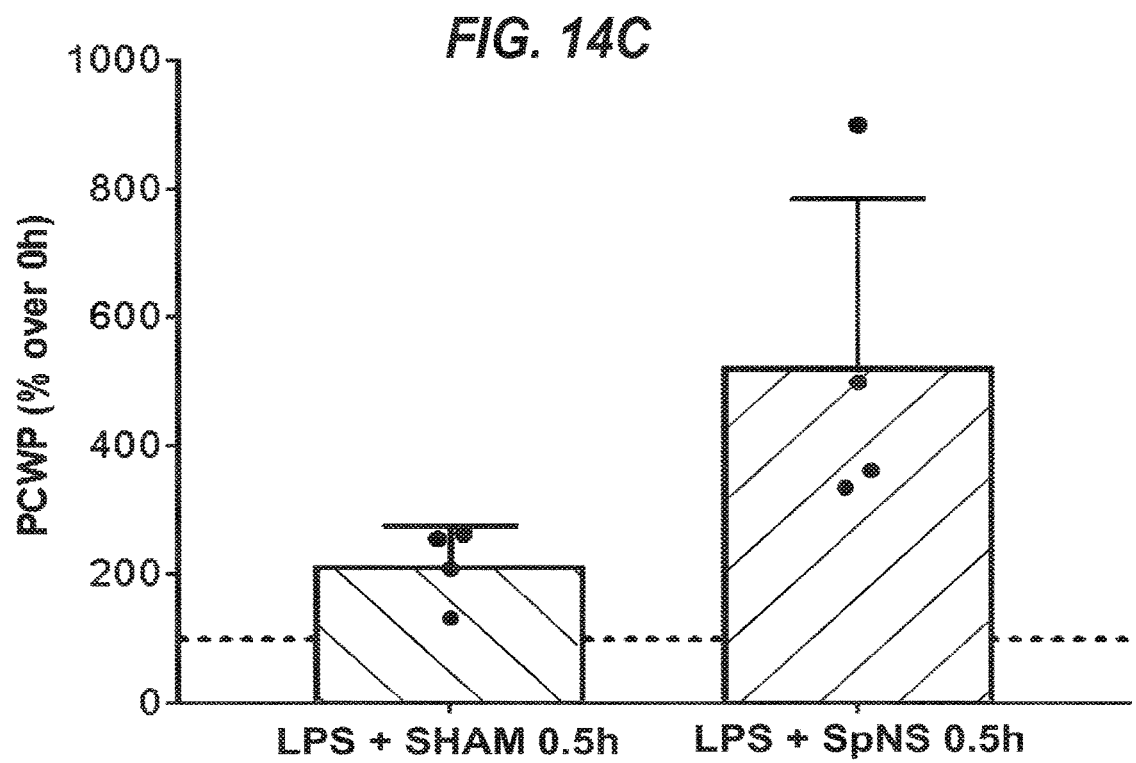
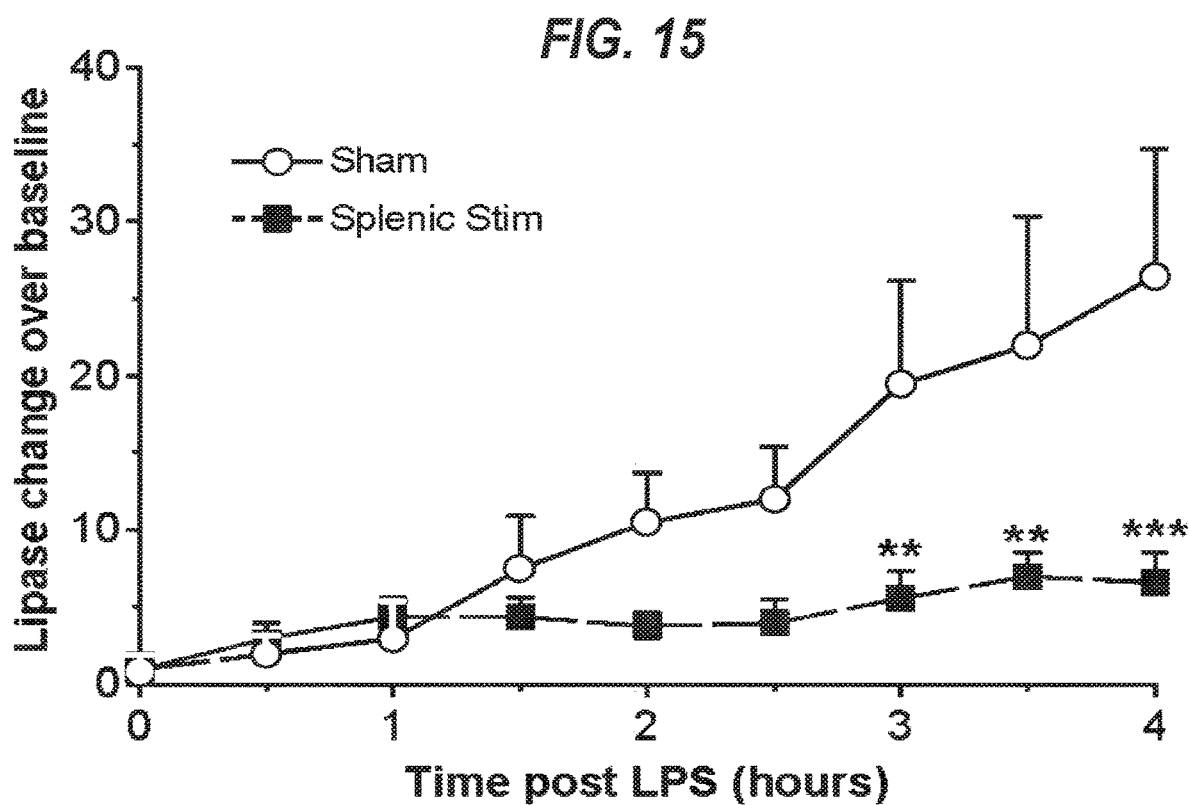

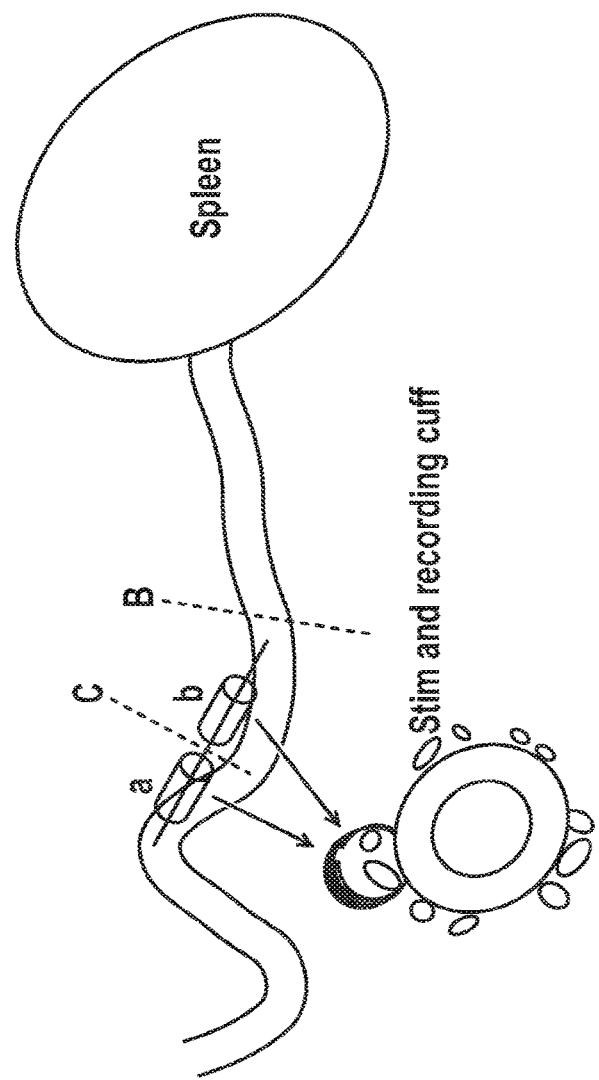
FIG. 16A

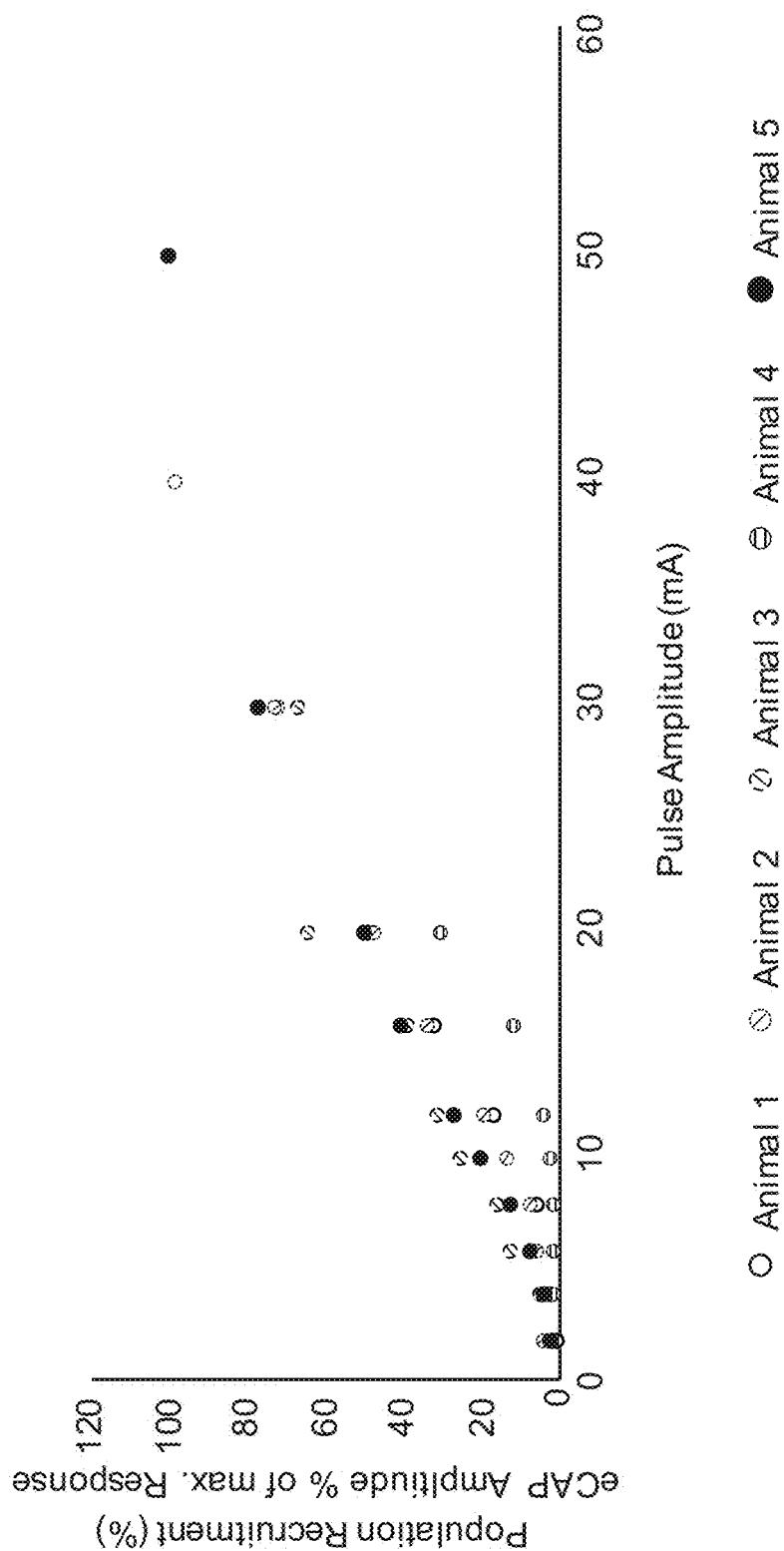

Acute Stimulation on splenic neurovascular bundle
Strength - duration curve

*in-silico* data from porcine models

*in-silico* data from porcine models

*in-silico* data from human models

*in-silico* data from human models

TREATMENT OF ACUTE MEDICAL CONDITIONS

CROSS-REFERENCE TO RELATED APPLICATION

This application is a continuation of U.S. patent application Ser. No. 16/955,331 filed Jun. 18, 2020, which is a U.S. National Stage application under 35 U.S.C. § 371 of International Application PCT/GB2018/053730 (published as WO 2019/122907) filed Dec. 20, 2018, which claims the benefit of priority to U.S. provisional Application No. 62/608,420 filed Dec. 20, 2017. Each of these prior applications are hereby incorporated by reference in their entirety.

TECHNICAL FIELD

This invention relates to treatment of acute medical conditions. More specifically, the invention relates to devices, systems and methods for the treatment of acute medical conditions.

BACKGROUND ART

Acute medical conditions, as referred to herein, refer to rapid deterioration in a subject's physiological status that may be life threatening if left untreated. Examples include trauma, sepsis, haemorrhage, severe hemophilia, severe episodes of lupus, episodes of severe Crohn's, allograph/autograph rejection, anaphylaxis, and endotoxic shock. These subjects therefore require urgent medical care to relieve suffering and minimize morbidity and mortality risk. Treatments of acute medical conditions vary according to the disease, and depending on the severity of the condition, often these treatments are not successful.

In contrast, chronic medical conditions are those characterized by prolonged clinical course during which there is little change or slow progression of underlying pathology. For example, arthritis (e.g. rheumatoid arthritis), chronic pancreatitis, chronic obstructive pulmonary disease, or chronic heart failure. However, subjects with chronic conditions may suffer from acute exacerbations of the underlying disease process, and this is generally referred to as acute-on-chronic episodes. The distinction between acute and chronic medical conditions is well known in the art.

The spleen contains half of the body's monocyte population making this organ the main contributor in inflammation, in particular in response to endotoxemic shock [1]. The spleen is innervated by different nervous branches, and splenic innervation is proposed to be 98% sympathetic (reviewed in [2]). Electrical stimulation of the splenic nerves is associated with vascular responses of the spleen [3]. It has been suggested that electrical stimulation of the splenic nerves may be useful for treating conditions associated with chronic immune and inflammatory responses, e.g. see References [4,5,6,7]. However, the pro-survival effects of splenic nerve stimulation in acute medical conditions have not been investigated.

There is a need for identifying further and improved ways of treating acute medical conditions.

SUMMARY OF THE INVENTION

The inventors show for the first time that neuromodulation of the nerves supplying the spleen, in particular the nerves surrounding the splenic artery (referred to herein as splenic arterial nerves), increased survival of animals in an endotoxemic (LPS) shock model. In particular, the inventors found that electrical stimulation of the splenic nerves stabilized blood pressure, which drops dramatically in LPS-treated animals, and reduced the maximum reduction in blood pressure. Hence, stimulation of the neural activity of splenic nerves provides a way for treating acute medical conditions, in particular life-threatening conditions, such as those having physiological changes associated with shock, and cardiovascular dysfunction (e.g. trauma, hemorrhaging and septic shock). This would be particularly useful as a single treatment, e.g. in acute clinical settings.

Thus, the invention provides a method for treating an acute medical condition, such as trauma, hemorrhaging or septic shock, the method comprising applying an electrical signal to stimulate the neural activity of a nerve supplying the spleen, wherein the nerve is associated with a neurovascular bundle (e.g. a splenic arterial nerve), such that the electrical signal produces an improvement in a physiological parameter indicative of treatment of an acute medical condition, wherein the improvement in the physiological parameter is any of the group consisting of: restoring the body temperature to between 36 degrees Celsius (° C.) and 38° C., restoring the heart rate to 60-100 bpm, restoring the systemic arterial pressure to between 90/60 mmHg and 150/90 mmHg, restoring the systemic venous pressure to about 5 mmHg in the right atrium and about 8 mmHg in the left atrium, restoring the central venous pressure to in the range of about 3-8 mmHg, restoring the pulmonary pressure to about 15 mmHg, restoring the breathing rate to 8-14 breaths per minute, an increase in oxygen saturation to ≥94%, an increase the arterial partial pressure of oxygen to 12-15 kPa, restoring the arterial partial pressure of carbon dioxide to 4.4-6.1 kPa, a reduction of pain sensation, restoring urine output to ≥0.5 ml/kg/hr, increase the level of consciousness, a reduction in the level of lactate, a change in the level of blood glucose, a change in the level of base deficit in blood and a change in the level of arterial pH.

The invention also provides a method for treating an acute medical condition, such as trauma, hemorrhaging or septic shock, the method comprising applying an electrical signal to stimulate the neural activity of a nerve supplying the spleen, wherein the nerve is associated with a neurovascular bundle (e.g. a splenic arterial nerve), such that the electrical signal produces an improvement in a physiological parameter indicative of treatment of an acute medical condition, wherein the improvement in the physiological parameter is any of the group consisting of: restoring physiological values of systemic arterial blood pressure between 90/60 mmHg and 150/90 mmHg and restoring the systemic venous pressure in the range of 3-8 mmHg, restoring the pulmonary pressure to about 15 mmHg, restoring lower levels of pulmonary vascular resistance while increasing systemic vascular resistance and increasing pulmonary capillary wedge pressure, reducing high levels of lipases, reducing high levels of amylases.

The invention also provides a system for stimulating the neural activity of a nerve supplying the spleen, wherein the nerve is associated with a neurovascular bundle (e.g. a splenic arterial nerve), for treating an acute medical condition. The system comprises at least one electrode in signaling contact with the nerve, and at least one controller electrically coupled to the at least one electrode. The at least one controller configured to control the operation of the least one electrode to apply an electrical signal to the nerve. The electrical signal is configured such that it produces an improvement in a physiological parameter indicative of treatment of the acute medical condition. The improvement in the physiological parameter is any of the group consisting of: restoring the body temperature to between 36° C. and 38° C., restoring the heart rate to 60-100 bpm, restoring the systemic arterial pressure to between 90/60 mmHg and 150/90 mmHg, restoring the systemic venous pressure to about 5 mmHg in the right atrium and about 8 mmHg in the left atrium, restoring the central venous pressure to in the range of about 3-8 mmHg, restoring the pulmonary pressure to about 15 mmHg, restoring the breathing rate to 8-14 breaths per minute, an increase in oxygen saturation to ≥94%, an increase the arterial partial pressure of oxygen to 12-15 kPa, restoring the arterial partial pressure of carbon dioxide to 4.4-6.1 kPa, a reduction of pain sensation, restoring urine output to ≥0.5 ml/kg/hr, increase the level of consciousness, a reduction in the level of lactate, a change in the level of blood glucose, a change in the level of base deficit in blood and a change in the level of arterial pH.

The invention also provides a computer-implemented method for treating an acute medical condition in a subject. The method comprises controlling the operation of at least one electrode of the system of the invention to apply a signal to a nerve supplying the spleen, wherein the nerve is associated with a neurovascular bundle (e.g. a splenic arterial nerve), to stimulate neural activity, such that the neural activity of the nerve is reversibly stimulated.

The invention also provides a computer comprising a processor and a non-transitory computer readable storage medium carrying an executable computer program comprising code portions which, when loaded and run on the processor, cause the processor to: apply an electrical signal to stimulate the neural activity of a nerve supplying the spleen, wherein the nerve is associated with a neurovascular bundle (e.g. a splenic arterial nerve), such that the electrical signal produces an improvement in a physiological parameter indicative of treatment of an acute medical condition.

The invention also provides a neurostimulatory electrical signal for use in a method of treating an acute medical condition, wherein the electrical signal is any electrical signal described herein.

The invention also provides an electrical waveform for use in a method of treating an acute medical condition, wherein the electrical waveform causes reversible depolarization of the nerve membrane of a nerve supplying the spleen, wherein the nerve is associated with a neurovascular bundle (e.g. a splenic arterial nerve), such that an action potential is generated de novo in the nerve.

The invention also provides a charged particle for use in a method of treating an acute medical condition, wherein the charged particle causes reversible depolarization of the nerve membrane of a nerve supplying the spleen, wherein the nerve is associated with a neurovascular bundle (e.g. a splenic arterial nerve), such that an action potential is generated de novo in the modified nerve.

The invention also provides a modified nerve to which the neural interface of the system of the invention is in signaling contact, wherein the nerve supplies the spleen and is associated with a neurovascular bundle (e.g. a splenic arterial nerve), wherein the at least one electrode is in signaling contact with the nerve and so the nerve can be distinguished from the nerve in its natural state, and wherein the nerve is located in a subject having an acute medical condition.

The invention also provides a modified nerve obtainable by stimulating neural activity of a nerve supplying the spleen, wherein the nerve is associated with a neurovascular bundle, preferably a splenic arterial nerve, according to a method of the invention.

The invention also provides a method of controlling a system of the invention which is in signaling contact with a nerve supplying the spleen, wherein the nerve is associated with a neurovascular bundle (e.g. a splenic arterial nerve), comprising a step of sending control instructions to the system, in response to which the system applies a signal to the nerve.

DETAILED DESCRIPTION OF THE INVENTION

Nerves Supplying the Spleen

Innervation of the spleen is primarily sympathetic or noradrenergic, with peptide neurons likely representing the bulk of the remaining neurons. The human spleen is mainly innervated by the splenic plexus surrounding the splenic artery. The splenic artery is covered with nervous tissue, which is derived from the coeliac plexus and continues with the splenic artery to the spleen as the splenic plexus. The splenic plexus enters the spleen at the hilum where the splenic artery diverges in terminal branches and the splenic plexus continues with these branches into the parenchyma of the spleen.

The splenic plexus includes several nerve fascicles which circumvent the main splenic artery from celiac artery to spleen, each nerve fascicle comprising a small bundle of nerve fibers. A nerve fascicle (or known as a peri-arterial nerve fascicle) that circumvents the splenic nerve is referred to herein as a splenic arterial nerve.

The course of the splenic artery is variable. In general, it tends runs along the surface of the pancreas and is often in direct contact with the pancreas. Between the site of origin and the entry point at the hilum, the splenic artery can separate from the surface of the pancreas at certain positions, such that the splenic artery is not in direct contact with the pancreas.

The invention involves applying an electrical signal to, and thereby modulating the neural activity of, a nerve supplying the spleen, wherein the nerve is associated with a neurovascular bundle. Preferably, the nerve is a splenic arterial nerve.

In some embodiments, the nerve is a sympathetic nerve.

In some embodiments, the invention may involve applying an electrical signal to one splenic arterial nerve. In other embodiments, the invention may involve a plurality (i.e. a bundle) of splenic arterial nerves.

In other embodiments, the invention may involve applying an electrical signal to at least one splenic arterial nerve and the splenic artery. In other embodiments, the invention may involve applying an electrical signal to all splenic arterial nerves and the splenic artery.

In other embodiments, the invention may involve applying an electrical signal to at least one splenic arterial nerve, for instance the splenic plexus, associated with a part of the splenic artery that is separated from the surface of the pancreas. For example, the electrical signal may be applied to the at least one nerve at a site adjacent to a splenic arterial loop. Splenic arterial loops are characterized by being separated by a distance of, for example, ≥0.5 cm from the surface of the pancreas, where the intervening space is filled by adipose tissue and/or connective tissue. The application of an electrical signal to this site is advantageous since it allows the isolation of the nerve plexus associated with the splenic artery more straight forward. This application site is also expected to make surgery safer, from the perspective of reducing surgical injury to the pancreas.

In some embodiments, the splenic arterial loop is separated from the surface of the pancreas by a distance of ≥1 cm, e.g. about 1-2 cm, preferably about 1.5 cm, where this distance between the inner curvature on top of the loop, and the surface of the pancreas. This distance may be referred to as the height of the loop, as described herein.

A splenic arterial loop may have a neck of about ≥0.5 cm, where, in this context, "neck" refers to the direct distance between the inner curvature of the first leg of the loop (the position at which the splenic artery separates from the surface of the spleen) and the inner curvature of the second leg of the loop (the position at which the splenic artery comes back into direct contact with the spleen). In some embodiments, the neck is ≥0.55 cm, ≥0.6 cm, ≥0.65 cm, ≥0.7 cm, ≥0.75 cm, ≥0.8 cm, ≥0.85 cm, ≥0.9 cm, ≥0.95 cm, ≥1 cm, ≥1.1 cm, ≥1.2 cm, ≥1.3 cm, ≥1.4 cm, ≥1.5 cm, ≥1.6 cm, ≥1.7 cm, ≥1.8 cm, ≥1.9 cm, or ≥2.0 cm. In some embodiments, the splenic arterial loop may have a neck in the range of about 1.1 cm to about 3.0 cm.

The number of splenic arterial loops can vary between human subjects, but, in general, there appears to be a positive correlation between the number of splenic arterial loops and the age of a subject. Typically, splenic arterial loops are more frequently observed in human subjects over the age of 45.

In some embodiments, the signal application site may be at one or more nerves adjacent to one splenic arterial loop.

In some embodiments, the signal application sites may be at one or more nerves adjacent to a plurality of splenic arterial loops. In some embodiments, each of the plurality of independent sites may be stimulated with independent systems or methods of the invention. In some embodiments, each of the plurality of said sites may be stimulated by a single system, device of method of the invention.

In some embodiments, the signal may be applied to one or more nerves in each of the plurality splenic arterial loops, simultaneously, sequentially or separately.

Simultaneously may refer to the application of the signal at each of the plurality of sites at substantially the same time, i.e. within the error of possible delay, the signal is intended to be applied to each of the plurality of sites at exactly the same time. Separately may refer to the application of the signal to each of the plurality of sites independently of one another i.e. the signals are not to be applied in a concerted sequence. Each of the signals is transmitted to each of the sites independently. It is to be understood that the application of separate signals can result in each or several of the plurality of sites coincidentally receiving a signal at substantially the same time. Sequentially may refer to the application of the signal to each of the plurality of sites in a defined "sequence". This may involve the application of signals to several of the plurality of independent sites at substantially the same time.

Stimulation of a Nerve Supplying the Spleen

The invention involves applying an electrical signal to a nerve supplying the spleen, wherein the nerve is associated with a neurovascular bundle (e.g. a splenic arterial nerve), to stimulate neural activity in the nerve. Stimulation refers to where signaling activity in at least part of the nerve being increased compared to baseline neural activity in that part of the nerve, where baseline neural activity is the signaling activity of the nerve in the subject prior to any intervention. Put another way, stimulation results in the creation of neural activity which increases the total neural activity in that part of the nerve.

"Neural activity" of a nerve refers to the signaling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, areas under the curve and other patterns of action potentials in the nerve or sub-groups (e.g. fascicules) of neurons therein.

Stimulation typically involves increasing neural activity e.g. generating action potentials beyond the point of the stimulation in at least a part of the nerve. At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in its normal state, wherein action potentials propagate from point to adjacent point along the axon, and which can be observed using conventional experimentation.

One way of characterizing a stimulation of neural activity is a distribution of potassium and sodium ions at one or more points in the axon, which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization of the nerve membrane that would not otherwise occur. The depolarization of the nerve membrane caused by the temporary external electrical field generates de novo action potential across that point. This is a nerve operating in a disrupted state, which can be observed by a distribution of potassium and sodium ions at a point in the axon (the point which has been stimulated) that has an electrical membrane potential that is not influenced or determined by the electrical membrane potential of an adjacent point.

Stimulation of neural activity is thus understood to be increasing neural activity from continuing past the point of signal application. Thus, the nerve at the point of signal application is modified in that the nerve membrane is reversibly depolarized by an electric field, such that a de novo action potential is generated and propagates through the modified nerve. Hence, the nerve at the point of signal application is modified in that a de novo action potential is generated.

When the signal is an electrical signal, the stimulation is based on the influence of electrical currents (e.g. charged particles, which may be one or more electrons in an electrode in signaling contact with the nerve, or one or more ions outside the nerve or within the nerve, for instance) on the distribution of ions across the nerve membrane.

Stimulation of neural activity encompasses full stimulation of neural activity in the nerve—that is, embodiments where the total neural activity is increased in the whole nerve.

Stimulation of neural activity may be partial stimulation. Partial stimulation may be such that the total signaling activity of the whole nerve is partially increased, or that the total signaling activity of a subset of nerve fibers of the nerve is fully increased (i.e. there is no neural activity in that subset of fibers of the nerve), or that the total signaling of a subset of nerve fibers of the nerve is partially increased compared to baseline neural activity in that subset of fibers of the nerve. For example, an increase in neural activity of ≤5%, ≤10%, ≤15%, ≤20%, ≤25%, ≤30%, ≤35%, ≤40%, ≤45%, ≤50%, ≤60%, ≤70%, ≤80%, ≤90% or ≤95%, or an increase of neural activity in a subset of nerve fibers of the nerve. Neural activity may be measured by methods known in the art, for example, by the number of action potentials which propagate through the axon and/or the amplitude of the local field potential reflecting the summed activity of the action potentials.

One advantage of the invention is that stimulation of neural activity is reversible. Hence, the modulation of neural activity is not permanent. For example, upon cessation of the application of a signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible stimulation, the neural activity returns substantially fully to baseline neural activity. That is, the neural activity following cessation of the application of a signal is substantially the same as the neural activity prior to a signal being applied. Hence, the nerve or the portion of the nerve has regained its normal physiological capacity to propagate action potentials.

In other embodiments, stimulation of neural activity may be substantially persistent. As used herein, "persistent" is taken to mean that the neural activity has a prolonged effect. For example, upon cessation of the application of a signal, neural activity in the nerve remains substantially the same as when the signal was being applied—i.e. the neural activity during and following signal application is substantially the same. Reversible modulation is preferred.

Application in Therapy

The invention is useful in treating acute medical conditions, and in particular, the invention can be used as an intervention option as the last resort. The invention is particularly useful for treating life-threatening conditions, such as those having physiological changes associated with shock, and cardiovascular dysfunction.

Examples of these conditions include trauma, hemorrhaging and shock.

Trauma includes, for example, physical injuries caused by an external source, such as blunt trauma (including motor vehicle collisions, falls, head injuries, lacerations), penetrating trauma (such as cuts, stab wounds, impalements), blast injury, burns (caused by heat, cold, electricity, chemicals, friction or radiation) and combinations thereof.

Hemorrhaging is a loss of blood from the circulatory system. Hemorrhaging includes, for example, hematemesis (vomiting fresh blood), hemoptysis (coughing up blood from the lungs), hematuria, cerebral hemorrhage, pulmonary hemorrhage, postpartum hemorrhage and gastrointestinal bleeds. Hemorrhaging may result from, for example, traumatic injury or an underlying medical condition. Hemorrhaging also includes inter-operative hemorrhage and post-operative hemorrhage.

Shock includes, for example, septic shock, anaphylactic shock, toxic shock syndrome, cardiogenic shock, hypovolemic shock and neurogenic shock. The invention is particularly useful in treating septic shock.

The invention is of particular interest in relation to trauma, septic shock, haemorrhage, severe hemophilia, severe episodes of lupus, episodes of severe Crohn's, allograph/graph rejection, anaphylaxis, and endotoxic shock.

Treatment of the condition can be assessed in various ways, but typically involves determining an improvement in one or more physiological parameters of the subject. As used herein, an "improvement in a determined physiological parameter" is taken to mean that, for any given physiological parameter, an improvement is a change in the value of that parameter in the subject towards the normal value or normal range for that value—i.e. towards the expected value in a healthy subject.

As used herein, "worsening of a determined physiological parameter" is taken to mean that, for any given physiological parameter, worsening is a change in the value of that parameter in the subject away from the normal value or normal range for that value—i.e. away from the expected value in a healthy subject.

For example, an acute medical condition may be accompanied by a drop in blood pressure, dizziness or lightheadedness, a rash, nausea, muscle pain, shortness of breath, oliguria, muscle pain, and cold, clammy and pale or mottled skin.

The body's vital signs are particularly useful for assessing acute medical conditions as these are signs that indicate the status of the body's vital (life-sustaining) functions. A vital sign may be one or more of the group consisting of: systemic arterial pressure, body temperature, heart rate, breathing rate, oxygen saturation, and pain sensation.

Other useful physiological parameters may be systemic venous pressure, pulmonary artery pressure (also referred to herein as pulmonary pressure), hourly urine output, the level of consciousness, arterial partial pressure of oxygen and arterial partial pressure of carbon dioxide.

Any one or a combination of the physiological parameters may be useful with the invention.

In a subject having an acute medical condition, an improvement in a physiological parameter indicative of treatment of the acute medical condition may (depending on which abnormal values a subject is exhibiting) be one or more of the group consisting of: restoring the body temperature to between 36° C. and 38° C., restoring the heart rate to 60-100 bpm, restoring the systemic arterial pressure to between 90/60 mmHg and 150/90 mmHg, restoring the systemic venous pressure to about 5 mmHg in the right atrium and about 8 mmHg in the left atrium, restoring the central venous pressure to in the range of about 3-8 mmHg, restoring the pulmonary pressure to about 15 mmHg, restoring the breathing rate to 8-14 breaths per minute, an increase in oxygen saturation to ≥94%, an increase the arterial partial pressure of oxygen to 12-15 kPa, restoring the arterial partial pressure of carbon dioxide to 4.4-6.1 kPa, a reduction of pain sensation, restoring urine output to ≥0.5 ml/kg/hr, increase the level of consciousness, a reduction in the level of lactate, a change in the level of blood glucose, a change in the level of base deficit in blood and a change in the level of arterial pH. The invention might not lead to a change in all of these physiological parameters.

The invention aims to restore the blood pressure (e.g. systemic arterial pressure, systemic venous pressure, central venous pressure and pulmonary pressure) to the normal range. As would be known to the skilled person, when referring to blood pressure in the art, it generally refers to the arterial pressure in the systemic circulation (i.e. systemic arterial pressure), unless otherwise specified. Normal systemic arterial pressure is considered to be between 90/60 mmHg and 120/80 mmHg. Systemic arterial pressure values below this range may indicate that the individual is suffering from shock. The invention aims to restore systemic arterial pressure to the normal range. Hence, when a subject is suffering from shock, the invention aims to increase the systemic arterial pressure.

Determining the systemic venous pressure, central venous pressure and the pulmonary pressure may also be useful with the invention. Determining these pressures usually require invasive tools, such as a catheter. However pulmonary pressure may be determined using ultrasound measurements, for example, of the diameter of the inferior vena cava and the apparent cardiac filling pressure. The normal range of systemic venous pressure in a healthy adult is usually 5 mmHg in the right atrium and 8 mmHg in the left atrium. The normal range of central venous pressure in a healthy adult is considered to be in the range of about 3-8 mmHg. The normal range of the pulmonary pressure in a healthy adult is usually about 15 mmHg at rest.

The invention also aims to restore the body temperature to the normal range, i.e. between 36° C. and 38° C.

The heart rate is normally considered to be 60-100 bpm, but in acute medical conditions, the heart rate typically is increased. The invention aims to restore the heart rate to the normal range, i.e. it aims to reduce the heart rate.

The normal breathing rate is 8-14 breaths per minute, and the invention aims to restore breathing rate to the normal range.

Healthy individuals at sea level usually exhibit oxygen saturation ($SO_2$) values between 96% and 99%, and are usually above 94%. If the level is below 90%, it is considered low resulting in hypoxemia. Blood oxygen levels below 80 percent may compromise organ function, such as the brain and heart. Continued low oxygen levels may lead to respiratory or cardiac arrest. Oxygen saturation is commonly measured using pulse oximetry.

The normal range of arterial partial pressure of oxygen in a healthy individual is usually 12-15 kPa. The normal range of arterial partial pressure of carbon dioxide is usually 4.4-6.1 kPa. The invention aims to restore arterial partial pressure of oxygen and arterial partial pressure of oxygen to the normal range.

The normal urine output for an adult is 0.5-1 ml/kg/hr. This roughly equates to 30-60 ml per hour in an average sized adult. The invention aims to urine output to the normal range.

Further physiological parameters useful with the invention may include the level of lactate, blood glucose, base deficit in blood and arterial pH. These parameters can be determined by biochemical analyses.

Suitable methods for determining the value for any given parameter would be appreciated by the skilled person.

The skilled person will appreciate that the baseline for any physiological parameter in an subject need not be a fixed or specific value, but rather can fluctuate within a normal range or may be an average value with associated error and confidence intervals. For example, the normal ranges for a person's vital signs vary with age, weight, gender, and overall health. Suitable methods for determining baseline values are well known to the skilled person.

As used herein, a physiological parameter is determined in a subject when the value for that parameter exhibited by the subject at the time of detection is determined. A detector (e.g. a physiological sensor subsystem, a physiological data processing module, a physiological sensor, etc.) is any element able to make such a determination. Detecting any of the physiological parameters may be done before, during and/or after modulation of neural activity in the sympathetic nerve according to the invention. Detection can be performed manually by a human (e.g. a clinician or caregiver), with or without the use of a device, such as an instrument, that is not part of the system of the invention, or a detector that is part of the system of the invention. Where a device or detector is used detection can be performed autonomously.

Thus, in certain embodiments, the invention further comprises a step of determining one or more physiological parameters of the subject, wherein the signal is applied only when the determined physiological parameter meets or exceeds a predefined threshold value. In such embodiments wherein more than one physiological parameter of the subject is determined, the signal may be applied when any one of the determined physiological parameters meets or exceeds its threshold value, alternatively only when all of the determined physiological parameters meet or exceed their threshold values. In certain embodiments wherein the signal is applied by a system of the invention, the system further comprises at least one detector configured to determine the one or more physiological parameters of the subject.

In certain embodiments of the invention, the one or more detected physiological parameters are one or more of the group consisting of: blood pressure (e.g. systemic arterial pressure, systemic venous pressure and pulmonary pressure), body temperature, heart rate, breathing rate, oxygen saturation, pain sensation, hourly urine output, the level of consciousness, or the level of lactate, blood glucose, base deficit in blood and/or arterial pH. It will be appreciated that any two physiological parameters may be determined in parallel embodiments, the controller is coupled detect the pattern of action potentials tolerance in the subject.

For instance, when addressing the severity of shock and the response to a medical intervention for shock, one important factor is tissue perfusion, which may be increased during episodes of shock. Tissue perfusion may be associated with a decrease in blood pressure and a number of other changes in physiological parameters including the level of lactate and to a lesser extent base deficit and arterial pH, which some embodiment of the invention seek to restore to normal levels as described above.

A predefined threshold value for a physiological parameter is the minimum (or maximum) value for that parameter that must be exhibited by a subject or subjects before the specified intervention is applied. For any given parameter, the threshold value may be defined as a value indicative of a pathological state or a disease state. The threshold value may be defined as a value indicative of the onset of a pathological state or a disease state. Thus, depending on the predefined threshold value, the invention can be used as a treatment. Alternatively, the threshold value may be defined as a value indicative of a physiological state of the subject (that the subject is, for example, asleep, post-prandial, or exercising). Appropriate values for any given physiological parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that physiological parameter than the predefined threshold value.

A subject of the invention may, in addition to receiving neuromodulation of a splenic nerve according to the invention, receive treatments and/or medicines for the condition. For example, the subject may receive fluids given into a vein, antibiotics (e.g. penicillin, cephalosporin, tetracycline, macrolide, or fluoroquinolones) given into a vein, a medicine that increases blood pressure and/or blood flow to tissues and organs, surgery to remove the source of the infection (such as an abscess) and any tissue that has been badly damaged by the infection, oxygen given through a face mask, a cannula in the nose, or a tube passed down the throat into the trachea connected to a breathing machine (ventilator) if there is severe difficulty with breathing.

The subject may receive an anti-inflammatory medicine (which will usually continue medication which was occurring before having a system of the invention inserted). Such medicines include, nonsteroidal anti-inflammatory drugs (NSAIDs), steroids, 5ASAs, disease-modifying-anti-inflammatory drugs (DMARDs) such as azathioprine, methotrexate and cyclosporin, biological drugs like infliximab and adalimumab, and the new oral DMARDs like Jak inhibitors.

Thus the invention provides the use of these treatments and/or medicines in combination with a system of the invention.

Suitable Forms of an Electrical Signal

The invention uses an electrical signal applied via at least one electrode which placed in signaling contact with a nerve supplying the spleen, wherein the nerve is associated with a neurovascular bundle (e.g. a splenic arterial nerve). As used herein, "signaling contact" is where at least part of the electrical signal applied via the at least one electrode is received at the nerve.

The electrical signal preferably provides a single treatment e.g. in acute clinical settings. That is not to say that the electrical signal is only applied once. During the single treatment, the electrical signal may be applied to the nerve continuously or periodically. Preferably, the electrical signal is applied to the nerve until there is an improvement in a physiological parameter of the subject.

Electrical signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of the nerve or fibers thereof, or other nerve tissue to which the signal is applied, to conduct action potentials when application of the signal ceases, even if that conduction is in practice artificially stimulated as a result of application of the non-destructive signal.

Electrical signals applied according to the invention may be a voltage or a current waveform.

The electrical signal may be characterized by one or more electrical signal parameters. The electrical signal parameters include waveform, frequency, and amplitude.

Alternatively or additionally, the electrical signal may be characterized by the pattern of application of the electrical signal to the nerve. The pattern of application refers to the timing of the application of the electrical signal to the nerve. The pattern of application may be continuous application or periodic application. The pattern of application may include a set duration for signal application.

Continuous application refers to where the electrical signal is applied to the nerve in a continuous manner. In embodiments where the electrical signal is a series of pulses, the gaps between those pulses (i.e. between the pulse width and the phase duration) do not mean the signal is not continuously applied.

Periodic application refers to where the electrical signal is applied to the nerve in a repeating pattern (e.g. an on-off pattern).

Waveform

Modulation (e.g. stimulation) of a nerve supplying the spleen, wherein the nerve is associated with a neurovascular bundle (e.g. a splenic arterial nerve) can be achieved using electrical signals which serve to replicate the normal neural activity of the nerve. Thus, the waveform of the electrical signal may comprise one or more pulse trains, with square, sawtooth, sinusoidal, triangular, trapezoidal, quasitrapezodial or complex pulses. In other embodiments, the waveform may be a square, sinusoidal, triangular, trapezoidal, quasi-trapezodial or a complex waveform. In other embodiments, the waveform may be a constant amplitude waveform.

The signal may be biphasic. The term "biphasic" refers to a signal which applies to the nerve over time both a positive and negative charge.

The signal may be symmetric or asymmetric. A symmetric signal is a signal where the waveform when applying a positive charge to the nerve is symmetrical to the waveform when applying a negative charge to the nerve. An asymmetric signal is a signal where the waveform when applying a positive charge to the nerve is not symmetrical with the waveform when applying a negative charge to the nerve.

The signal may be charge-balanced. A charge-balanced signal refers to a signal which, over a period of the signal, applies equal amounts (or thereabouts) of positive and negative charge to the nerve.

Amplitude

For the purpose of the invention, the amplitude is referred to herein in terms of charge density per phase. Charge per phase applied to the nerve by the electrical signal is defined as the integral of the current over one phase (e.g. over one phase of the biphasic pulse in the case of a charge-balanced biphasic pulse). Thus, charge density per phase applied to the nerve by the electrical signal is the charge per phase per unit of contact area between at least one electrode and the nerve, and also the integral of the current density over one phase of the signal waveform. Put another way, the charge density per phase applied to the nerve by the electrical signal is the charge per phase applied to the nerve by the electrical signal divided by the contact area between at least one electrode (generally the cathode) and the nerve.

The charge density per phase required by the invention represents the amount of energy required to stimulate neural activity in a nerve supplying the spleen, wherein the nerve is associated with a neurovascular bundle (e.g. a splenic arterial nerve), to improve a physiological parameter.

The inventors found the charge density per phase required to stimulate neural activity in a porcine splenic arterial nerve to be between 5 $\mu$C to 150 $\mu$C per $cm^2$ per phase or in some cases between 5 $\mu$C to 180 $\mu$C per $cm^2$ per phase using an extravascular cuff (values may be slightly affected by electrode design). For example, the charge density per phase applied by the electrical signal may be ≤10 $\mu$C per $cm^2$ per phase, ≤15 $\mu$C per $cm^2$ per phase, ≤20 $\mu$C per $cm^2$ per phase, ≤25 $\mu$C per $cm^2$ per phase, ≤30 $\mu$C per $cm^2$ per phase, ≤40 $\mu$C per $cm^2$ per phase, ≤50 $\mu$C per $cm^2$ per phase, ≤75 $\mu$C per $cm^2$ per phase, ≤100 $\mu$C per $cm^2$ per phase, ≤125 $\mu$C per $cm^2$ per phase, ≤150 $\mu$C per $cm^2$ per phase or ≤180 $\mu$C per $cm^2$ per phase. Additionally or alternatively, the charge density per phase applied by the electrical signal may be ≥5 $\mu$C per $cm^2$ per phase, ≥10 $\mu$C per $cm^2$ per phase, ≥15 $\mu$C per $cm^2$ per phase, ≥20 $\mu$C per $cm^2$ per phase, ≥25 $\mu$C per $cm^2$ per phase, ≥30 $\mu$C per $cm^2$ per phase, ≥40 $\mu$C per $cm^2$ per phase, ≥50 $\mu$C per $cm^2$ per phase, ≥75 $\mu$C per $cm^2$ per phase, ≥100 $\mu$C per $cm^2$ per phase, ≥125 $\mu$C per $cm^2$ per phase, or ≥150 $\mu$C per $cm^2$ per phase. Any combination of the upper and lower limits above is also possible.

The inventors further found the indicated estimation of charge density per phase required to stimulate neural activity in a human splenic arterial nerve to be between approximately 70-1300 $\mu C/cm^2$. For example, the charge density per phase applied by the electrical signal may be ≤80 $\mu$C per $cm^2$ per phase, ≤140 $\mu$C per $cm^2$ per phase, ≤170 $\mu$C per $cm^2$ per phase, ≤230 $\mu$C per $cm^2$ per phase, ≤250 $\mu$C per $cm^2$ per phase, ≤300 $\mu$C per $cm^2$ per phase, ≤350 $\mu$C per $cm^2$ per phase, ≤400 μC per cm² per phase, ≤450 μC per cm² per phase, ≤500 μC per cm² per phase, ≤1100 μC per cm² per phase, or ≤1300 μC per cm² per phase. Additionally or alternatively, the charge density per phase applied by the electrical signal may be ≥70 μC per cm² per phase, ≥140 μC per cm² per phase, ≥170 μC per cm² per phase, ≥230 μC per cm² per phase, ≥250 μC per cm² per phase, ≥300 μC per cm² per phase, ≥350 μC per cm² per phase, ≥400 μC per cm² per phase, ≥450 μC per cm² per phase, ≥500 μC per cm² per phase, ≥1100 μC per cm² per phase, or ≥1300 μC per cm² per phase. Any combination of the upper and lower limits above is also possible.

The total charge applied to the nerve by the electrical signal in any given time period is a result of the charge density per phase of the signal, in addition to the frequency of the signal, the pattern of application of the signal and the area in contact between at least one electrode and the nerve. The frequency of the signal, the pattern of application of the signal and the area in contact between at least one electrode and the nerve are discussed further herein.

It will be appreciated by the skilled person that the amplitude of an applied electrical signal necessary to achieve the intended stimulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

It would be of course understood in the art that the electrical signal applied to the nerve would be within clinical safety margins (e.g. suitable for maintaining nerve signaling function, suitable for maintaining nerve integrity, and suitable for maintaining the safety of the subject). The electrical parameters within the clinical safety margin would typically be determined by pre-clinical studies.

Periodic Application

Periodic application refers to where the electrical signal is applied to the nerve in a repeating pattern. The preferred repeating pattern is an on-off pattern, where the signal is applied is applied for a first duration, referred to herein as an 'on' duration, then stopped for a second duration, referred to herein as an 'off' duration, then applied again for the first duration, then stopped again for the second duration, etc.

The periodic on-off pattern may have an on duration of between 0.1 and 10 s and an off duration of between 0.5 and 30 s. For example, the on duration (referred as the time during which pulses at a certain frequency and amplitude are delivered to the nerve) may be ≤0.2 s, ≤0.5 s, ≤1 s, ≤2 s, ≤5 s, or ≤10 s. Alternatively or additionally, the on duration may be ≥0.1 s, ≥0.2 s, ≥0.5 s, ≥1 s, ≥2 s, or ≥5 s. Any combination of the upper and lower limits above for the on duration is also possible. For example, the off duration (referred to the time between on periods, during which no pulses are delivered to the nerve) may be ≤1 s, ≤3 s, ≤5 s, ≤10 s, ≤15 s, ≤20 s, ≤25 s, or ≤30 s. Alternatively or additionally, the off duration may be ≥0.5 s, ≥1 s, ≥2 s, ≥5 s, ≥10 s, ≥15 s, ≥20 s, or ≥25 s. Any combination of the upper and lower limits above for the off duration is also possible.

Periodic application may also be referred to as a duty cycled application. A duty cycle represents the percentage of time that the signal is applied to the nerve for a cycle of the periodic pattern. For example, a duty cycle of 20% may represent a periodic pattern having an on duration of 2 s, and an off duration of 10 s. Alternatively, a duty cycle of 20% may represent a periodic pattern having a on duration of 1 s, and an off duration of 5 s. In other words, periodic application may also be referred to as on-off pattern stimulation, or burst stimulation.

Duty cycles suitable for the present invention are between 0.1% and 100%.

Duration

The signal is applied for a particular duration, during which the signal can be applied periodically or continuously. A clinician may determine the duration, or the duration may be preset.

A clinician may cause the signal to stop being applied during the duration in response to a physiological parameter of the subject. Preferably, the electrical signal is applied to the nerve until there is an improvement in a physiological parameter of the subject.

In some examples, the duration may be ≤1 min, ≤5 min, ≤10 min, ≤30 mins, or ≤1 hour. Additionally or alternatively, the duration may be ≥1 min, ≥5 min, ≥10 min, or ≥30 mins.

Frequency

Frequency is defined as the reciprocal of the phase duration of the electrical waveform (i.e. 1/phase).

The inventors have found preferred frequencies for stimulating a nerve supplying the spleen, wherein the nerve is associated with a neurovascular bundle (e.g. a splenic arterial nerve). In particular, the inventors have found preferred frequencies for embodiments where the electrical signal is applied periodically and for embodiments where the electrical signal is applied continuously.

As previously noted, embodiments where the electrical signal is applied periodically and embodiments where the electrical signal is applied continuously provide different functions using different stimulation parameters. A continuous stimulation may be used to induce blood flow changes within the splenic vasculature that can be detected and used as on-table or peri-surgically as an indicator of successful electrode placement and/or amplitude determination; and a periodic stimulation may be used as a preferred treatment paradigm, whereby such blood flow change and/or other possible systemic effects are avoided whilst maintaining efficacy as a treatment.

In embodiments where the electrical signal is applied periodically, the electrical signal has a frequency of ≤300 Hz, preferably ≤50 Hz, more preferably ≤10 Hz. For example, the frequency of the electrical signal may be ≤50 Hz, ≤100 Hz, ≤150 Hz, ≤200 Hz, ≤250 Hz or ≤300 Hz. In other examples, the frequency of the electrical signal may be ≤10 Hz, ≤15 Hz, ≤20 Hz, ≤25 Hz, ≤30 Hz, ≤35 Hz, ≤40 Hz, ≤45 Hz, or ≤50 Hz. In further examples, the frequency may be ≤1 Hz, ≤2 Hz, ≤5 Hz, or ≤10 Hz. Additionally or alternatively, the frequency of the electrical signal may be ≥10 Hz, ≥15 Hz, ≥20 Hz, ≥25 Hz, ≥30 Hz, ≥35 Hz, ≥40 Hz, ≥45 Hz, or ≥50 Hz. In other examples, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

In embodiments where the electrical signal is applied continuously, the electrical signal has a frequency of ≤50 Hz, preferably ≤10 Hz, more preferably ≤2 Hz, even more preferably ≤1 Hz. For example, the frequency may be ≤0.1 Hz, ≤2 Hz, ≤5 Hz, or ≤10 Hz. In other examples the frequency may be ≤0.1 Hz, ≤0.2 Hz, ≤0.3 Hz, ≤0.4 Hz, ≤0.5 Hz, ≤0.6 Hz, ≤0.7 Hz, ≤0.8 Hz, or ≤0.9 Hz. Additionally or alternatively, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

Where the signal waveform comprises a pulse train, the pulses are applied to the nerve at intervals according to the above-mentioned frequencies. For example, a frequency of 50 Hz results in 50 pulses being applied to the nerve per second.

Electrode and Neural Interface Design

The electrical signal is applied to a nerve supplying the spleen, wherein the nerve is associated with a neurovascular bundle (e.g. a splenic arterial nerve) via at least one electrode in signaling contact with the nerve. The at least one electrode may be positioned on a neural interface.

In some embodiments, the electrode and/or neural interface is configured for placement around at least one splenic arterial nerve and/or around the splenic artery. In such embodiments, the neural interface may be a cuff type interface, but other interfaces which partially or fully circumvent the nerve may be used.

In other embodiments, the neural interface 10 is configured for placement on the at least one splenic arterial nerve and/or on the splenic artery. In such embodiments, the neural interface 10 may be a patch or clip type interface.

In other embodiments, the neural interface 10 is configured for placement in the splenic artery. In such embodiments, the neural interface may be a catheter or a probe type interface.

In other embodiments, the neural interface 10 is configured for placement in at least one splenic arterial nerve. In such embodiments, the neural interface may be a pin type interface.

The neural interface comprises at least one electrode. The electrodes may fabricated from, or be partially or entirely coated with, a high charge capacity material such as platinum black, iridium oxide, titanium nitride, tantalum, poly (elthylenedioxythiophene) and suitable combinations thereof.

In some embodiments, the neural interface is suitable for applying electrical signals to splenic arterial nerves at a site where the splenic artery is not in direct contact with the pancreas. Applying electrical signals to splenic arterial nerves at a site where the splenic artery is not in direct contact with the pancreas is advantageous due to the additional space available around the splenic artery. This provides additionally flexibility in the design of the neural interface 10, in particular the design of the at least one electrode.

The at least one electrode may be a flat interface electrode which is flexible, particularly in embodiments where the neural interface is configured for placement on or around the at least one splenic arterial nerve and/or the splenic artery so as to circumvent the nerve, and/or the splenic artery when the neural interface 10 is secured on the nerve. However, other electrode types are also suitable for use in the invention.

Other electrode types suitable for the present invention include cuff electrodes (e.g. spiral cuff, helical cuff or flat interface); hemi-cuff electrodes; a mesh, a linear rod-shaped lead, paddle-style lead or disc contact electrodes (including multi-disc contact electrodes); hook electrodes; sling electrodes; intrafascicular electrodes; glass suction electrodes; paddle electrode; and percutaneous cylindrical electrodes.

The at least one electrode may comprise a first electrode 11 and a second electrode 12, referred to herein as a bipolar electrode configuration. FIG. 1 shows a schematic diagram of an exemplary bipolar electrode configuration wherein the electrodes are placed in signaling contact with at least one splenic arterial nerve and/or the splenic artery. As explained elsewhere herein, suitable signaling contact may be achieved by placing the electrodes around (i.e. partially or fully circumventing) the nerve and/or artery, on the nerve and/or on the artery, or in the splenic nerve, or in the artery.

As shown in FIG. 1, the first electrode 11 and second electrode 12 are positioned along the longitudinal axis of the nerve. An electrical signal may be applied to electrodes such that the first electrode 11 is an anode and the second electrode 12 is a cathode. Alternatively, the first electrode 11 may be cathode and the second electrode 12 an anode.

In other embodiments, the at least one electrode may comprise a first electrode, a second electrode, and a third electrode, referred to herein as a tripolar electrode configuration.

As with the bipolar configuration, the first, second and third electrodes may be positioned along the longitudinal axis of the nerve, and in one example the second electrode may be positioned between the first electrode and the third electrode.

The electrodes may be at least in part insulated from one another by a non-conductive biocompatible material. To this end, a neural interface may comprise a non-conductive biocompatible material which is spaced transversely along the nerve when the device is in use.

The inventors have found preferred electrode sizes for applying an electrical signal to at least one splenic arterial nerve. The total surface area of the electrodes may be 0.1-0.3 $mm^2$. Preferably, the total surface area of the electrodes is less than 0.2 $cm^2$.

In preferred electrode configurations, the width of each of the first electrode 11 and the second electrode 12 may be between 1 and 4 mm. For example, the width may be between 1 mm and 3 mm, or between 2 mm and 4 mm, or between 2 mm and 3 mm.

Controller

Referring to FIG. 1, the system of the invention 50 which may comprises a neural interface, may also comprise at least one controller, for example microprocessor 60, which is electrically coupled to the at least one electrode of the neural interface 10 and configured to control the operation of the least one electrode. The at least one controller may be responsible for triggering the beginning and/or end of the signals delivered to the nerve by the at least one electrode. Optionally, the at least one controller may also be responsible for generating and/or controlling the signal parameters.

The at least one controller is configured to operate in an open-loop fashion, wherein a predefined signal (as described above) is delivered to the nerve with an external trigger.

The at least one controller is preferably constructed so as to generate, in use, a preconfigured and/or operator-selectable signal that is independent of any input in the system 50. The preconfigured and/or operator-selectable signal may be any one of the electrical signals previously described. In other embodiments, the at least one controller is responsive to an external signal, more preferably information (e.g. data) pertaining to one or more physiological parameters of the subject, but still within the confines of the signals previously described.

The at least one controller may be a microprocessor 60 in the system 50, suitable to be inserted in the subject.

Alternatively or additionally, the at least one controller may be a controller external to the subject.

The at least one controller may be triggered upon receipt of a signal generated by an operator, such as a physician or the subject in which the device 106 is inserted. To that end, the system 50 may additionally comprise an external system 80 comprising a controller 101. An example of such a system is described below with reference to FIG. 2.

External system 80 of wider system 100 is external the system 50 and external to the subject, and comprises controller 101. Controller 101 may be used for controlling and/or externally powering system 50. To this end, controller 101 may comprise a powering unit 102 and/or a programming unit 103. The external system 80 may further comprise a power transmission antenna 104 and a data transmission antenna 105, as further described below.

The least one controller, including microprocessor 60 and controller 101, may be a processor connected to a memory (i.e. a non-transitory computer readable storage medium) carrying an executable computer program comprising code portions which, when loaded and run on the processor, cause the processor to at least control operation of the at least one electrode. By control the operation is it meant that the at least one controller causes the at least one electrode to apply an electrical signal to the nerve using any of the signal parameters and patterns of application previously described.

Neural Stimulation System

In addition to the neural interface 10 and the at least one controller, the system 50 may comprise a signal generator 113 which is configured to deliver the electrical signal described above to the at least one electrode in response to a control operation from the at least one controller. The signal generator may comprise at least one current or voltage source.

The signal generator 113 may be electrically coupled to the at least one controller and to the at least one electrode. In some embodiments, at least one electrode may be coupled to the signal generator 113 via electrical leads 107. In some embodiments, the electrical leads may be coupled to the interconnectors previously described. Alternatively, the signal generator 113 may be directly integrated with the at least one electrode without leads. In any case, the system 50 may comprise a device 106, which may be inserted in the subject, and which may comprise DC current blocking output circuits (or AC current blocking output circuits), optionally based on capacitors and/or inductors, on all output channels (e.g. outputs to the at least one electrode, or physiological sensor 111).

In addition to the neural interface 10, the at least one electrode, the at least one controller, and the signal generator 113, the system 50 may comprise one or more of the following components: insertable transceiver 110; power source 112; memory 114 (otherwise referred to as a non-transitory computer-readable storage device); physiological sensor 111; and physiological data processing module 115. The physiological sensor 111 and physiological data processing module 115 are referred to herein as a detector.

The various components of the system 50 are preferably part of a single physical device, either sharing a common housing or being a physically separated collection of interconnected components connected by electrical leads, as shown in FIG. 2. As an alternative, however, the invention may use a system in which the components are physically separate, and communicate wirelessly. Thus, for instance, the at least one electrode and the insertable device (e.g. insertable device 106) can be part of a unitary device, or together may form a system (e.g. system 50). In both cases, further components may also be present to form a wider system (e.g. system 100).

For example, in some embodiments, one or more of the following components may be contained in the insertable device 106: power source 112; memory 114; and a physiological data processing module 115.

The power source 112 may comprise a current source and/or a voltage source for providing the power for the signal generator 113. The power source 112 may also provide power for the other components of the insertable device 106 and/or system 50, such as the microprocessor 60, memory 114, and insertable transceiver 110. The power source 112 may comprise a battery, the battery may be rechargeable.

It will be appreciated that the availability of power is limited in insertable devices, and the invention has been devised with this constraint in mind. The insertable device 106 and/or system 50 may be powered by inductive powering or a rechargeable power source.

Memory 114 may store power data and data pertaining to the one or more physiological parameters. For instance, memory 114 may store data pertaining to one or more signals indicative of the one or more physiological parameters detected by detector (e.g. via physiological sensor 111, and/or the one or more corresponding physiological parameters determined via physiological data processing module 115). In addition or alternatively, memory 114 may store power data and data pertaining to the one or more physiological parameters from external system 80 via the insertable transceiver 110. To this end, the insertable transceiver 110 may form part of a communication subsystem of the wider system 100, as is further discussed below.

Physiological data processing module 115 is configured to process one or more signals indicative of one or more physiological parameters detected by the physiological sensor 111, to determine one or more corresponding physiological parameters. Physiological data processing module 115 may be configured for reducing the size of the data pertaining to the one or more physiological parameters for storing in memory 114 and/or for transmitting to the external system via insertable transceiver 110. Insertable transceiver 110 may comprise one or more antenna(e). The insertable transceiver 100 may use any suitable signaling process such as RF, wireless, infrared and so on, for transmitting signals outside of the body, for instance to wider system 100 of which the system 50 is one part.

Alternatively or additionally, physiological data processing module 115 may be configured to process the signals indicative of the one or more physiological parameters and/or process the determined one or more physiological parameters to determine the evolution of the disease in the subject.

The physiological data processing module 115 and the at least one physiological sensor 111 may form a physiological sensor subsystem, also known herein as a detector, either as part of the system 50, part of the insertable device 106, or external to the system.

There may be at least one detector configured to detect one or more physiological parameters relating to treatment. For example, the detector may be configured for detecting biomolecule concentration using electrical, RF or optical (visible, infrared) biochemical sensors.

The memory 114 may store physiological data pertaining to normal levels of the one or more physiological parameters. The data may be specific to the subject into which the system 50 is inserted, and gleaned from various tests known in the art. Upon receipt of the signal indicative of a physiological parameter received from physiological sensor 111, or else periodically or upon demand from physiological sensor 111, the physiological data processor 115 may compare the physiological parameter determined from the signal received from physiological sensor 111 with the data pertaining to a normal level of the physiological parameter stored in the memory 114, and determine whether the received signals are indicative of insufficient or excessive of a particular physiological parameter, and thus indicative of the evolution of the disease in the subject.

The microprocessor 60 may be triggered upon receipt of a signal generated by an operator (e.g. a physician or the subject in which the system 50 is inserted). To that end, the system 50 may be part of a wider system 100 which comprises external system 80 and controller 101, as is further described below.

Beyond the Neural Stimulation System

The neural stimulation system 50 may be part of a wider system 100 that includes a number of subsystems, for example the external system 80, see FIG. 2. The external system 80 may be used for powering and programming the neural stimulation system 50 through human skin and underlying tissues.

The external subsystem 80 may comprise, in addition to controller 101, one or more of: a powering unit 102, for wirelessly recharging the battery of power source 112 used to power the insertable device 106; and, a programming unit 103 configured to communicate with the insertable transceiver 110. The programming unit 103 and the insertable transceiver 110 may form a communication subsystem. In some embodiments, powering unit 102 is housed together with programing unit 103. In other embodiments, they can be housed in separate devices.

The external subsystem 80 may also comprise one or more of power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the insertable device 106, and may be used in addition to the power transmission antenna 104 for transmitting an electromagnetic field at a high frequency (e.g., from 1 MHz to 10 GHz). The at least one antennae of the insertable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of insertable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of insertable transceiver 110 can be used in system 50 for data reception and transmission from/to the external system 80. If more than one antenna is used in the system 50, these antennae are rotated 30 degrees from one another to achieve a better degree of power transfer efficiency during slight misalignment with the with power transmission antenna 104.

External system 80 may comprise one or more external body-worn physiological sensors 121 (not shown) to detect signals indicative of one or more physiological parameters. The signals may be transmitted to the system 50 via the at least one antennae of insertable transceiver 110. Alternatively or additionally, the signals may be transmitted to the external system 50 and then to the system 50 via the at least one antennae of insertable transceiver 110.

For example, in a particular embodiment a detector external to the insertable device may include a non-invasive blood flow monitor, such as an ultrasonic flowmeter and/or a non-invasive blood pressure monitor, and determining changes in physiological parameters, in particular the physiological parameters described above.

The system 100 may include a safety protection feature that discontinues the electrical stimulation of the nerve in the following exemplary events: abnormal operation of the system 50 (e.g. overvoltage); abnormal readout from an inserted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the system 50, or internally within the system 50.

The external system 80 may comprise an actuator 120 (not shown) which, upon being pressed by an operator (e.g. a physician or the subject), will deliver a signal, via controller 101 and the respective communication subsystem, to trigger the microprocessor 60 of the system 50 to deliver a signal to the nerve by the at least one electrode.

The external system 80 may comprise a display 109 for the microcontroller 60 or the controller 101 to alert the operator (e.g. a physician or the subject) to a state of the system or of the subject. The display 109 may be a monitor such as an LED monitor, or may be a visual indicator such as an LED.

System 100 of the invention, including the external system 80, but in particular system 50, is preferably made from, or coated with, a biostable and biocompatible material. This means that the system is both protected from damage due to exposure to the body's tissues and also minimizes the risk that the system elicits an unfavorable reaction by the host (which could ultimately lead to rejection). The material used to make or coat the system should ideally resist the formation of biofilms. Suitable materials include, but are not limited to, poly(3,4-ethylenedioxythiophene):p-toluene-sulfonate (PEDOT:PTS or PEDT), poly(p-xylylene) polymers (known as Parylenes) and polytetrafluoroethylene.

The insertable device 50 of the invention will generally weigh less than 50 g.

General

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium.

Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Unless otherwise indicated each embodiment as described herein may be combined with another embodiment as described herein. The term "comprising" encompasses "including" as well as "consisting" e.g. a composition "comprising" X may consist exclusively of X or may include something additional e.g. X+Y.

It will be understood that the benefits and advantages described above may relate to one embodiment or may relate to several embodiments. The embodiments are not limited to those that solve any or all of the stated problems or those that have any or all of the stated benefits and advantages.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

BRIEF DESCRIPTION OF THE DRAWINGS

Embodiments of the invention will be described, by way of example, with reference to the following drawings, in which:

FIGS. 4A-4F shows anatomical and histological analysis of the SpN along the main SpA (splenic artery) and the short gastric and epiploic arteries. FIG. 4A is a schematic representation of the splenic neuroanatomy highlighting (dashed lines) the regions where the histological analysis was performed.

FIGS. 4B to 4D show sections of the SpN at different levels, main splenic artery (FIG. 4B), short gastric (SG) arteries (FIG. 4C) and gastroepiploic (GEP) artery (FIG. 4D), stained with H&E. Nerves in FIG. 4C and FIG. 4D are indicated by the arrowheads. In FIG. 4D, the insert shows a high magnification caption of one nerve fascicle. FIG. 4E shows a box plot reporting quantification of the number of SpN fascicles at different locations (top panel) and the mean diameter distribution of the same fascicles in the different locations (bottom panel). FIG. 4F shows the number of fascicles at different locations and their relative mean diameter.

FIG. 5A is a photomicrograph of a semi-thin sections (0.5 µm thickness) of the SpA/SpN stained with Toluidine blue. No myelinated axons can be observed in the image. FIG. 5B representative traces of evoked compound action potential (eCAP) recorded from fascicles of the peri-arterial splenic nerve dissected off the artery when stimulating at 1 Hz with a peri-arterial cuff (around the entire SpN plexus) or with a small cuff around few fascicles of the SpN bundle. The traces are the average of 10 responses.

FIG. 5C shows the range of conduction velocities of the different components of the eCAP.

FIGS. 5D and 5E show the strength-duration curve of the SpN obtained by stimulating the whole plexus (FIG. 5D) or few dissected fascicles (FIG. 5E). The graphs show also the relative charge density to obtain threshold eCAP at different stimulation amplitudes. All stimulations were performed at 1 Hz to limit stimulation-induced action potential conduction slowing in the nerve.

FIGS. 6A-6G show transient changes in mSpA BF, mSpV BF, sMABP and HR that are stimulation intensity dependent caused by SpN stimulation. FIG. 6A shows the mean (n=8) change in mSpA BF (from −30 to +180 s, relative to start of stimulation) during a 1-minute stimulation (symmetric biphasic pulses, 400 µs PW at 10 Hz) of the SpN plexus at different current amplitudes (between 3.5 and 20 mA). FIG. 6B shows the maximum reduction in mSpA BF reached during a 1-minute stimulation (symmetric biphasic pulses, 400 µs PW at 10 Hz) of the SpN plexus at different current amplitudes. Each line represent an animal tested. FIG. 6C shows the mean (n≥3) maximum reduction in mSpA BF reached during a 1 minute stimulation (symmetric biphasic pulses, 400 µs or 200 µs PW at 10 Hz) of the SpN plexus at different current amplitudes and with two different PW: 400 (black circles) and 200 (black squares) µs. FIG. 6D shows the change in mSpV BF (from −30 to +180 s, relative to start of stimulation) during a 1-minute stimulation (symmetric biphasic pulses, 400 µs PW at 10 Hz) of the SpN plexus at different current amplitudes (between 3.5 and 12 mA). FIG. 6E shows the mean (n=3) change in sMABP and HR (from −30 to +180 s, relative to start of stimulation) during a 1-minute stimulation (symmetric biphasic pulses, 400 µs PW at 10 Hz) of the SpN plexus at different current amplitudes (between 3.5 and 20 mA). FIGS. 6F and 6G summarize the mean (n=3) maximum changes in mSpA BF, sMABP, HR and RR during a 1 minute stimulation (symmetric biphasic pulses, 400 µs PW at 10 Hz) of the SpN plexus (FIG. 6F) or some dissected SpN fascicles (FIG. 6G) at different current amplitudes. Both graphs show the amplitude (measured as peak to peak) of the recorded eCAP (expressed as % over the maximal response). SpA BF changes are expressed as maximum reduction from baseline in %, HR changes are expressed as beats per minute (bpm), sMABP changes are expressed as mmHg, and RR changes are expressed as breaths per minute (bpm). The two graphs also report the charge density per phase relative to the stimulation amplitude used.

FIGS. 7A-7D show that changes in mSpA BF, mSpV BF, sMABP and HR during SpN stimulation were frequency dependent. FIG. 7A shows the mean (n=3) change in mSpA BF (from −30 to +180 s, relative to stimulation) during a 1 minute stimulation (symmetric biphasic pulses, 400 µs PW at about 36.9 µC/cm$^2$/phase) of the SpN plexus at different frequencies (between 0.25 and 100 Hz). FIG. 7B shows the mean (n=3) maximum reduction in mSpA BF observed during a 1 minute stimulation (symmetric biphasic pulses, 400 µs PW at about 36.9 µC/cm$^2$/phase) of the SpN plexus at different frequencies (between 0.25 and 100 Hz). In FIG. 7C to 7D, the graphs show the changes in mSpV BF, sMABP, HR (expressed as % over prestimulation baseline) during a 1 minute stimulation (symmetric biphasic pulses, 400 µs PW at about 36.9 µC/cm$^2$/phase) of the SpN plexus at different frequencies (between 0.25 and 100 Hz). Data in FIG. 7A is expressed as mean±s.d. In FIGS. 7A and 7C to 7D, the box represents the stimulation time window.

FIG. 8 shows a representative experimental recording of local and systemic changes associated with the stimulation of few SpN fascicles dissected off the artery with different frequencies. HR, sMABP, Stimulation input, eCAP, SpA BF raw and mSpA BF data are shown from a representative experiment where frequency ranges from 3 to 300 Hz.

FIG. 10A is a Kaplan-Meier plot illustrating differences in survival time up to the pre-determined end-point at 2 hours post in vivo LPS injection. FIG. 10B is a box plot illustrating the lowest recorded mean arterial blood pressure (MABP; calculated as % of baseline) 30 minutes post LPS injection. A significant difference between SpN-T and sham group is shown; P=0.0296. FIGS. 10C and 10D are box plots illustrating the TNFα (FIG. 10C) and IL-6 (FIG. 10D) concentrations at 0.5 hour post in vivo LPS injection. A significant difference between SpN-T and SpN-P groups is shown; P=0.0117. A significant difference between SpN-T and sham groups is also shown; P=0.0043.

FIG. 11A is a Kaplan-Meier plot illustrating differences in survival time up to the pre-determined end-point at 2 hours post LPS injection. FIG. 11B is a box plot illustrating the lowest recorded mean arterial blood pressure (MABP; calculated as % of baseline) 30 minutes post LPS injection. A significant difference between SpN2S and sham group is shown. FIGS. 11C and 11D are box plots illustrating the TNFα (FIG. 11C) and IL-6 (FIG. 11D) concentrations at 0.5 hour post LPS injection.

FIG. 12A shows the anatomical distance from the coeliac trunk (Origin SA), to the imaginary sagittal plane and distances from the Origin SA to the various branching pancreatic arteries (PA). Boxes indicate the sites of resected tissue. The length of the splenic arterial loop is also shown. The site of the pancreas, spleen and stomach in relation to the splenic artery are also depicted. FIG. 12B shows the diameter of the splenic artery measured from each resected tissue sample. FIG. 12C shows the overview shows the spleen, the pancreas, splenic artery (SA), and surrounding adipose and connective tissue of cadaver III. The SA presents three loops, with a minimum height of 1.0 cm from the inner curvature of the loop to the pancreas. The characteristics can be found in Table 5.

FIGS. 13A-13B show that stimulation of the SpN causes a stabilization in the LPS-induced cardiovascular changes. FIGS. 13A and 13B show representative traces of MABP, dABP, sABP, HR, mCVP, ET CO2, SpA mBF changes over time from baseline (average of 10 min prior to LPS injection) in a Sham (FIG. 13A) or splenic nerve stimulated (FIG. 13B) animal. The LPS-induced changes in mCVP, HR, and ABP are smaller in the stimulated animal. MABP=mean arterial blood pressure; dABP=diastolic arterial blood pressure; sABP=systolic arterial blood pressure; HR=heart rate; mCVP=mean central venous pressure; ET CO2=end tidal CO2 volume; SpA mBF=splenic artery mean blood flow.

FIGS. 14A-14C shows that stimulation of the SpN causes a stabilization in the LPS-induced cardiovascular changes. FIG. 14A shows the stimulation of the SpN causes a reduction in the Pulmonary vascular resistance compared to baseline (pre-LPS injection). In sham (non-stimulated) animals subjected to LPS injection the PVS increases after LPS injection. FIG. 14B shows the stimulation of the SpN causes a higher increase in SVR as compared to sham animal, after LPS-administration. FIG. 14C shows the stimulation of the SpN causes a stronger increase in the PCWP as compared to sham animals after LPS injection. PVS=pulmonary vascular resistance; SVR=systemic vascular resistance; PCWP=pulmonary capillary wedge pressure.

FIG. 15 shows that stimulation of the SpN reduces the LPS-induced increase in systemic lipases as compared to sham (non-stimulated) animals.

FIGS. 16A-16H shows that the human splenic nerve is a plexus of peri-arterial fascicles containing slow conducting axons. FIG. 16A shows the human splenic neurovascular bundle (NVB) containing the SpA, the SpN, connective tissue, sections of pancreas and lymph nodes freshly isolated from a donor. Two small cuff electrodes (650 µm in diameter) were placed on a select few dissected fascicles. The schematic of the preparation indicates the position (a and b) of the stimulating and recording cuffs. The dotted lines indicate the areas in which the sections shown in B and C were taken. FIG. 16B shows a section of the human NVB stained with Haematoxylin and Eosin (H&E). The SpN fascicles are encircled. FIG. 16C shows the section of the stimulated fascicles that were isolated for electrophysiological study. The section was stained with H&E and shows the nerve fascicles (encircled) and fat/connective tissue. FIG. 16D shows eCAP recorded when applying monopolar, monophasic stimulation of the human SpN at 1 Hz and 400 µs PW prior (top panel) and after (bottom panel) crushing the nerve between the stimulating and recording cuff. The left box indicates the stimulation artefact while the larger box on the right indicates the area in which eCAP should be observed, with the arrows indicating the eCAP. FIG. 16E shows the recruitment curve of the human SpN quantifying the eCAP amplitude (expressed as % of the maximum response) vs the stimulation amplitude. Each point represents the average amplitude of 8 consecutive monopolar, monophasic pulses delivered at 1 Hz and 400 µs PW. FIG. 16F shows conduction velocities of all the eCAP components recorded from the human, porcine (pig) and rat SpN. FIG. 16G shows the strength-duration relationship (black circles) of the human SpN obtained by stimulating the dissected fascicles. The data represent the minimum current needed to trigger a detectable eCAP at the different PW tested. The graphs also show the corresponding charge density (black triangles) of the different stimulations (referred to the right Y axis). Least squares regression curves were plotted against the strength-duration and charge density data. FIG. 16H shows charge densities required to stimulate the SpN of the three different species at different PW. The data were fitted with linear regressions. Scale bars: FIG. 16B=2 mm; FIG. 16C=100 µm.

FIG. 19A shows a population recruitment curve for in-vivo data from porcine splenic neurovascular bundle stimulation.

MODES FOR CARRYING OUT THE INVENTION

Figure 1:
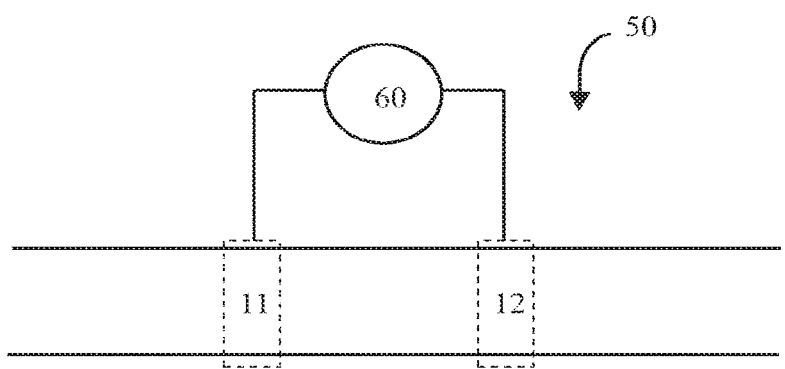
FIG. 1 illustrates a neural stimulation system.
Figure 2:
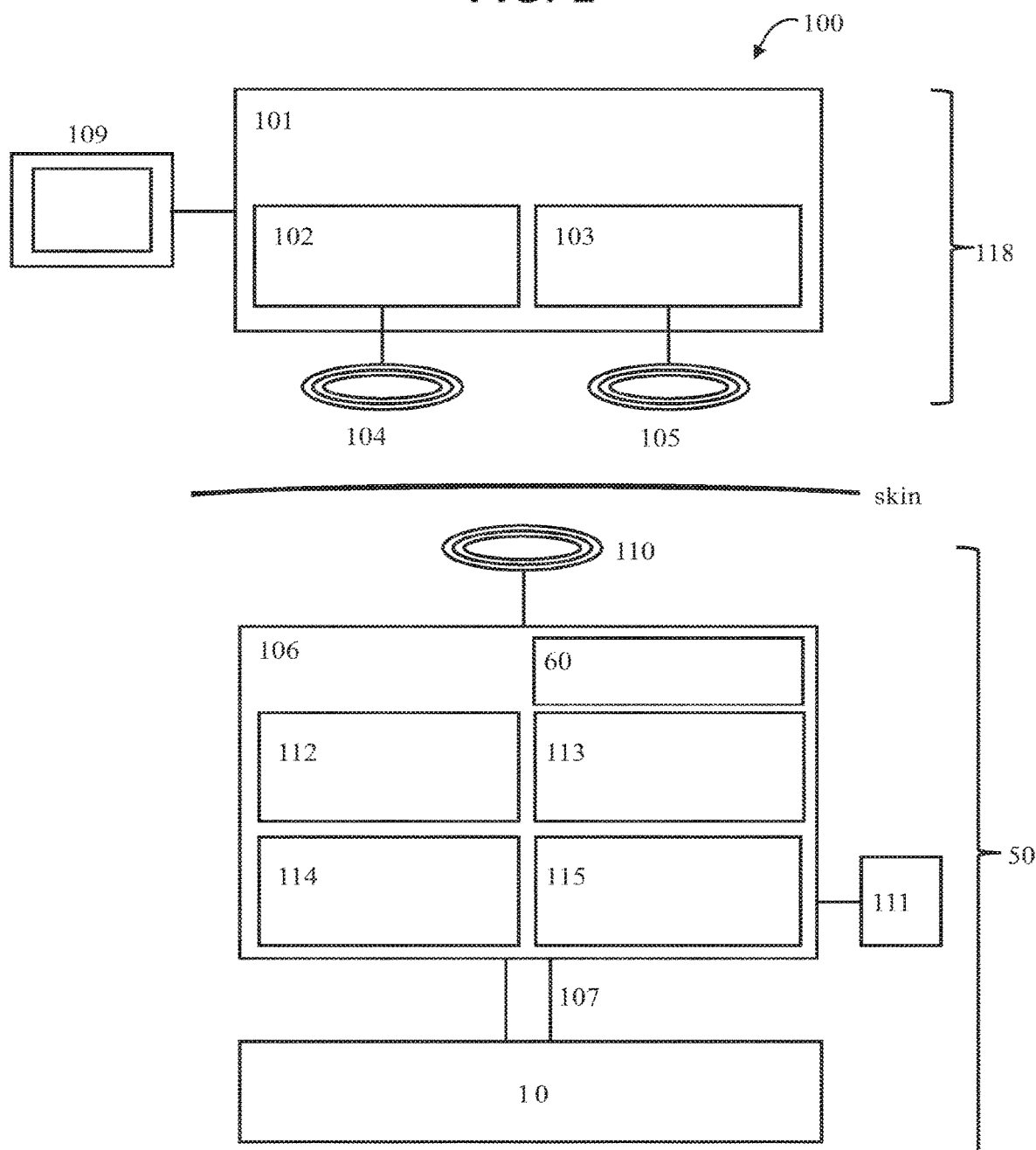
FIG. 2 illustrates a wider system including the neural stimulation system.

Study 1A: Characterization of the Splenic Arterial Nerves
Materials and Methods

Gross anatomical studies of the spleen with related organs were performed in 12 female pig cadavers (body size 22 to 120 kg) within 1 hour of euthanasia. The following measurements were made: length and width of the spleen; length of the celiac artery (from the aorta to the branching in to the left gastric and splenic arteries); length of the splenic artery (SpA) (from the branching of the celiac artery to entering the splenic parenchyma); SpA diameter measured 1 cm distal to the celiac artery and at the splenic hilum; distance from pancreas to the spleen; distance from pancreas to the splenic lymph nodes. Also, the number and course of the abdominal vagal branches, celiac ganglion, splanchnic nerves and splenic nerves were recorded. The SpA with associated splenic nerves were processed for Haematoxylin and Eosin (H&E) histology.

The spleen with intact vasculature and innervation was harvested from 12 female pig cadavers (body weight 22 kg, n=6; body weight 45 kg, n=6). All tissues were harvested within 1 hour of euthanasia, and were immediately fixated in 10% neutral-buffered formalin. The SpA with an intact perivascular neuronal network was sectioned every 5 mm from the origin at the bifurcation of the celiac artery, to the splenic hilum. This resulted in 5 sections, defined as the Bifurcation; the Proximal SpA; the Middle SpA; the Distal SpA and the Hilum location. The proximal SpA section corresponds to the location for cuff placement in the following electrical stimulation study discussed below.

At each of these five locations, sections were processed for routine H&E staining. The Proximal, Middle and Distal SpA sections were also processed for immunohistochemistry and for semi-thin sectioning and staining with osmium tetroxide and toluidine blue.

Digital images of the H&E stained sections were acquired at 2× magnification and appropriate software (Image J 1.50i) was used for histomorphometric analysis as detailed below. After manually selecting every single nerve fascicle by using the ROI manager function, the number of peri-arterial nerve fascicles were counted and the fascicle sizes assessed by measuring minimum Feret's diameter (µm).

The total nerve area (in $\mu m^2$) was calculated, and the peri-arterial fascicle distribution was quantified by assessing the percentage of the arterial circumference in which fascicles were identified, defining 360 degree distribution as 100%. The distance from each fascicle to the external arterial wall was measured by drawing the shortest possible perpendicular line from each fascicle to the arterial wall. Splenic artery external and internal diameters were measured at the proximal, middle and distal SpA locations.

Double staining with tyrosine hydroxylase (TH) and acetylcholine transferase (ChAT) was used for assessing neuronal phenotype. By counterstaining with neurofilament 200 (NF200) and the nuclear stain 4',6-diamidino-2-phenylindole (DAPI), NF200-TH double positive nerves were considered sympathetic, while NF200-ChAT double positives were considered parasympathetic nerves. In order to determine the proportion of efferent versus afferent nerves, the same locations were double stained with the efferent marker TH and the afferent marker calcitonin gene-related peptide (GCRP). Two different digital images were randomly captured at 20× magnification from each nerve, and pseudocolored composites generated using appropriate software (AxioVision LE64).

Myelination of SpN axons was assessed by immunofluorescent staining as well as from semi-thin sections. Different portions of the SpA and SpN were stained with antibodies against Neurofilament and β-III Tubulin and Myelin Basic Protein (MBP). Pseudocolored composite images were generated using appropriate software as described above. Semi-thin sections were stained with osmium and toluidine blue. Digital images were acquired at 100× magnification and the number of myelinated and unmyelinated axons were manually counted in an area of 100×100 µm. This procedure was repeated 3 times per nerve, and the mean of these were used for further analysis. Also, this procedure was used for deriving axon density (number of axons/$mm^2$).

All statistical analyses were performed with commercially available statistical software (IMP Pro 13.0.0). Due to non-normal distribution, all histomorphometric measurements were compared between the different pig sizes and SpA locations using the Wilcoxon rank-sum test. Statistical significance was defined as $P \leq 0.05$.

Results

Figure 3:
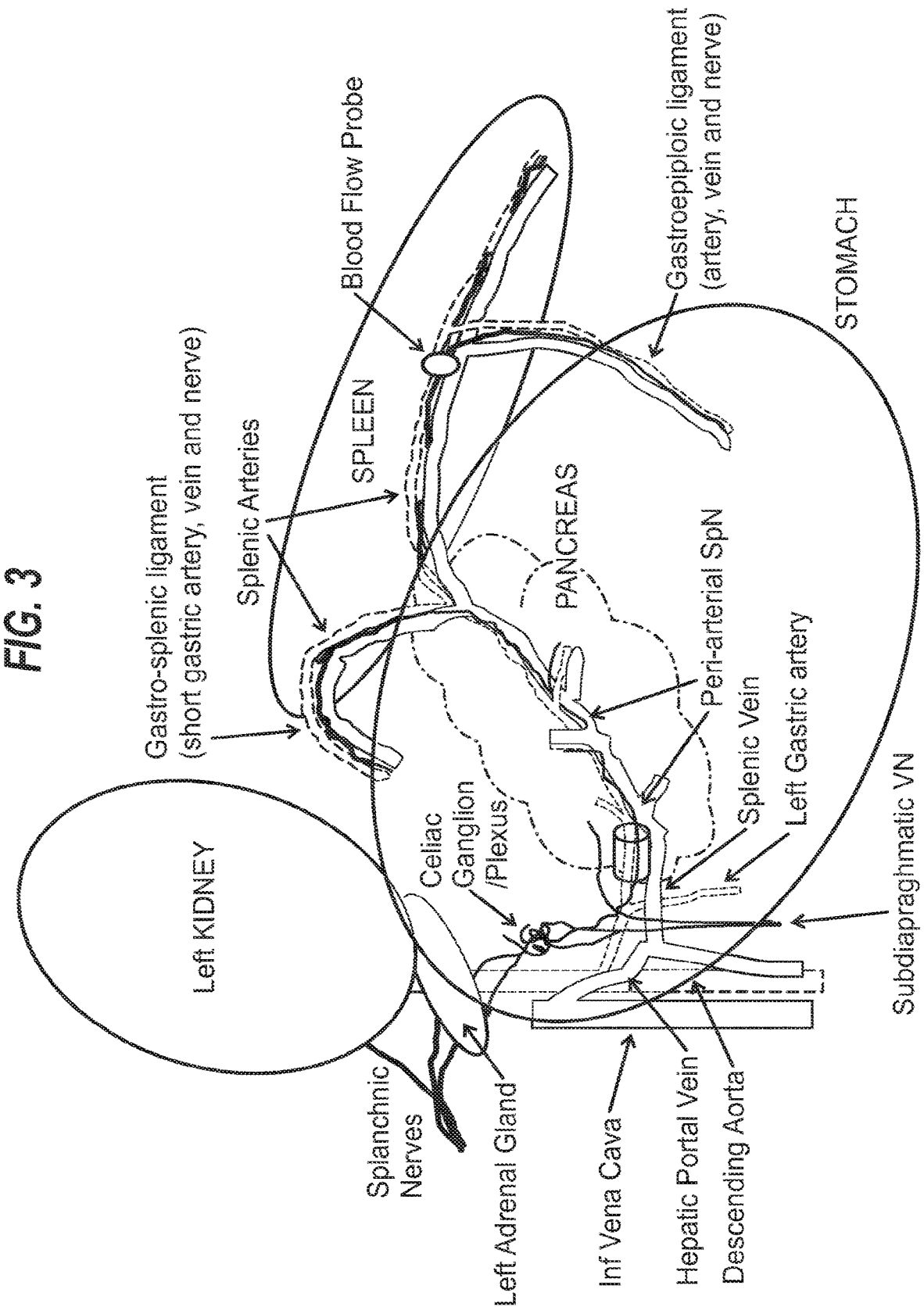
FIG. 3 is a schematic illustration of the porcine left abdomen highlighting the anatomical features of the splenic plexus (spleen, nerves, artery and veins). The location for cuff placement during the experiments of peri-arterial splenic nerve (SpN) stimulation is shown. Nerves are represented in black, and arteries and veins in grey.
Figure 4A:
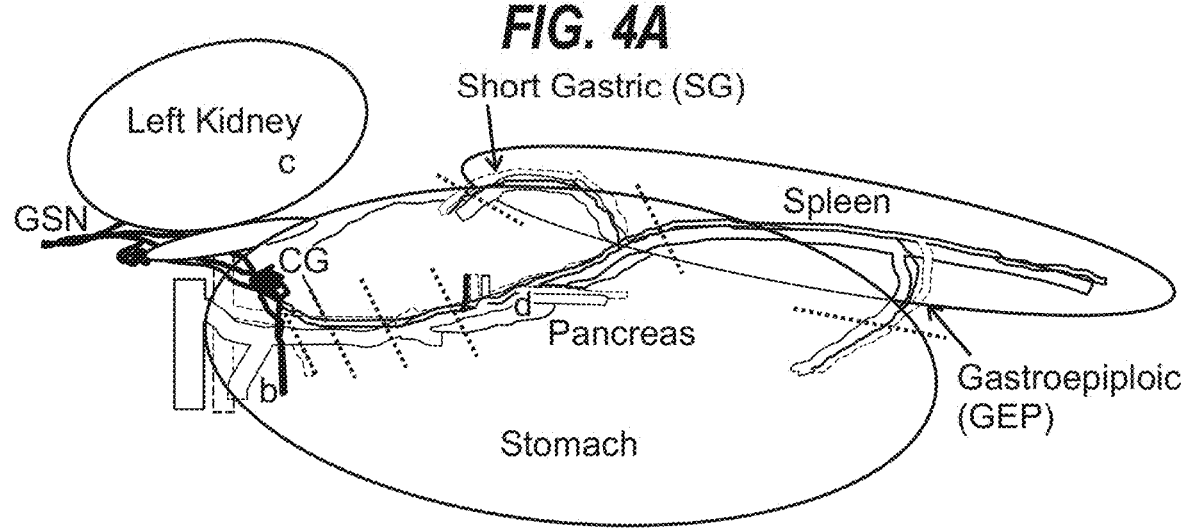
Figure 4B:
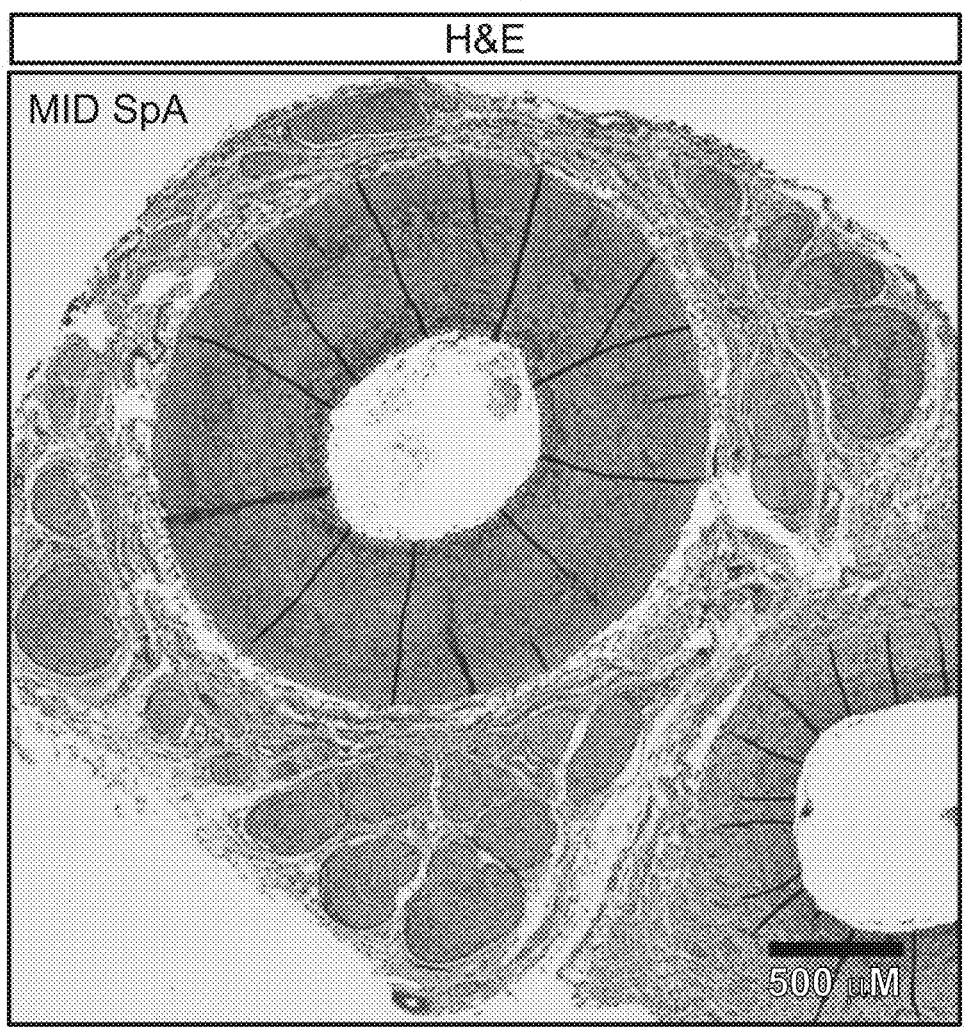
Figure 4D:
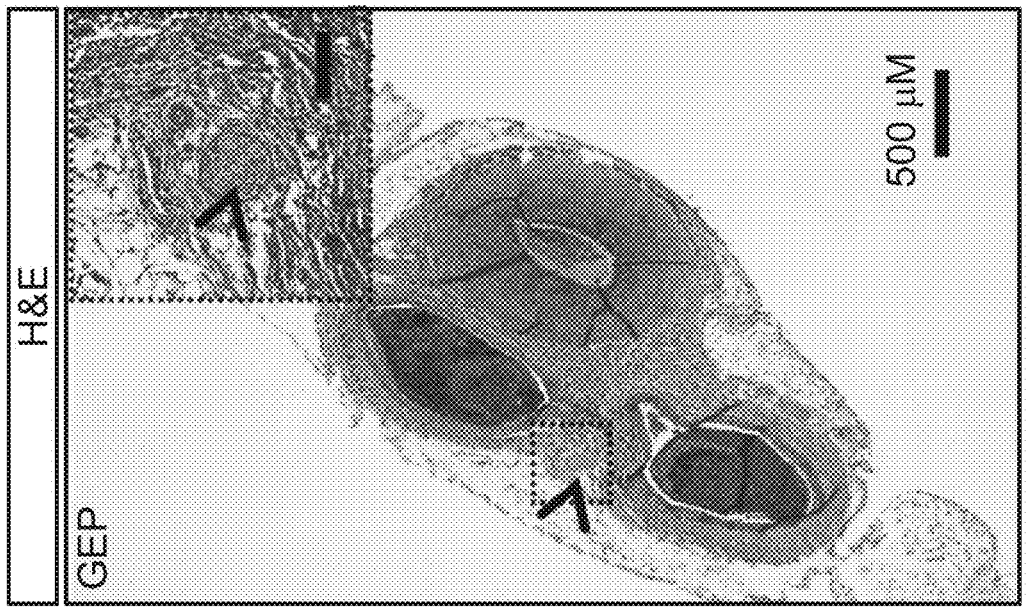
Figure 4C:
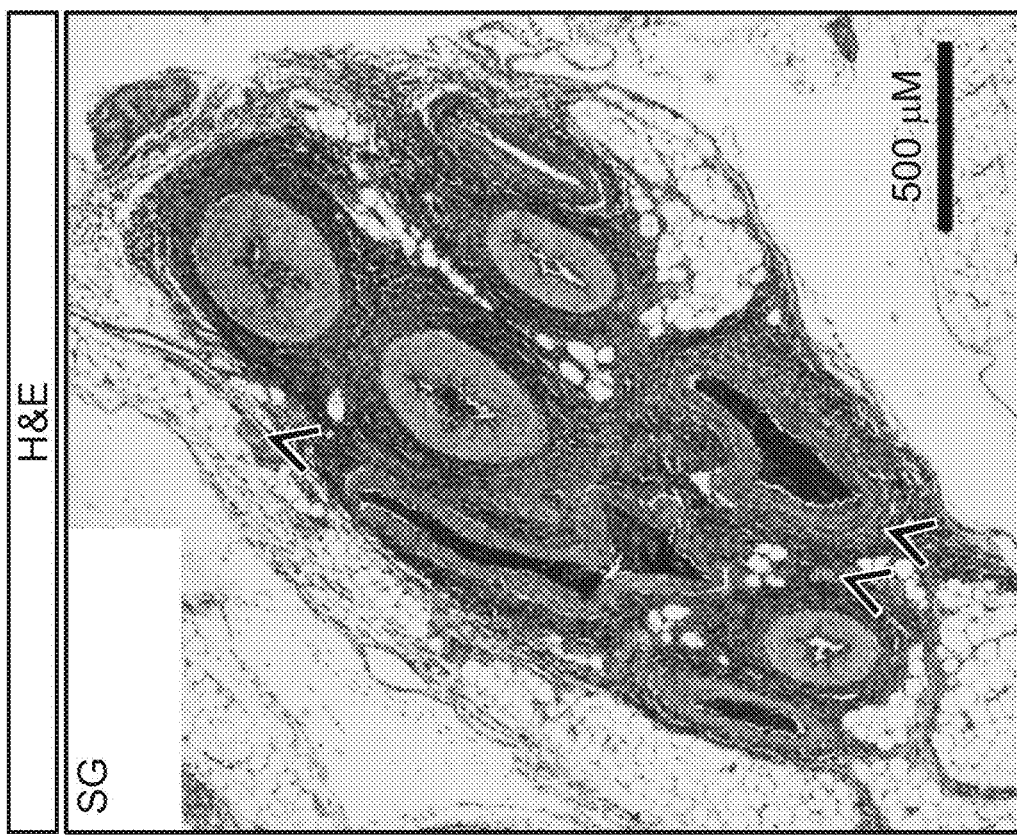

Neurovascular structures enter and leave the spleen along the visceral surface only. Specifically, the first major abdominal branch of the aorta, the celiac artery, divides into the hepatic artery, the SpA and the LGA (FIG. 3). The SpA enters the spleen at the hilum, which is located a few centimeters distal to the splenic base. At the hilum, the SpA immediately bifurcates into one dorsal branch coursing towards the splenic base, and one ventral branch running along the visceral surface towards the splenic apex. The left gastroepiploic artery arises from this ventral SpA branch approximately at the transition between the middle and the distal ⅓ of the spleen.

At the splenic base, the dorsal SpA branch divide into several smaller arteries identified as the short gastric arteries, which courses towards the greater curvature of the stomach. Although these arteries are considered terminal branches of the SpA, they are capable of providing collateral blood supply to the spleen by anastomoses with branches of the LGA and the left gastroepiploic arteries. The splenic vein (SpV) runs parallel to the SpA along the visceral surface of the spleen, from the apex to the hilum. After leaving the splenic hilum, the SpV courses closely adhered to the SpA for a short distance until it travels in a medial direction to drain into the hepatic portal vein, which in turn drains into the caudal vena cava. This leaves a small space in which the artery and the vein run separated by a few millimeters of soft tissue. This area, which is immediately distal to the bifurcation of the celiac artery into the SpA and LGA, has been identified as the optimal interface point for the following functional studies. At this location, the SpA diameter is 1.5-3 mm in the 30 kg animal; 2-4 mm in the 60 kg animal and 5-8 mm in the 110 kg animal.

The SpN consist of a plexus of fibers running along the SpA towards the splenic hilum. It is difficult to establish the origin of these nerves, although fibers can be seen arising from the CG which is located immediately caudal to the bifurcation of the celiac artery into the SpA and the LGA. Data from previous studies conducted mainly in rodents, established that most of the SpN originates from the celiac and suprarenal ganglia. This has yet to be proven in large animal species.

In rodent species, other nerves have been described to innervate the spleen in addition to the peri-arterial SpN; more specifically, an apical nerve has been described within the gastro-splenic ligament of rats and mice. This is a sympathetic nerve (TH+) possibly originating from the paravertebral sympathetic nerves, and runs towards the apex of the spleen within the gastrosplenic ligament.

All histological measurements are presented in Table 1. The SpN-SpA distance was the only measurement significantly larger in the 45 kg pigs versus the 22 kg pigs (at the middle SpA and distal SpA locations; P<0.001); therefore, for all the other measurements, data from all pigs were combined for statistical analysis. There was a reduction in number of peri-arterial nerve fascicles along the SpA from proximal to distal; there were statistically significantly more fascicles at the bifurcation versus all other locations (P<0.0001). At the splenic hilum, nerve fascicles were significantly larger than at the other locations (P<0.0001). The SpA external diameter was significantly larger at the proximal SpA location versus the middle and the distal SpA locations (P=0.0162 and P=0.0158, respectively). The SpN/SpA distance also decreased from proximal to distal; in the 45 kg pigs, the distance was significantly larger at the Bifurcation versus all other locations (P<0.001). Also in the 45 kg pigs, the SpN/SpA distance was significantly larger at the Hilum versus the Proximal, Middle and Distal SpA locations (P≤0.008).

The circumferential SpN distribution was significantly higher at the Proximal versus the Middle and Distal SpA locations (P=0.02 and P=0.15, respectively). Also, fascicles were more uniformly circumferentially distributed around the SpA at the proximal location whereas at the-middle and distal SpA, the distributional pattern was more bimodal with fascicle clustering on opposite sides of the artery.

In the pig nerves are found along both the short gastric and gastro-epiploic arteries within the gastrosplenic ligament (see FIGS. 4A-4F). These nerves seem to be a continuum of the main per-arterial SpN plexus and runs towards (or from) the stomach. At this location immunohistochemical analysis was performed and it was found that the SpN at any location is TH+ and ChAT−. Interestingly along the main SpA nerve fibers positive to Calcitonin Gene-Related Peptide (CGRP) were identified, commonly used as afferent neuronal marker.

The number of nerve fascicles and fascicle size observed in these two regions is much smaller compared to those observed along the main SpA. The quantification of the number and relative diameter of the nerve fascicles along the main SpA and along the other different anatomical locations in 45-50 Kg farm pigs is shown in FIGS. 4E and 4F.

TABLE 1

Histological measurements of SpN and SpA in 12 female pigs.

| | | Location | | | | |
|---|---|---|---|---|---|---|
| | | Bifurcation | Proximal SpA | Middle SpA | Distal SpA | Hilum |
| SpN-SpA distance (μm ± SD) | 22 kg, n = 6 | N/A | 437.5 ± 344.3 | 180.3 ± 111.6 | 161.4 ± 105.4 | N/A |
| | 45 kg, n = 6 | 1185 ± 616.2* | 476.9 ± 334.1 | 284.6 ± 166.4¥ | 382.9 ± 247.4¥ | 592.7 ± 354.2 |
| Mean no. of fascicles ± SD | | 105.8 ± 32.7* | 41.6 ± 16.5 | 29.5 ± 5.1 | 27.7 ± 5.6 | 23.8 ± 1.4 |
| Mean Feret's diameter (μm) ± SD | | 144.8 ± 100.6 | 160.3 ± 108.0 | 142.8 ± 89.7 | 157.7 ± 98.7 | 228.2 ± 157.9* |
| SpA Internal diameter (μm) ± SD | | 1020.0 ± 440.2 | 1163.8 ± 351.9 | 904.2 ± 304.1 | 690.7 ± 201.6 | |
| SpA External diameter (μm) ± SD | | 2020.7 ± 560.0 | 2255.4 ± 479Δ | 1791.6 ± 386.8 | 1574.2 ± 296.9 | |
| Neuronal circumferential distribution (% ± SD) | | | 93.6 ± 9.8Δ | 76.6 ± 19.0 | 73.8 ± 16.1 | |

¥Significantly larger in the 45 kg vs. the 22 kg pigs.
*Significantly different from all other locations.
ΔSignificantly different from the Middle and Distal SpA.
Significance P < 0.05.
N/A: Not available.

Further histochemical and immunohistochemical analysis showed that the SpN is composed by >99.9% of unmyelinated fibers. Toluidine blue staining of semi-thin sections, in fact, did not show myelinated axons. In line with this, staining for Myelin Basic Protein (MBP) revealed a very little number of positive axons (<0.01%). Both of the techniques assessing myelination revealed almost complete absence of myelin in the investigated sections of the SpN (see FIGS. 5A-5E).

Discussion

The histological analysis performed here showed that the SpN constitutes a neurovascular plexus along the main SpA as well as short gastric and gastroepiploic arteries. The number of fascicles is unexpectedly high. Considering the average size of a SpN axon (ca. 2 μm in diameter) it is possible to calculate that the SpN plexus should contain (at maximum) a total of about 150K axons at the level of the main SpA (middle section). Part of these axons will innervate the SpA endothelium and part of these axons will instead enter the spleen and forms synaptic connections with either smooth muscles or immune cells at the level of the marginal zone between white and red pulp as well as within the white pulp as previously described in other species [8,9,10,11,12]. The number of axons seems high if it is considered that the human vagus nerve (that has the same size of the pig vagus nerve), which targets several organs in the body, is supposed to contain about 100 k axons. The high number of axons in the SpN could be related to the size of the spleen in the pig, which has a volume approximately 2-3 times bigger than the human spleen, and the length of the artery that the SpN is supposed to innervate. The number of fascicles and axons in the human SpN might be different.

The spleen of pigs (and other mammals, such as dogs) is also thought to contain a higher proportion of smooth muscle cells compared to the human spleen [13]. However, several papers have also shown that the human spleen is able to contract during stressful conditions, such as apnea and physical exercise [14,15].

The vascular organization of the splenic artery and vein is slightly different between pigs and humans. In the pig the SpA and SpV run in close approximation towards and from the spleen. Moreover, SpV and SpA do not present loops or convolutions like those observed in humans. Therefore, only a short (approximately 1-1.5 cm) segment of the SpA, close to the trifurcation point of the celiac artery, is better separated from the SpV. This segment of the artery was chosen as best intervention point in the stimulation studies below. The access to the neurovascular bundle at this location is, in fact, safer, thus reducing the chances to damage the nerves as well as artery and vein during dissections.

Study 1B: Characterization of the Splenic Arterial Loops

Materials and Methods

To investigate the different neural pathways to the spleen, six formaldehyde preserved human cadavers were studied. Tissue blocks of the spleen, stomach, pancreas, greater omentum, gastrosplenic ligament and, if present, the phrenic splenic ligament were removed.

Multiple characteristics relevant to the splenic plexus were analyzed, including dissection parameters of the splenic artery in general (for example, length, cross-sectional diameter, etc) the splenic arterial loops and branches of the splenic artery, as well parameters relating to the relationship of the splenic artery with surrounding tissues.

Tissue samples of the splenic artery were also analysed by immunohistochemical staining (IHC). IHC was used to detect and quantify associated nervous tissue. General, sympathetic and afferent nervous tissue were immunohistochemically detected in tissue resections by using anti-Protein Gene Product 9.5 (PGP9.5), anti-Tyrosine Hydroxylase (TH) and anti-Calcitonin Gene-Related Peptide (CGRP) antibodies, respectively. Immunohistochemical staining and visualisation was performed using routine procedures. For all splenic plexus samples, automatically stitched overview images (tile scans) were generated from composite brightfield and fluorescent microscopy images and were the subject of further image analysis using FIJI Image J (with additional plug-ins).

Results

In all cases, the splenic artery originated from the coeliac trunk. The course was mostly suprapancreatic, although in some cadavers parts of the splenic artery were retropancreatic, intrapancreatic or anteropancreatic.

The average absolute length of the splenic artery (measured by placing a cord along the splenic artery) was 18.02 cm, with an average straight line distance from the origin at the coeliac trunk to the imaginary sagittal plane of the spleen of 11.67 cm. The imaginary sagittal plane describes the line connecting the upper and lower pole of the spleen. The average diameter of the splenic artery at its origin was 0.52 cm. The average diameter of the splenic artery before its terminal branches was 0.40 cm. The average number of terminal branches was 5.5 (2-9) and the average diameter of the terminal branches was 0.22 cm (0.05-0.5). Table 2 shows the parameters of the splenic artery for each cadaver analysed as well as the average value for each parameter.

Figure 12A:
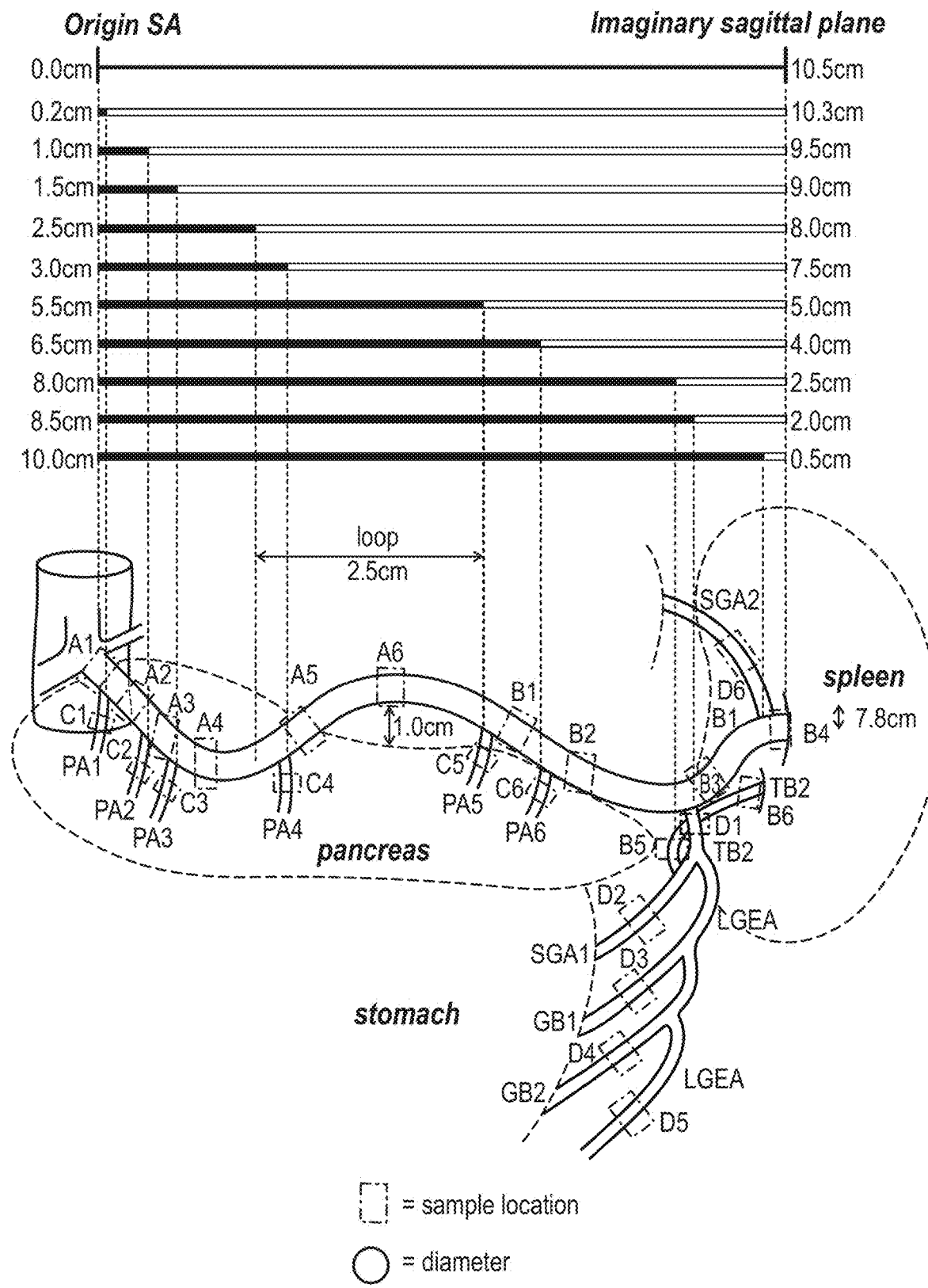
FIGS. 12A-12C show the anatomical analysis of the splenic artery from Cadaver III.
Figure 12B:
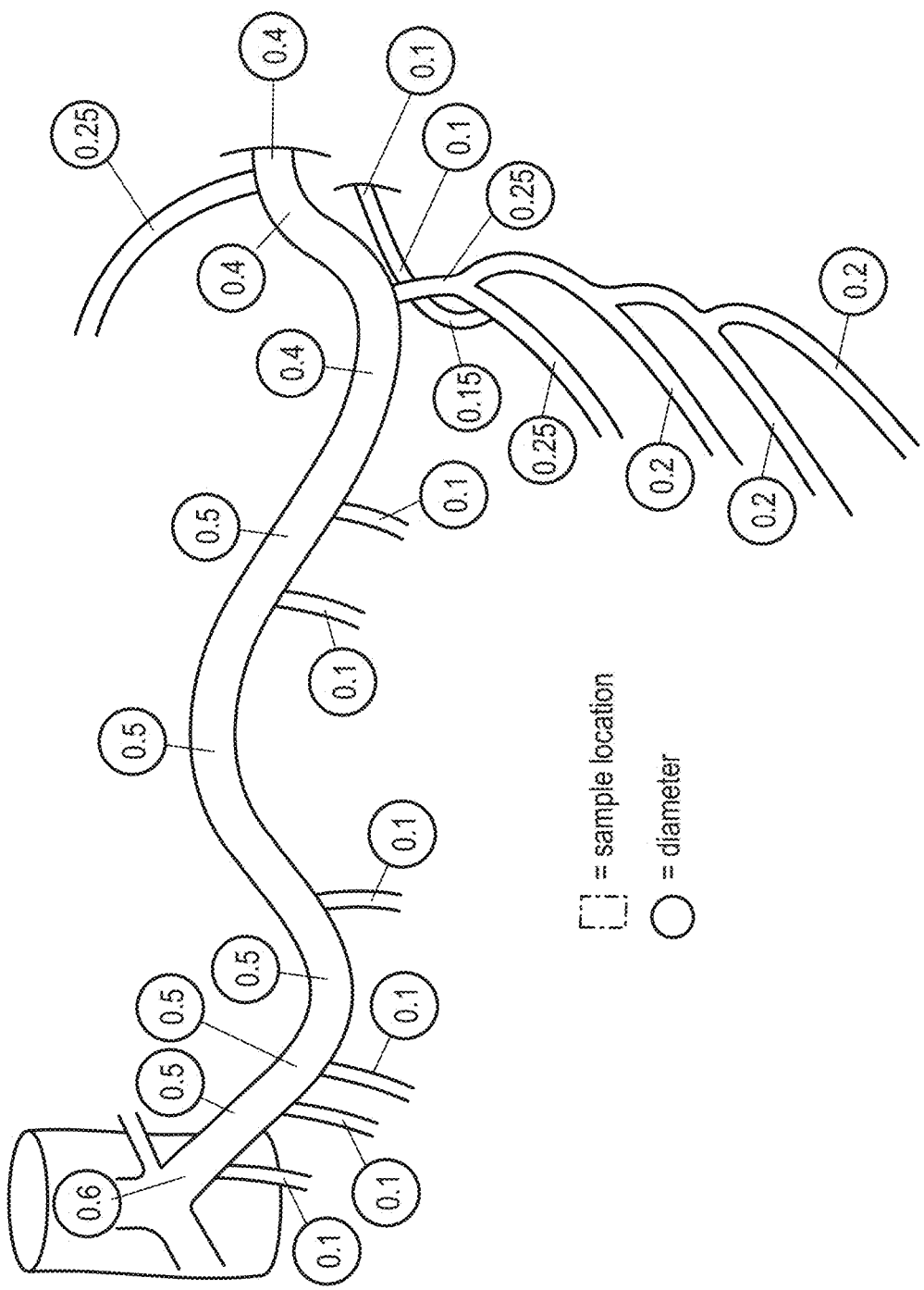
Figure 12C:
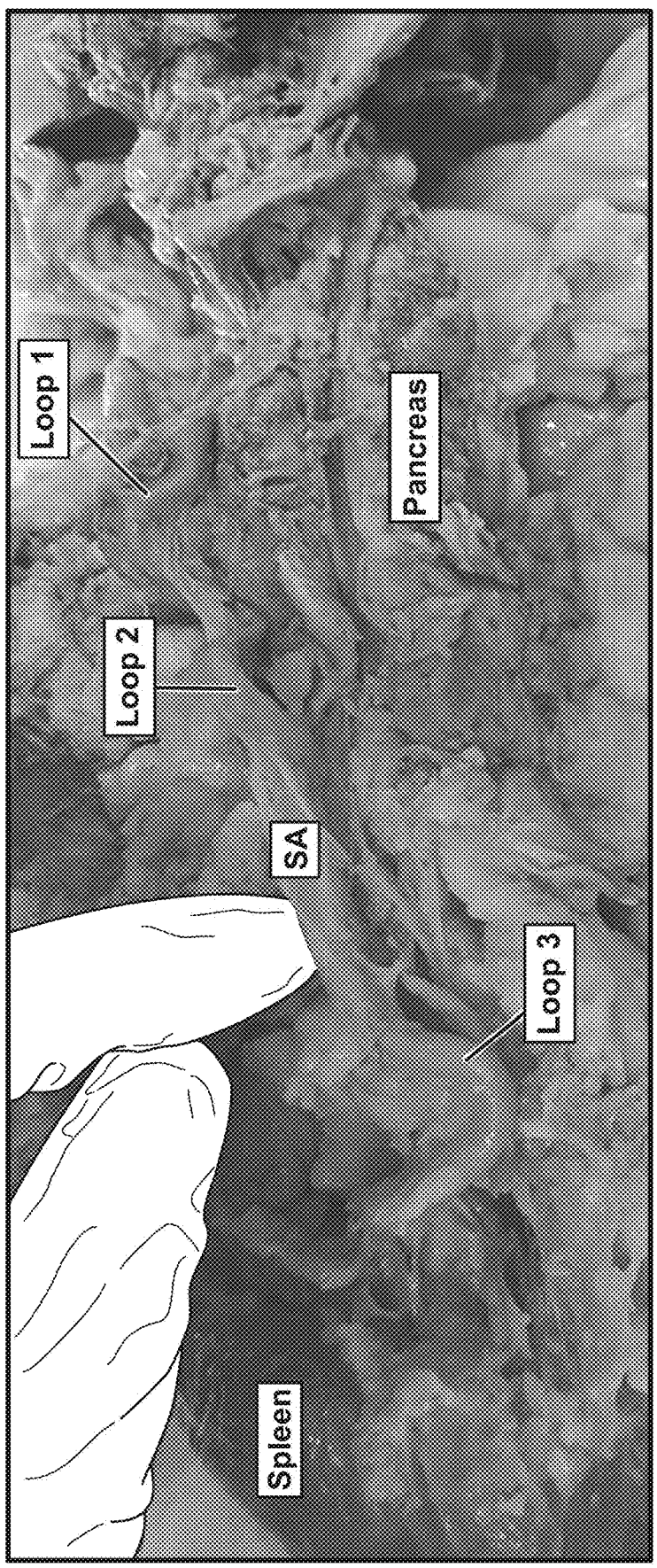

FIG. 12A shows an overview of the splenic artery and its branches of cadaver III. Distances from each branch to the origin of the SA and to the imaginary sagittal plane of the spleen are shown. In addition, the location and dimensions of the loop can be seen. The boxes show the location of the samples removed for microscopy. In FIG. 12B, the diameter of certain points along the splenic artery and its branches are depicted.

TABLE 2

Quantitative data on general dissection parameters concerning the SA of each cadaver, followed by the average value.

| | Cadaver nr. | | | | | | |
| --- | --- | --- | --- | --- | --- | --- | --- |
| | III | IV | VII | VIII | IX | X | Average |
| Absolute length SA (cm) | 18.3 | 24.5 | 19.5 | 19.9 | 12.9 | 13.0 | 18.02 (12.9-24.5) |
| Distance origin SA to spleen (cm) | 10.5 | 16.5 | 12.5 | 12.0 | 8.5 | 10.0 | 11.67 (8.5-16.5) |
| Diameter SA at origin (cm) | 0.6 | 0.3 | 0.65 | 0.45 | 0.6 | 0.5 | 0.52 (0.3-0.65) |
| Diameter SA before terminal branches (cm) | 0.4 | 0.4 | 0.5 | 0.3 | 0.5 | 0.3 | 0.40 (0.3-0.5) |

TABLE 2-continued

Quantitative data on general dissection parameters concerning the SA of each cadaver, followed by the average value.

| | Cadaver nr. | | | | | | |
|---|---|---|---|---|---|---|---|
| | III | IV | VII | VIII | IX | X | Average |
| Diameter terminal branches (cm) | 1: 0.4<br>2: 0.1 | 1: 0.4<br>2: 0.25<br>3: 0.2<br>4: 0.2<br>5: 0.2<br>6: 0.2<br>7: 0.2<br>8: 0.1<br>9: 0.1 | 1: 0.5<br>2: 0.15<br>3: 0.3<br>4: 0.3<br>5: 0.15<br>6: 0.15<br>7: 0.1<br>8: 0.1<br>9: 0.05 | 1: 0.25<br>2: 0.25<br>3: 0.15<br>4: 0.2 | 1: 0.1<br>2: 0.3<br>3: 0.3<br>4: 0.15 | 1: 0.1<br>2: 0.3<br>3: 0.4<br>4: 0.3<br>5: 0.25 | 0.22 (0.05-0.5) |

Splenic Arterial Loops

In the context of this example, a splenic arterial loop is defined as a section of the splenic artery separated from the surface of the pancreas by a distance of at least 1.0 cm. This distance is calculated from the inner curvature of the splenic artery to the surface of the pancreas.

The average number of "loops" observed across the analysed sample pool was 1.34. One cadaver did not present any loops, three cadavers presented one loop, one cadaver presented two loops and one cadaver presented three loops. The average loop neck (the distance between the inside curvature of both legs of the loop) was 1.99 cm. The average distance from the outside of the first leg of the loop to the splenic arterial origin was 6.48 cm. The average distance from the outside of the second leg of the loop to the imaginal sagittal plane of the spleen was 4.34 cm. Both these distance were highly variable. The average loop height (the distance between the inner curvature on top of the loop, and the surface of the pancreas) was 1.29 cm. The average diameter of the splenic artery preceding the first leg of the loop and succeeding the second leg of the loop were 0.46 cm and 0.41 cm, respectively. The individual and average splenic arterial loop parameters of each cadaver are shown in Table 3.

Immunohistochemical Staining.

Results of the Immunohistochemical analysis of nerve bundles surrounding splenic arterial loops is shown in Table 4. The average number of nerve bundles around splenic arterial loop was 25. The average diameter of nerve bundles was 119 μm. The average total area of sympathetic (TH-IR) nervous tissue was 196986 μm$^2$ (12645-815135), which is on average 0.54% (0.10-1.50) of the total tissue area. The diameter of the neurovascular bundle (the splenic artery and the surrounding tissue), was an average of 8553 μm (5177-12447). The distance of the nerve bundles to the location of the cuff (the outer lining of the tissue) was on average 628 μm (32-2678).

TABLE 4

Average values of all sample locations of loops of the SA for each image analysis parameter.

| | Average nerve bundle parameters of the splenic arterial loop |
|---|---|
| Number of nerve bundles | 25 (11-45) |
| Diameter nerve bundle (μm) | 119 (25-996) |
| Total TH-IR tissue (μm$^2$) | 196986 (12645-815135) |
| % TH-IR of total tissue | 0.54 (0.01-1.50) |
| Diameter neurovascular bundle (μm) | 8553 (5177-12447) |
| Distance to cuff (μm) | 628 (32-2678) |

TABLE 3

Quantitative data on dissection parameters concerning the loop(s) of each cadaver, followed by the average value.

| | Cadaver. | | | | | | | |
|---|---|---|---|---|---|---|---|---|
| | III | IV | | VII | VIII | IX | X | Average |
| Loop number. | 1 | 1 | 2 | 3 | 1 | 1 | 2 | — | 1 | 1.34 (0.0-3.0) |
| Loop neck (cm) | 2.5 | 1.5 | 1.1 | 2.3 | 2.0 | 2.0 | 1.5 | — | 3.0 | 1.99 (1.1-3.0) |
| Distance loop to origin SA (cm) | 2.5 | 5.0 | 8.5 | 12.5 | 8.0 | 3.2 | 7.1 | — | 5.0 | 6.48 (2.5-12.5) |
| Distance loop to spleen (cm) | 5.0 | 8.5 | 6.5 | 1.5 | 2.0 | 6.2 | 2.5 | — | 2.5 | 4.34 (1.5-8.5) |
| Loop height (cm) | 1.0 | 1.0 | 1.0 | 1.8 | 1.7 | 1.5 | 1.3 | — | 1.0 | 1.29 (1.0-1.8) |
| Diameter SA before loop (cm) | 0.5 | 0.5 | 0.5 | 0.4 | 0.6 | 0.4 | 0.4 | — | 0.4 | 0.46 (0.4-0.6) |
| Diameter SA first leg loop (cm) | 0.5 | 0.5 | 0.5 | 0.4 | 0.5 | 0.4 | 0.4 | — | 0.3 | 0.44 (0.3-0.5) |
| Diameter SA second leg loop (cm) | 0.5 | 0.5 | 0.5 | 0.4 | 0.5 | 0.4 | 0.3 | — | 0.3 | 0.43 (0.3-0.5) |
| Diameter SA after loop (cm) | 0.5 | 0.5 | 0.4 | 0.4 | 0.5 | 0.4 | 0.3 | — | 0.3 | 0.41 (0.3-0.5) |

In general, total PGP-IR (general nervous tissue) and TH-IR (sympathetic neural tissue) staining was comparable in nervous bundles surrounding splenic arterial loops. There was minimal staining of CGRP-IR (afferent nervous tissue). A sample of the total area of PGP-IR, TH-IR, and CGRP-IR nervous tissue calculated for three samples obtained from separate cadavers in shown in Table 5.

TABLE 5

Results first image analysis performed on three sample locations of the splenic loop of different cadavers, comparing the amount (and percentage) of PGP-IR, TH-IR, and CGRP-IR nervous tissue.

|  | Cadaver III (A5) | Cadaver IV (A5) | Cadaver VII (A5) |
| --- | --- | --- | --- |
| Total area PGP-IR nervous tissue ($\mu m^2$) | 247505 | 192682 | 530856 |
| Total area TH-IR nervous tissue ($\mu m^2$) | 301675 (121.89%) | 171133 (88.82%) | 516263 (97.25%) |
| Total area CGRP-IR nervous tissue ($\mu m^2$) | 1.581 (0.64%) | 3692 (1.92%) | 4354 (0.82%) |

Discussion

The analysis performed here shows that the splenic arterial loop is a commonly observed feature of the splenic artery. The loops are generally characterized by have a separating distance from the surface of the spleen to the inside curvature of the splenic artery of about 1 cm. This separating distance makes these sites useful targets for the surgical implantation of neural stimulation systems for neuromodulation of the splenic arterial nerve. The splenic arterial loops are more accessible, and carry less risk associated with surgical-induced trauma, by negating the need to excise the splenic artery from the surface of the pancreas.

Study 2: Electrical Stimulation of the Splenic Arterial Nerve

Materials and Methods

A total of 8 pigs (body weight between 40-50 Kg) were used for the histological and electrophysiological characterization of the splenic nerve.

On the experimental day, the animal was sedated with ketamine (1.5 mg/kg) and midazolam (0.5 mg/kg) administered by intramuscular injection. An intravenous catheter was placed in one auricular vein, and anesthesia was induced by propofol (2 mg/Kg) administered intravenously. An endotracheal tube was placed, and anesthesia was maintained with sevoflurane inhalant combined with continuous rate infusion (CRI) of fentanyl (0.2 μg/Kg/min).

After induction of general anesthesia, the animal was positioned in dorsal recumbency for placement of bilateral indwelling jugular vein catheters and one femoral arterial catheter under ultrasonographic guidance. Animals undergoing SpN cuff implantation were then repositioned into right lateral recumbency.

The surgical approach to SpN cuff implantation was as follows. The thoracolumbar junction was supported and slightly elevated using a sand bag. After appropriate surgical preparation (clipping and aseptic scrub with chlorhexidine gluconate and alcohol), the left flank was aseptically draped exposing a 20×25 cm area centered on the second to last rib. A 15 cm skin incision was made in the second to last intercostal space using monopolar electrocautery. The incision was continued through the subcutaneous tissues and intercostal musculature until the peritoneum was exposed. Two Finochietto rib retractors were placed retroperitoneal, taking care to engage the ribs. Over the next few minutes, the retractors were gradually opened, resulting in exposure of the left lateral abdomen measuring approximately 10×8 cm. The retractor blades were covered with gauze sponges soaked in carboxymethyl cellulose (CMC). The peritoneum was longitudinally incised and sutured to the skin (Vicryl 2-0; Ford interlocking suture pattern) covering the retractors blades in order to minimize risk of splenic tears during handling. Using careful digital manipulation, the spleen was exteriorized and the splenic artery (SpA) was identified along its visceral surface. At the mid portion of the spleen, proximal to the SpA branching into the left gastroepiploic artery, a short segment of the SpA was carefully dissected free of surrounding soft tissue for placement of a 1 mm ultrasonic flow probe (Transonic). After probe placement, the spleen was repositioned into the abdomen.

By slight rotation of the splenic visceral base towards the operator, and placing gentle ventral traction on the spleen, the gastrosplenic ligament at the splenic hilum was incised using Metzembaum scissors, exposing the SpA. The artery was followed in a dorsal direction to its origin (i.e. the bifurcation of the celiac artery into the left gastric artery (LGA) and the SpA). Immediately distal to this bifurcation, an approximately 1 cm segment of the SpA with the peri-arterial SpN network intact, was circumferentially isolated by blunt dissection using Metzenbaum scissors. A curved Mixter artery forceps was inserted under the artery from caudal to cranial, grasping one flap of the 2.5 mm diameter CorTec cuff introduced into the surgical field using straight Microdissection forceps. The cuff was placed around the SpA and the intact peri-arterial SpN network by reversing the motion of the Mixter forceps, taking care to appose the two flaps of the cuff when properly placed. The tension on the spleen and artery was then released. SpA and SpV (splenic vein) blood flow readings were tested and finally the rib retractors were partially closed and the exposed incision covered with saline-soaked gauze sponges.

Electrophysiological experiments were also carried out. These generally entailed dissecting and cuffing (using a 500 μm diameter bipolar or tripolar CorTec cuff) one or several discrete SpN fascicles few centimeters distal (closer to the spleen) to the stimulating cuff to enable evoked compound action potential (eCAP) recording during stimulation of the whole SpN plexus or of few fascicles (see FIGS. 5A-5E). Also, different combinations of blocking neural signaling (e.g. using topical administration of local anesthesia, or transection of the SpN fascicle) either upstream or downstream of the stimulation site were performed.

Recorded eCAP were amplified and filtered (100-1000 Hz) using an 1800 2-Channel Microelectrode AC Amplifier (A-M system). Nerve activity was monitored continuously using an oscilloscope and recorded to a computer using a 16 channels PowerLab (AD Instruments) acquisition system and LabChart 8 software using a sampling rate of 20 kHz. eCAP were generally averaged (8 pulses) and peak to peak or area under the curve (AUC) of the averaged response quantified. The conduction velocity of the eCAP components of the SpN were calculated from the distance between stimulation and recording site and the latency of the eCAP signal.

Electrocardiogram (ECG), Heart rate (HR), arterial blood pressure, respiratory rate (RR), pulse oximetry, capnography, spirometry were monitored throughout the surgery. Body temperature was recorded continuously with an intranasal probe. Arterial blood gasses were analyzed throughout the experiment to monitor pH, Glucose, pO2 and pCO2, K+ levels. All physiological parameters as well as the level of used sevoflurane were recorded (every 5-10 minutes) on the record sheet. Physiological data were also digitalized using Powerlab acquisition system and LabChart software. All parameters were generally sampled at a frequency between 0.1 and 2 kHz.

The depth of anesthesia was assessed by palpebral reflex, corneal reflex, medioventral eye ball position, and jaw tone.

Moreover, physiological parameters as well as a bispectral index monitoring system (levels between 30 and 60) were used to adjust anesthetic levels. In some cases, boluses of propofol were used.

In some cases, intra-operative ultrasonography of the spleen was used for real-time monitoring of SpA blood flow changes during SpN stimulation. For this procedure, an intra-operative probe (il2L-RS linear intraoperative transducer 4-10 MHz, 29×10 mm footprint, 25 mm field of view; GE Vivid-i) was used.

SpA blood flow changes was assessed by color Doppler and continuous wave spectral tracing. After color Doppler identification of the SpA within the splenic parenchyma 2-3 cm distal to the splenic hilum, continuous wave spectral tracing of the SpA flow was obtained by directing the windowing cursors to the center of the SpA lumen. After obtaining a representative signal, the ultrasonography probe and cursor window was left in position while SpN stimulation commenced.

All statistical analyses were performed with commercially available statistical software (IMP Pro 13.0.0 or GraphPad Prism 5.0).

Results

Figure 5A:
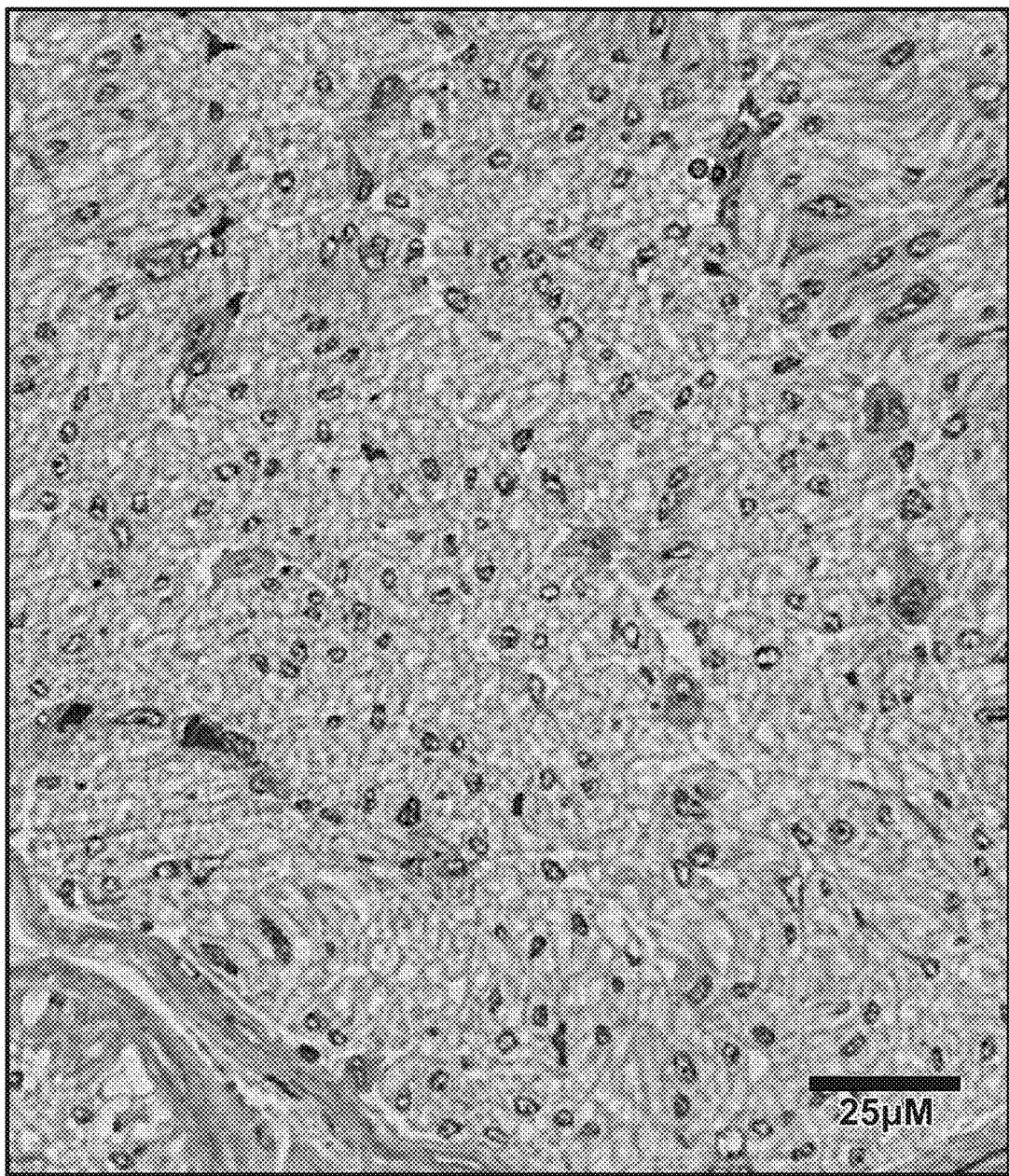
FIGS. 5A-5E show histological and electrophysiological characterization of a pig splenic nerve.
Figure 5C:
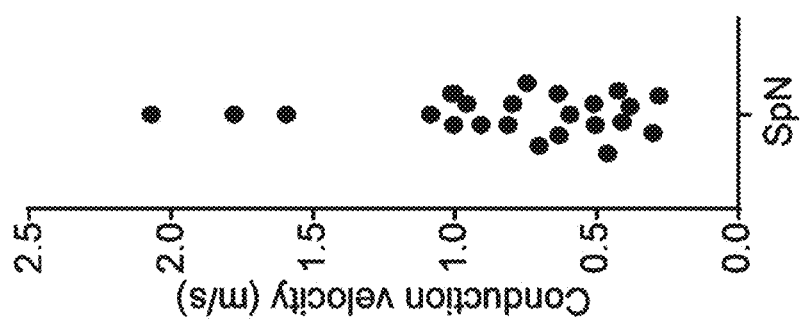
Figure 5B:
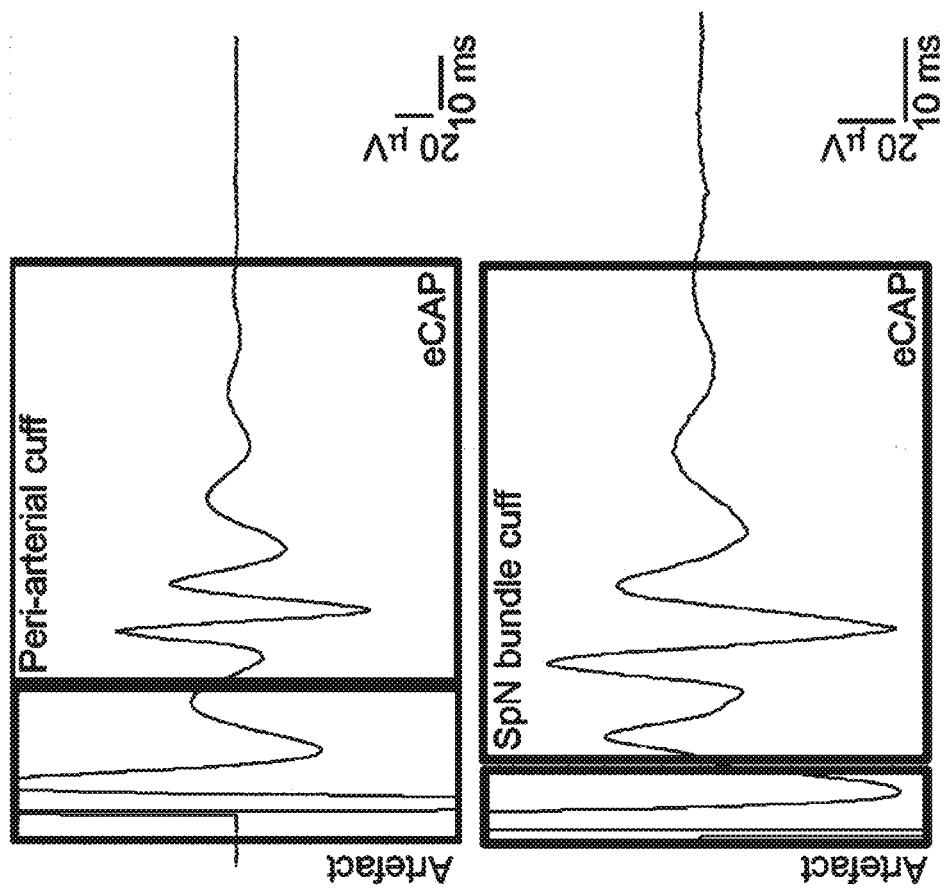
Figure 5D:
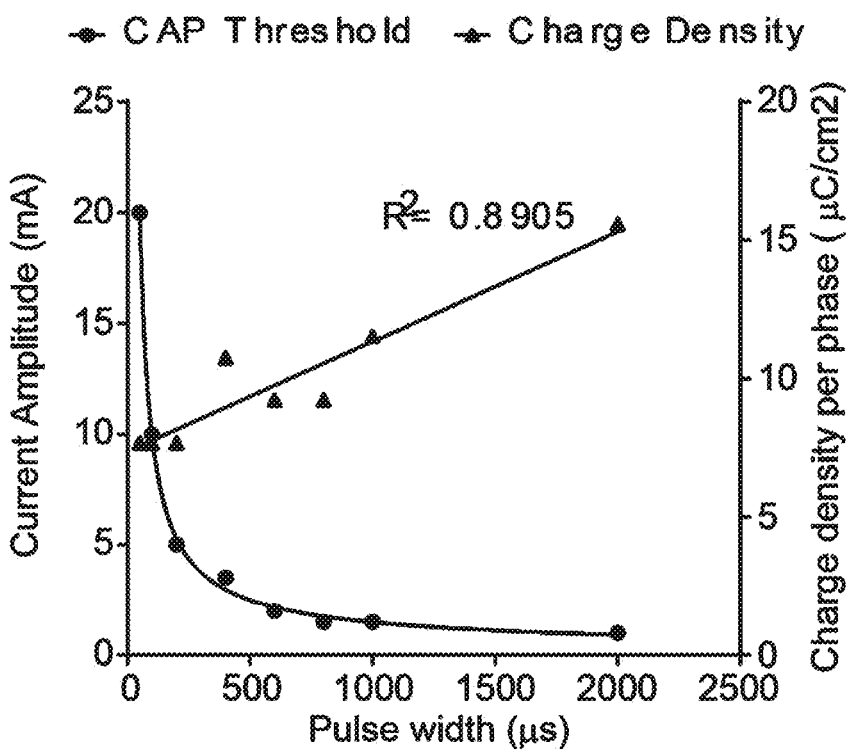
Figure 5E:
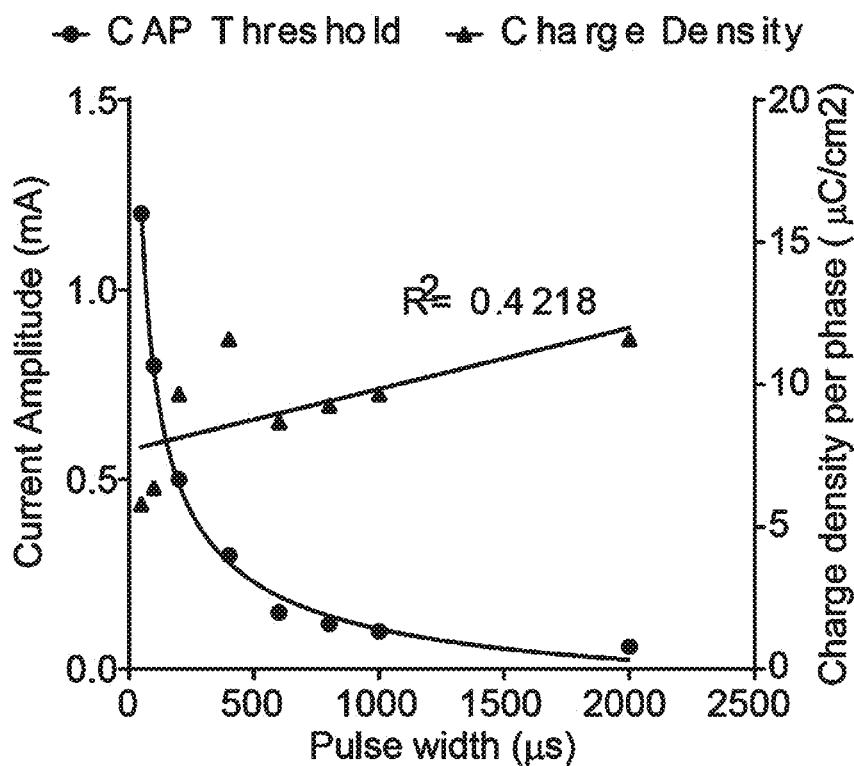

Recording of the eCAP generated during SpN stimulation, either of the whole SpN plexus with the peri-arterial cuff, or stimulation of few fascicles with a smaller cuff, generated an eCAP with a specific latency dependent on the distance between stimulating and recording sites (FIG. 5B). The range of conduction velocities of the different components of the eCAP is shown in FIG. 5C. The stimulation of either the whole plexus or few fascicles generated an eCAP with an average speed below 1 m/s (FIG. 5C). This conduction velocity is in line with histology findings in the characterization data below that describe the SpN being an unmyelinated nerve. The relationship between current amplitude and pulse duration necessary to elicit an eCAP either stimulating the whole plexus or few fascicles in shown in FIGS. 5D and 5E (respectively). When stimulating the whole plexus with a peri-arterial cuff the threshold of the nerve response was found between 7.692 and 15.58 $\mu C/cm^2$/phase. When stimulating few dissected fascicles with a smaller cuff the threshold was found to be between 5.796 and 11.594 $\mu C/cm^2$/phase. In both cases the threshold value of current density for eCAP recording was lower at shorter pulse width (PW).

Figure 6A:
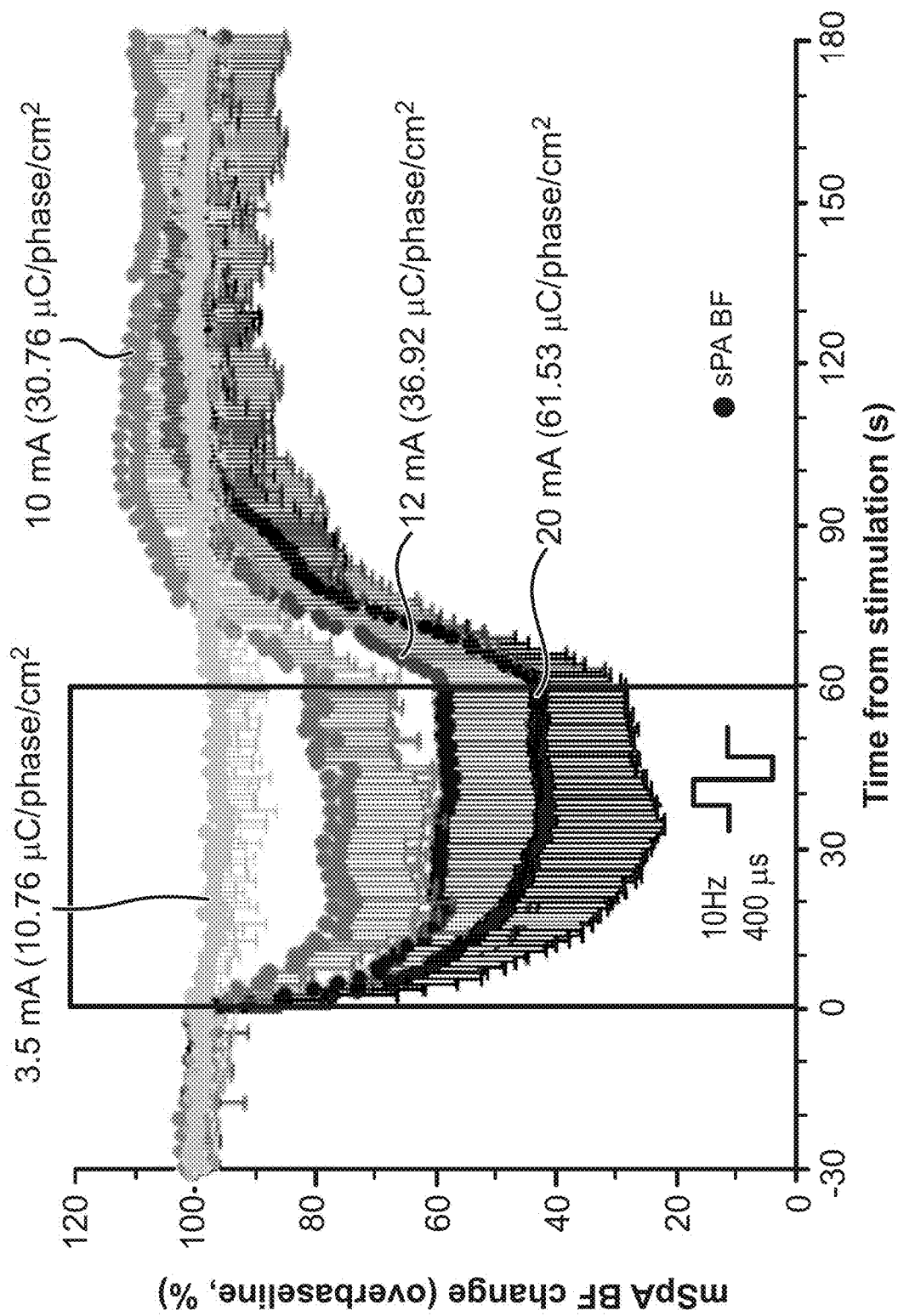
Figure 6B:
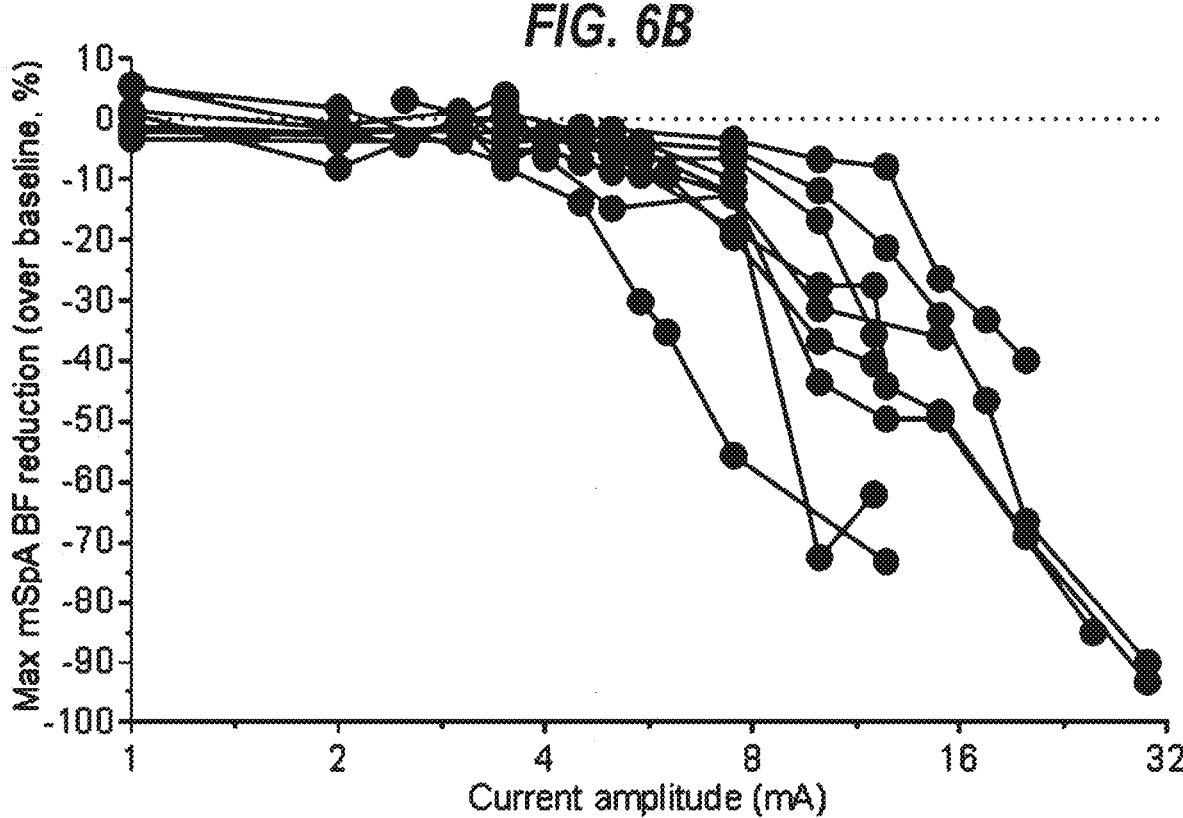
Figure 6C:
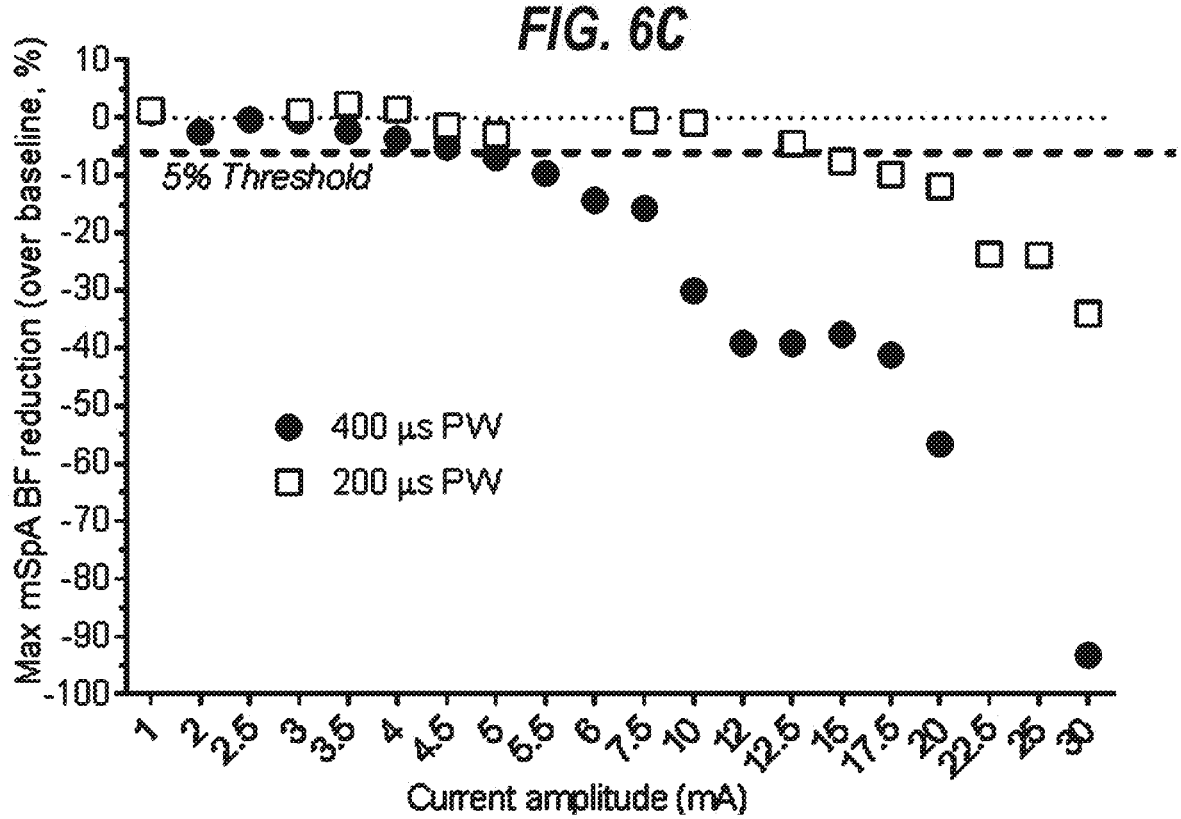
Figure 6D:
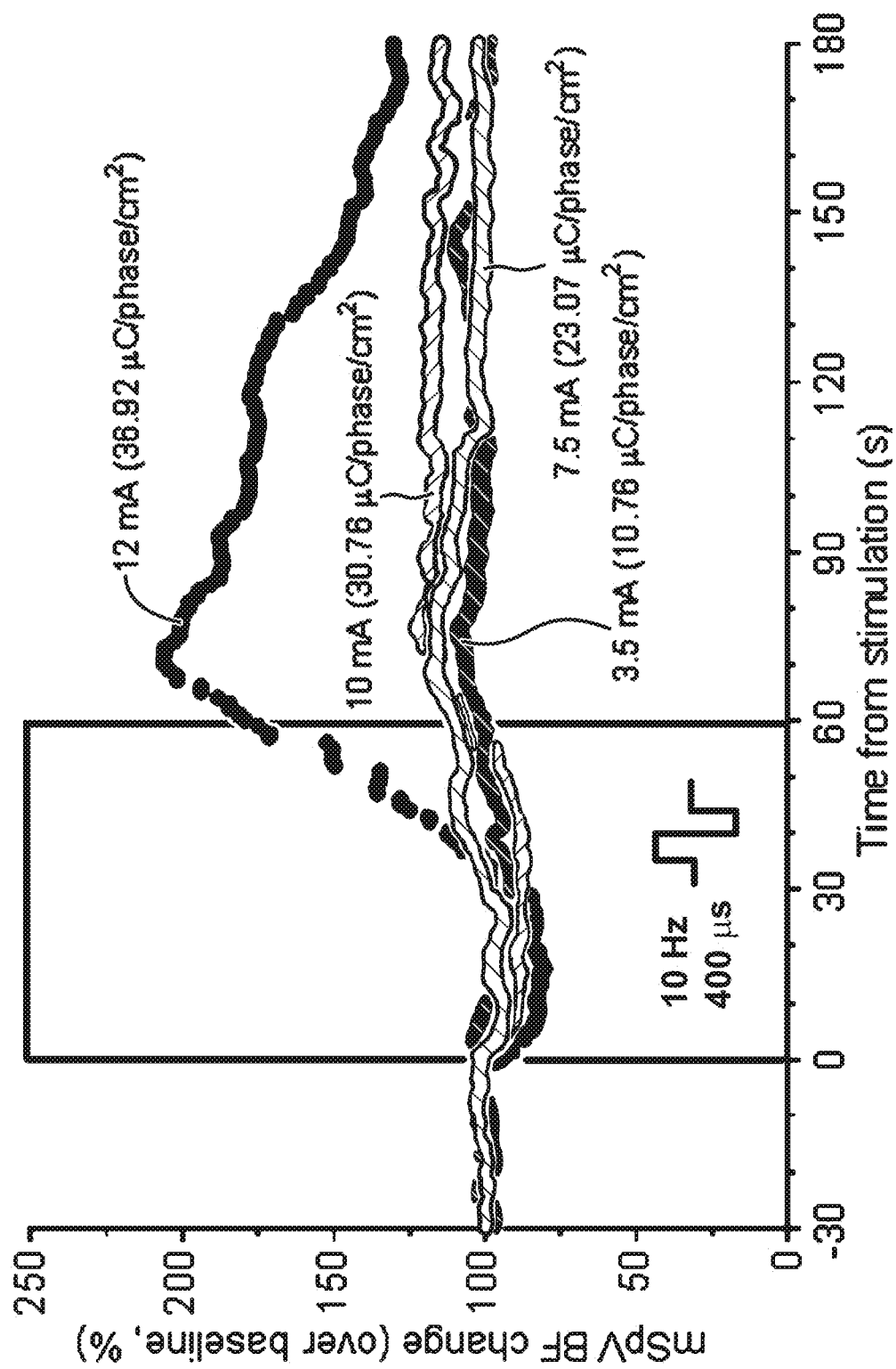

SpN biphasic stimulation for 1 minute at 10 Hz and 400 µs PW above a specific current threshold consistently caused transient blood flow reduction within the distal SpA as measured via a perivascular flow probe. There was a clear dose-response relationship between delivered current and flow reduction: the higher the amplitude the stronger was the observed reduction in blood flow (FIG. 6A). The blood flow change threshold, defined as a 5% change in mean SpA blood flow (mSpA BF) compared to pre-stimulation baseline, was observed around 4.5 mA (with a 400 µs PW) and around 12 mA (with 200 µs pulse width) (FIGS. 6B and 6C). When calculating the charge density per phase of the threshold to cause blood flow changes the value was very similar: about 13.8 $\mu C/cm^2$/phase at 400 µs and 18.46 $\mu C/cm^2$/phase at 200 µs. Stimulation with 12 mA and 400 µs PW (36.9 $\mu C/cm^2$/phase) caused a mean maximum BF reduction in the SpA of about 40% from baseline values.

In parallel, recording of the blood flow within the SpV was recorded by using a Doppler flow probe placed at the splenic base, where the vein leaves the splenic hilum. Interestingly, stimulation (symmetric biphasic pulses, 400, 10 Hz for 1 minute) caused an increase in mean SpV blood flow (mSpV BF) that was current amplitude dependent. Stimulation with 12 mA and 400 µs PW (36.9 $\mu C/cm^2$/phase) caused a maximum increase of about 200% when compared to baseline mSpV BF.

The transient reduction of mSpA BF was also accompanied by a transient increase in systemic mean arterial blood pressure (sMABP). This increase (in average between 1-6 mmHg) from baseline correlated again with the stimulation intensity (FIG. 6E). Consistent sMABP changes were observed with stimulations causing a 20-30% drop in the SpA flow. In contrast, HR was only minimally affected (<3 bpm changes, either increase or decrease), but more consistently only with high stimulation amplitudes (>45 $\mu C/cm^2$/phase causing 3-10 bpm changes) (FIG. 6G). SpN stimulation did not affect respiratory rate (RR) in the conditions tested.

Figure 6F:
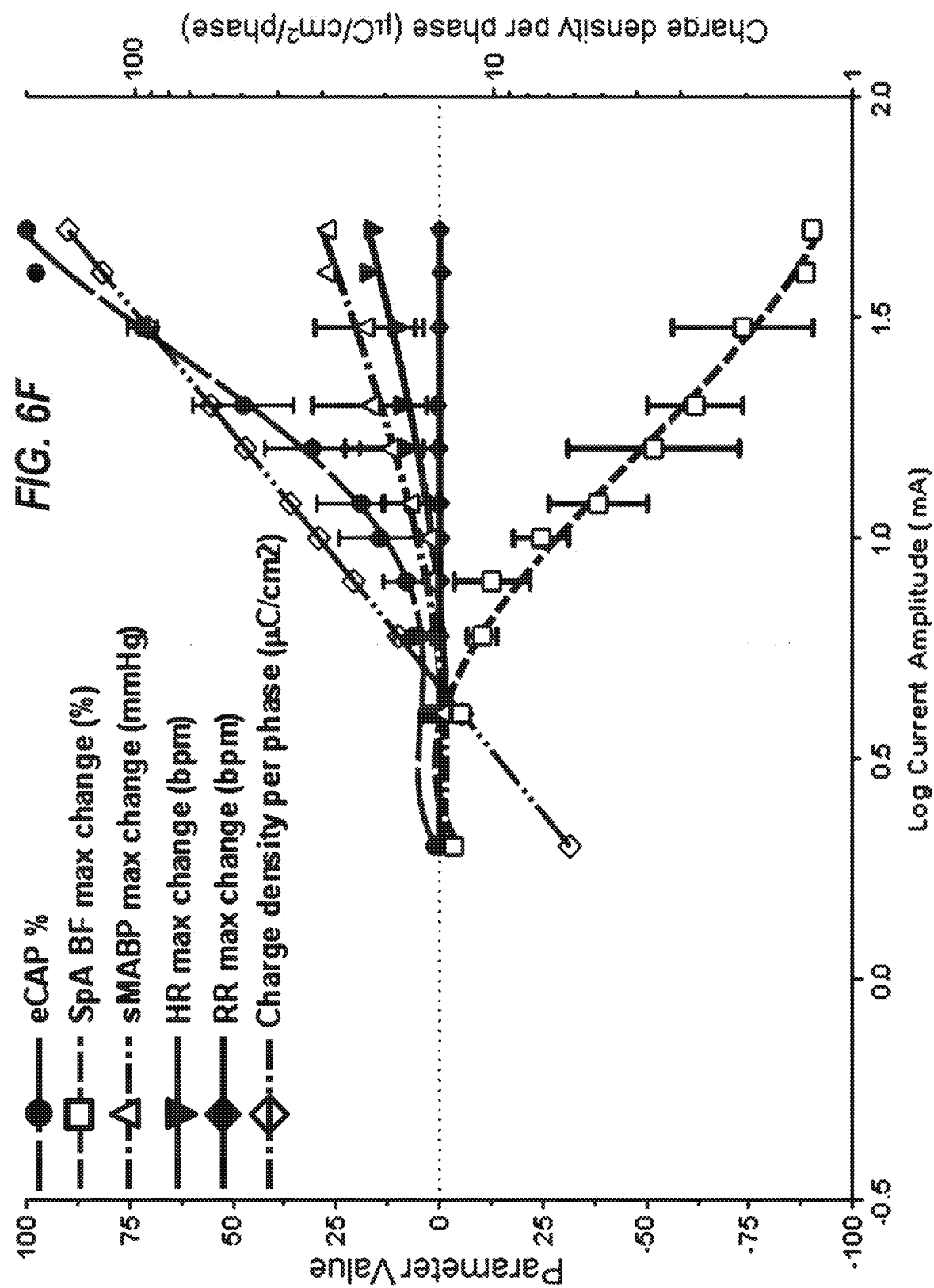
Figure 6G:
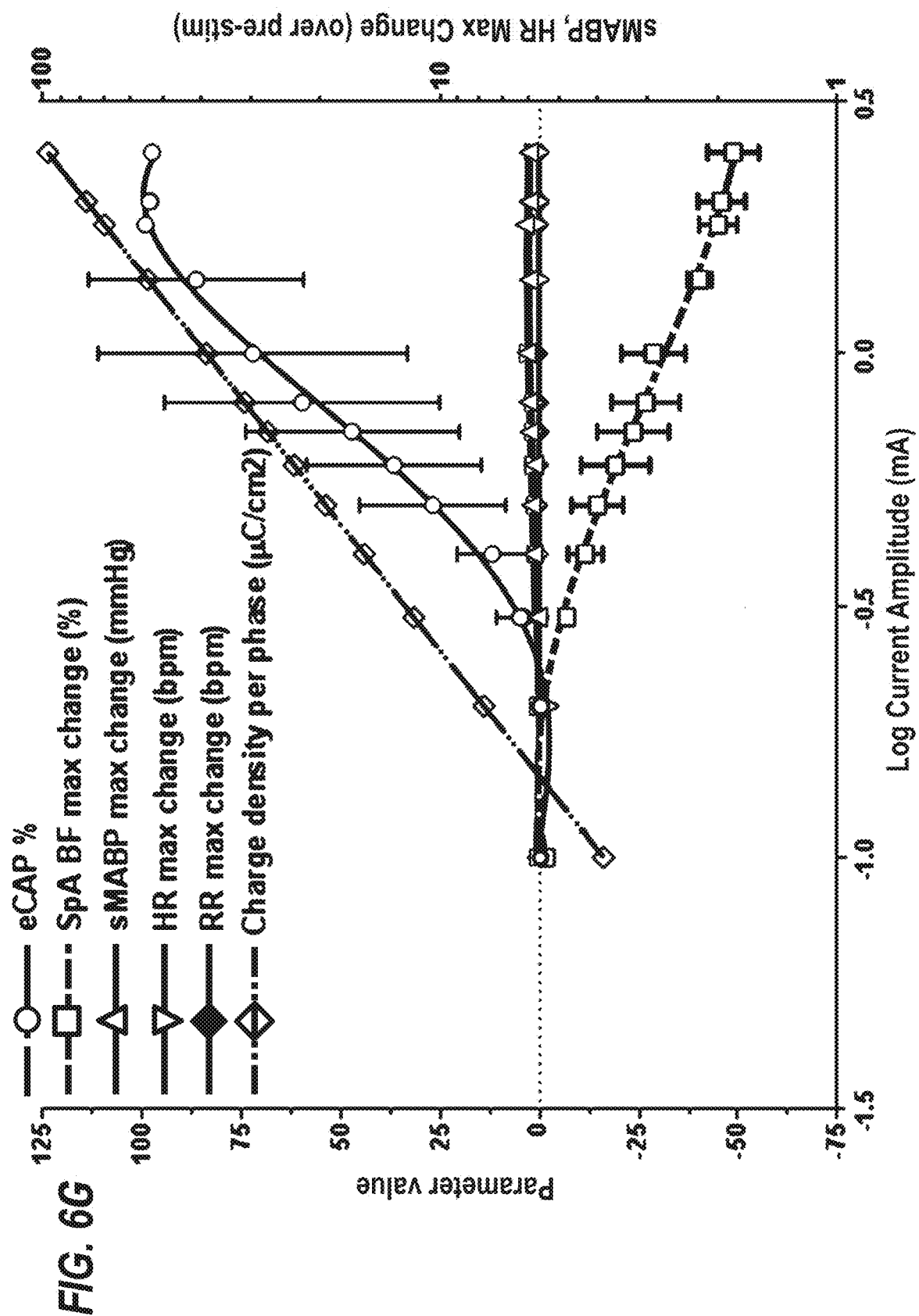

The changes observed in mSpA BF, sMABP, HR, RR during a 1-minute stimulation (symmetric biphasic pulses, 10 Hz, 400 µs PW) at different current amplitudes (1-50 mA, corresponding to 3.076-153.8 $\mu C/cm^2$/phase) are summarized in FIG. 6F. In FIG. 6F, it is possible to observe how the magnitude of these changes was correlated with the recording of an eCAP (black line and circles) from the SpN. The higher was the number of fibers recruited (measured as eCAP % over the maximum recorded response) the stronger was the reduction in mSpA BF and the other associated changes.

Direct stimulation of discrete SpN bundles dissected off the SpA (using a 500 µm diameter cuff, at location 'b' in FIG. 4A) evoked similar changes in the mSpA BF, sMABP and HR. These changes, occurring during a 1 minute (symmetric biphasic pulses, 1 Hz, 400 µs PW) and different current amplitudes (0.1-2.5 mA, corresponding to 3.86-96.61 $\mu C/cm^2$/phase), are summarized in FIG. 6G. Even in this case the associated changes were dependent on the proportion of fibers (eCAP shown in black) recruited by the stimulation. The maximum eCAP (and therefore maximum changes) was obtained at about 153 $\mu C/cm^2$/phase when stimulating the whole plexus and at about 70 $\mu C/cm^2$/phase.

The magnitude of the changes when stimulating few fascicles were lower than those obtained when stimulating the whole plexus, as expected since the total number of fibers stimulated was lower and the frequency was lower.

Figure 7A:
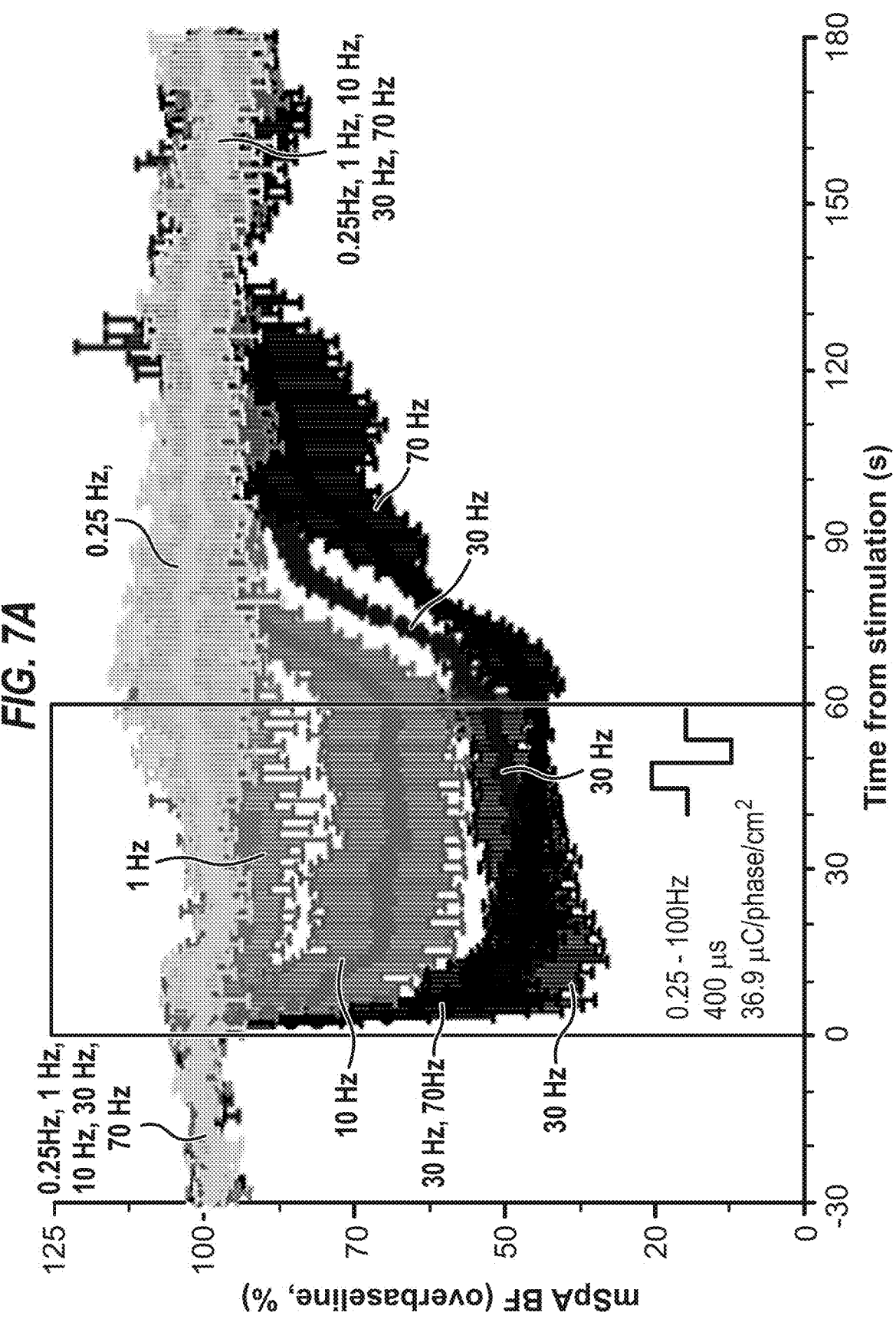
Figure 7B:
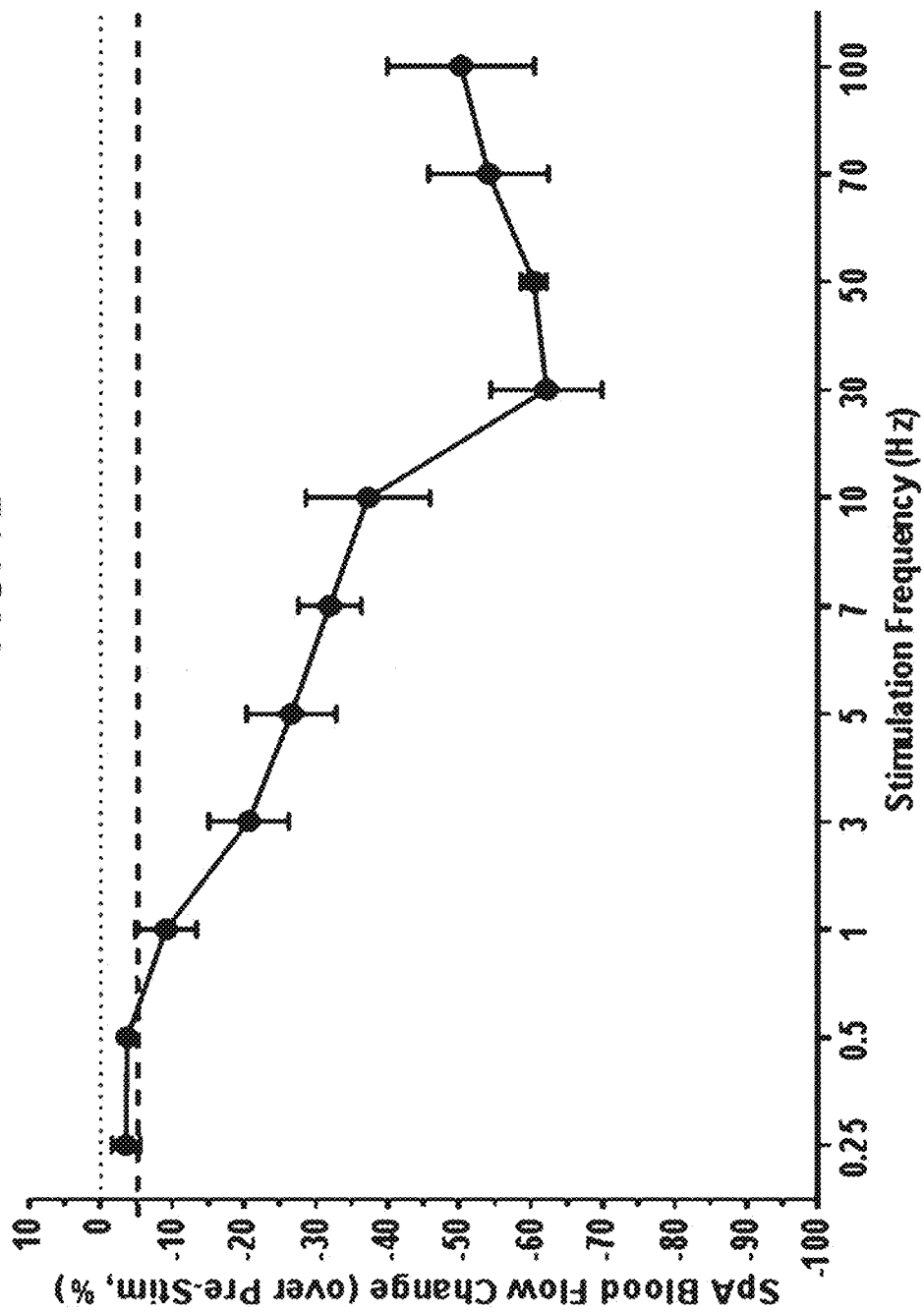
Figure 7C:
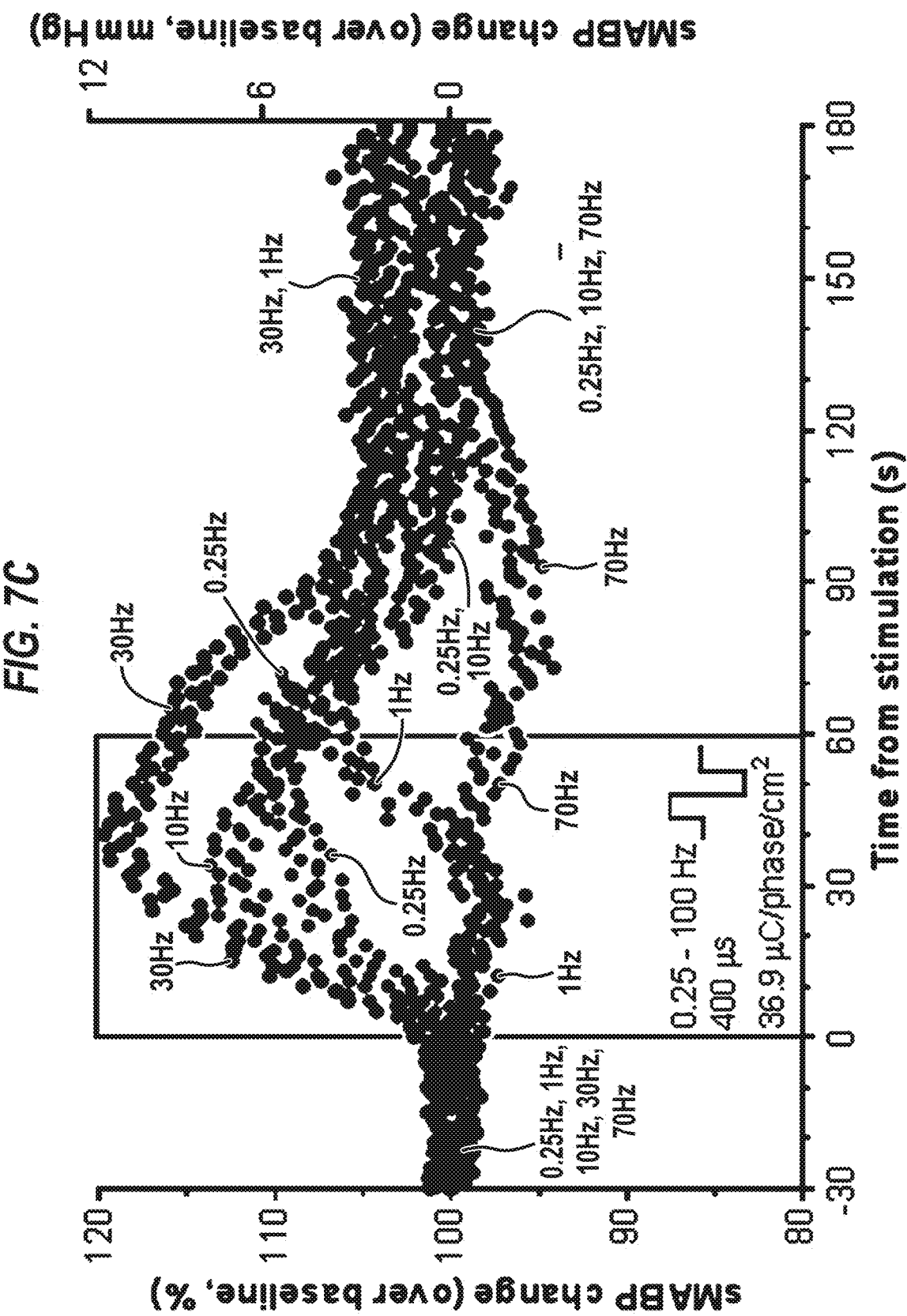

Blood flow changes in the mSpA were also affected by different frequencies of stimulation. When stimulating (symmetric biphasic pulses, 400 μs PW for 1 minute at about 36.9 μC/cm$^2$/phase) at different frequencies (between 0.25 and 100 Hz), 30-50 Hz reliably caused the strongest blood flow reduction in the SpA (FIG. 7A). Above 50 Hz (between 70 and 100 Hz) the reduction in BF was in fact smaller, in the range of reductions obtained with a 10 Hz stimulation (FIG. 7B). The changes in mSpV BF, sMABP and HR were also found to be dependent on the frequency of the stimulation applied. The strongest effects were again observed between 30 and 50 Hz (FIGS. 7C to 7D).

This was once again observed when maximally (around 70 μC/cm$^2$/phase) stimulating only few fascicles dissected off the artery. A stronger reduction in mSpA BF occurred already at lower frequencies (1 Hz and below), because of the higher recruitment of nerve fibers compared to the stimulation amplitude used for the whole plexus during the frequency analysis. Consistently however, the maximal reduction was observed between 30-50 Hz (FIG. 7D).

In order to further confirm that the observed changes in SpA BF were due to direct neuronal activation (rather than stimulation of smooth muscles) Lidocaine (2% lidocaine hydrochloride solution) was applied locally around the implanted SpN cuff (either the peri-arterial cuff or the cuff for dissected fascicles). Lidocaine is a specific blocker of fast voltage gated Na+ channels. Lidocaine was able to block the changes in SpA BF. Further, mechanical occlusion of the SpA, able to reduce the BF up to 80%, did not cause any change in sMABP or HR. In addition, transection of the central end of the SpN (proximal to the cuff) did not abolish stimulation effects on SpA blood flow, sMABP and HR. Also the transection of the SpN within the GEP and SG segments did not prevent these changes. Interestingly, all these effects were only abolished when the peripheral end of the SpN (distal to the cuff) was cut. All these data suggest that the changes in SpA BF and SpV BF were neuronal driven and related to the constriction of the SpA as well as the contraction of the spleen capsule. On the other hand, the changes in sMABP and HR were probably not due to the activation of a neuronal pathway towards the brain but to the increase outflow of blood from the spleen towards the heart.

Figure 8:
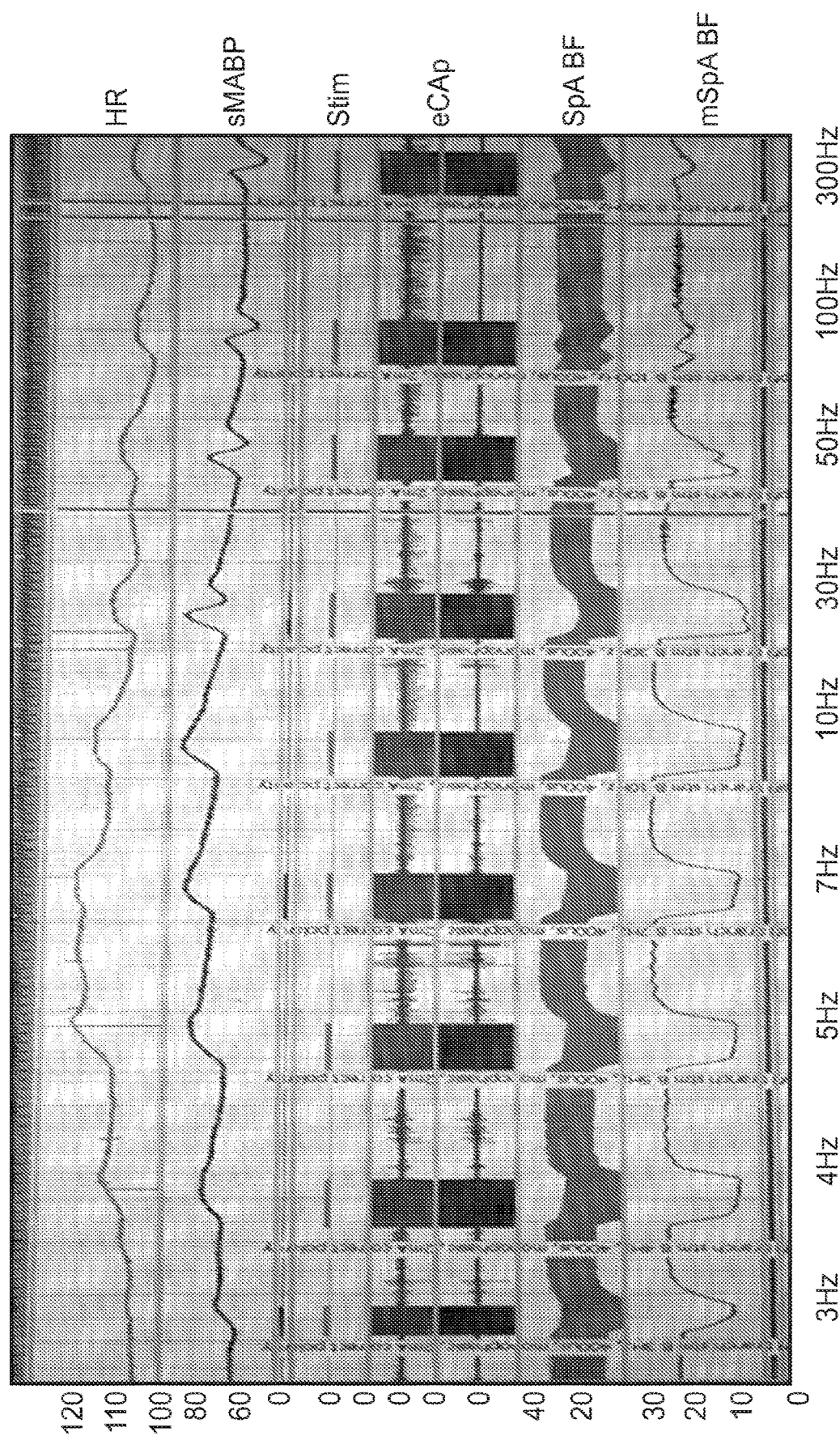
FIG. 8 shows local and systemic effects of few dissected SpN fascicles at different frequencies. In particular.
Figure 9:
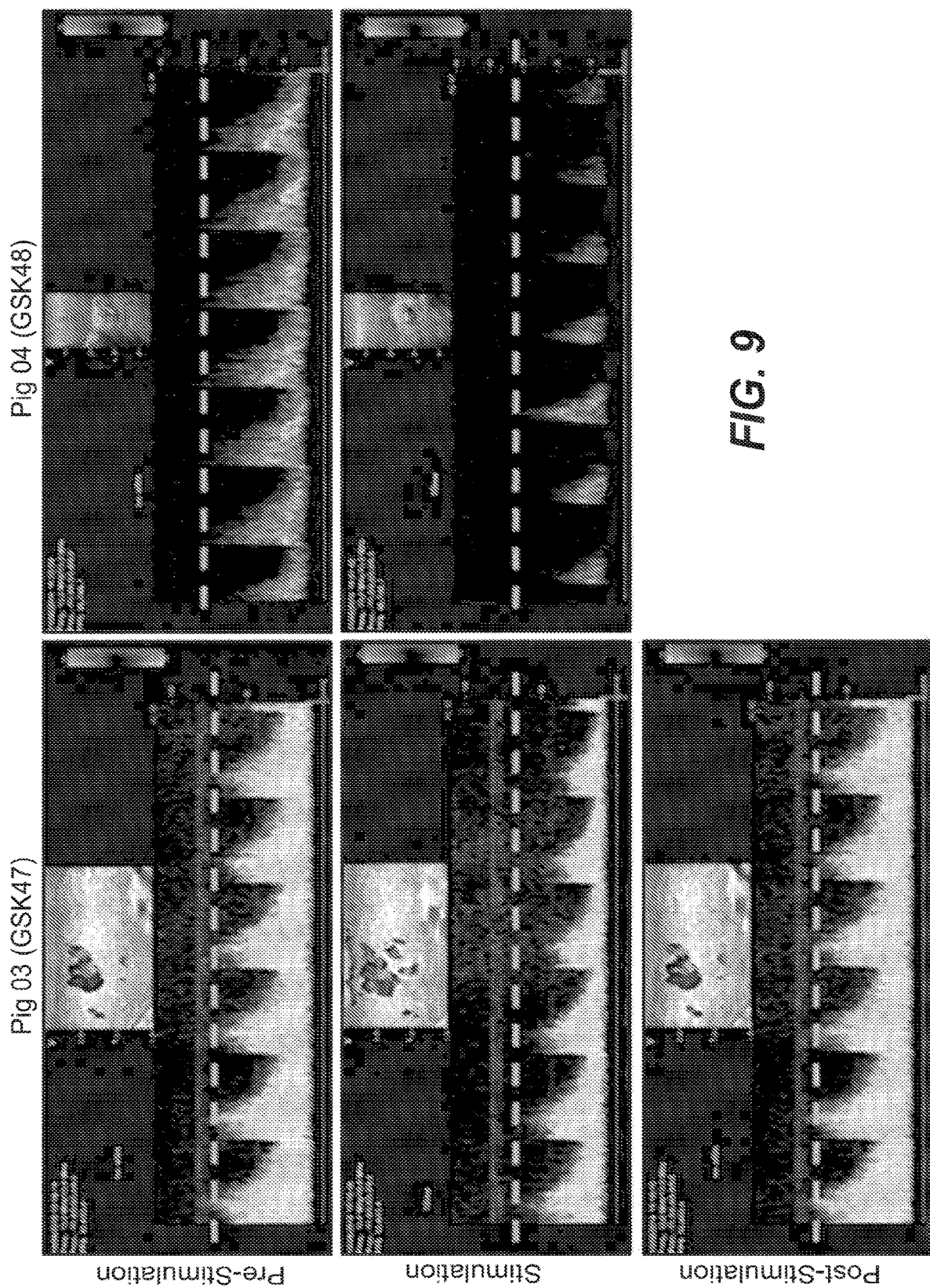
FIG. 9 shows SpA blood flow changes monitored via intra-operative splenic ultrasonography. The images of FIG. 9 were obtained from 2 different animals during SpN stimulation. Note the reduced Doppler trace during stimulation (middle panels) versus pre-stimulation and post-stimulation (top- and bottom-panels, respectively).

In few animals, SpA blood flow changes during stimulation was also monitored using intra-operative ultrasonography at the splenic hilum. After identifying the SpA by color Doppler, the change in BF was monitored by Doppler signal as shown in FIG. 8. During stimulation at 10 Hz, a reduction in BF could be easily observed as indicated by the changed amplitude and shape of the flow traces.

Discussion

Splenic nerve stimulation was associated with transient local changes in mSpA BF and mSpV BF as well as splenic contraction. These changes were due to the direct activation of the SpN, rather than direct stimulation of the smooth muscles of the SpA. Spleen contraction during SpN stimulation has been previously reported also in other species [16]. The observed change in mSpA BF was very consistent between animals. The variation was probably mainly due to different fitting of the cuff around the SpN plexus in different animals. Changes in SpA BF could be easily monitored via non-invasive ultrasound and therefore could be used as a marker to assess effective stimulation of the SpN also in a clinical setting.

The transient changes observed during SpN stimulation were shown to be amplitude and frequency dependent. During a minute of stimulation at different current amplitudes, the strongest mSpA BF reduction was observed at the highest current amplitude tested that also corresponded to the peak of the recorded eCAP. This was true when stimulating the whole SpN plexus (with a peri-arterial cuff) or when stimulating only few fascicles placed within a smaller cuff. The difference in the total charge density needed to obtain maximum eCAP from the SpN plexus and from SpN fascicles could be explained by the partial coverage of the plexus with the 2.5 mm cuff used. In most of the pigs in fact this cuff resulted only in a 270-300 degrees of circumferential coverage. When cuffing only few fascicles of the SpN dissected off the artery the coverage was almost total. Therefore, in order to limit charge density needed to obtain optimal recruitment of SpN fascicles, optimal circumferential coverage of the artery will be needed.

The strongest changes (in mSpA BF and sMABP) were observed at frequency between 30 and 50 Hz. Although the total number of pulses delivered could be an important factor in determining the magnitude of this changes, it is true that when comparing changes occurring with the same number of pulses delivered at different frequencies, 30-50 Hz range still caused the strongest changes. This could be explained with previously reported data showing that maximum release of NA from the cat spleen was observed at 30 Hz [17,18]. Higher release of NA could explain the higher magnitude of the changes observed in this stimulation range.

Study 3: Effects of Electrostimulation in In Vivo LPS Animal Model

Materials and Methods

Animals

A total of 18 pigs (over the initial 38) (age/weight) were used for this section of the study. None of these 18 pigs were excluded from the analysis.

General Design

Three hours after the initial stimulations performed as part of another study aim, 18 animals received an intravenous injection of 2.5 μg/kg endotoxin (Purified lipopolysaccharides from the cell membrane of *Escherichia coli* O111:B4; Sigma Aldrich), administered over a period of 5 minutes. This dose was selected through a thorough review of the available literature and personal experiences. This dose was chosen to cause a septic shock-type of model. Animals which received SpN stimulation 3 hours prior to LPS injection were divided in 2 groups: the SpNS did not receive any further stimulation whereas the SpN2S received a second SpN stimulation during the LPS injection.

The stimulation parameters include a 1 minute duration, with square, biphasic, charge balanced symmetrical pulses at 10 Hz, with a 400 μs pulse duration and a current amplitude corresponding to a charge density per phase of 30 to 90 μC/Cm$^2$/phase. The stimulation was applied once and then repeated a second time 3 hours later at the time where LPS was injected in vivo.

Peripheral venous blood was collected immediately prior to LPS injection (baseline), and then every half hour up to 2 hours post injection. At the end of this time-window pigs were euthanized or used for further final electrophysiological tests. For all of these time points, cytokine analysis (TNFα and IL-6), and routine hematology and biochemistry analyses were performed. Serum was diluted 1:10 for the cytokine analyses.

In animals where the LPS injection caused clinical changes in systemic blood pressure and/or cardiac function, standard clinical therapies such as vasopressin (2.5 IU bolus injections administered i.v. and repeated as needed) and anti-arrhythmic drugs (lidocaine; 2 mg/kg i.v. and/or atropine; 40 μg/kg; i.v.) were given at the discretion of the anesthetist. Animals were euthanized when mean systemic arterial pressure could not be maintained >40 mm Hg, or when the animal completed the pre-determined endpoint.

Statistical Analyses

All analyses were performed with commercially available statistical software (JMP Pro 13.0.0). Continuous variables were visually inspected for normality and outliers. When outliers were identified, statistical tests were performed including and excluding these animals as stated in the result section.

Changes in cytokine and leukocyte levels were calculated as the percentage of baseline samples collected immediately prior to LPS injection. Cytokine and leukocyte levels were subsequently analyzed using a mixed model with stimulation group, time and stimulation group*time as fixed effects, and animal as random effect. Pairwise Student's t-tests were used for Post Hoc analysis. Differences in survival time between stimulation groups was analyzed using the Log Rank test and plotted in a Kaplan Meier plot. Cytokine levels, leukocytes and electrolytes were compared between the different treatment groups at 30 minutes post LPS injection using a two-way ANOVA analysis with Post Hoc All Pairs Student's t-test analysis; this test was also used to compare maximal reduction in mean arterial blood pressure between groups. Statistical significance was defined as $P<0.05$.

Results

Survival

Administration of a high dose of LPS caused a rapid change in systemic arterial blood pressure within 5-10 minutes post LPS administration. In the sham (non-stimulated) animals these changes were stronger and more rapid. Many animals required interventions (e.g. injection of vasopressin) in order to maintain safe levels of blood pressure (mean ABP>40 mmHg). However, in most of the animals the intervention was not enough to restore safe levels of ABP and animals required euthanasia. In addition, few animals showed Tachyarrhythmia and severe tachycardia. Stimulated animals (especially those receiving 2 splenic nerve stimulations) showed lower magnitude changes and a more stable cardiovascular response. The events recorded after LPS administration in stimulate and sham animals are summarized in table 2.

Table 2 describes cardiovascular changes after LPS administration. The table shows the changes in mean arterial blood pressure (MABP) observed in the animals after LPS administration, and treatment administered to individual pigs. The time represent the time after LPS injection. MASS=external chest (cardiac) massage; VAS=administration of vasopressin (2.5 µg/kg i.v.); ATR=administration of atropine; LID=administration of lidocaine; Time Euth=time (minutes) from administration of the LPS to euthanasia; the pre-determined end-point was at 120 minutes.

TABLE 2

| Group | Pig# | Changes in MABP | Cardiac abnormalities | MASS | VAS | ATR | LID | Time Euth |
|---|---|---|---|---|---|---|---|---|
| Sham | 1 | Severe hypotension at 10 min | Severe tachycardia | 20 min | 20 min | | | 30 min |
| | 2 | Severe hypotension at 10 min | Severe tachycardia | 20 min | 10 min | | | 20 min |
| | 3 | Moderate hypotension at 20 min Severe hypotension at 80 min | Tachyarrhythmia | — | 20, 25, 30, 35, 40, 45, 50, 55 min | | | 80 min |
| | 4 | Severe hypotension at 10 min | — | — | 10 min | 20 min | 20 min | 30 min |
| | 5 | Severe hypotension at 10 min | Tachyarrhythmia | 20 min | 10, 20 min | 20 min | | 25 min |
| | 6 | Moderate hypotension at 90 min | Severe tachycardia | — | 90 min | | | 120 min |
| SpNS | 1 | Moderate hypotension at 100 min | Tachyarrhythmia | — | 100 min | | 100 | 120 min |
| | 2 | — | | — | — | — | — | 120 min |
| | 3 | Hypotension at 20 min | | — | 20 min | — | — | 120 min |
| | 4 | Severe Hypotension at 20 min | | — | 20 min | — | — | 30 min |
| | 5 | Severe Hypotension at 20 min | | — | 20 min | — | — | 40 min |
| | 6 | — | | — | — | — | — | 120 min |
| SpN2S | 1 | Moderate Hypotension at 20 min; Normotension at 60 min | — | — | 20, 30 min | — | — | 120 min |
| | 2 | — | — | — | — | — | — | 120 min |
| | 3 | — | — | — | — | — | — | 120 min |

TABLE 2-continued

| Group | Pig# | Changes in MABP | Cardiac abnormalities | MASS | VAS | ATR | LID | Time Euth |
|---|---|---|---|---|---|---|---|---|
| | 4 | — | — | | | | | 120 min |
| | 5 | Severe Hypotension at 20 min | Tachyarrhythmia | 30 min | 20 min | 30 min | 30 min | 40 min |
| | 6 | — | — | — | — | — | — | 120 min |

Figure 10A:
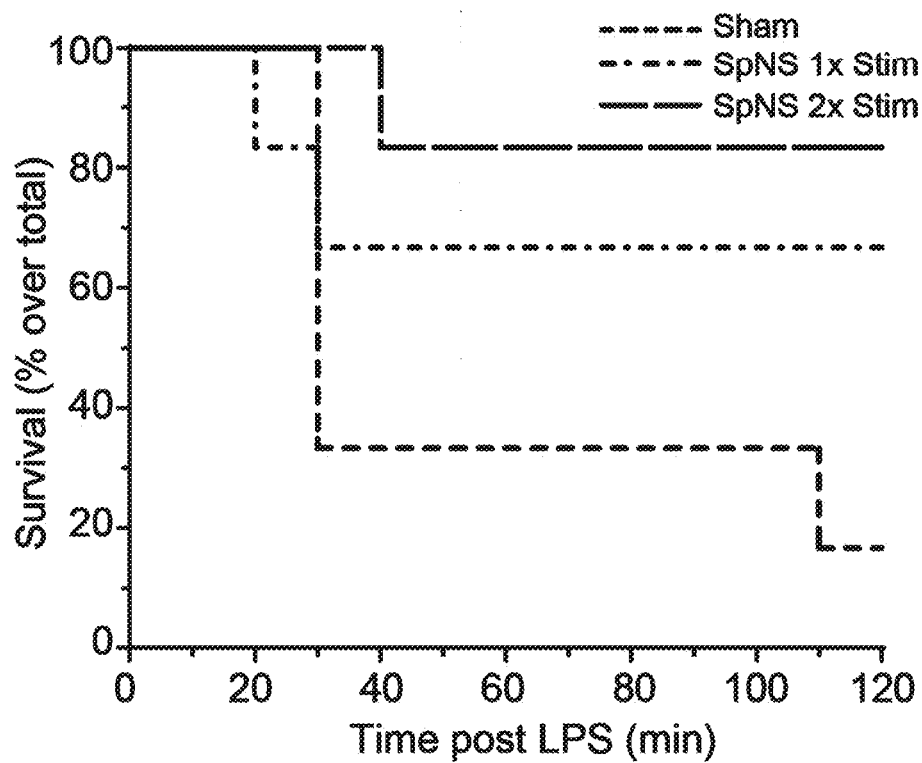
FIGS. 10A-10D show that SpN stimulation promoted survival.
Figure 10B:
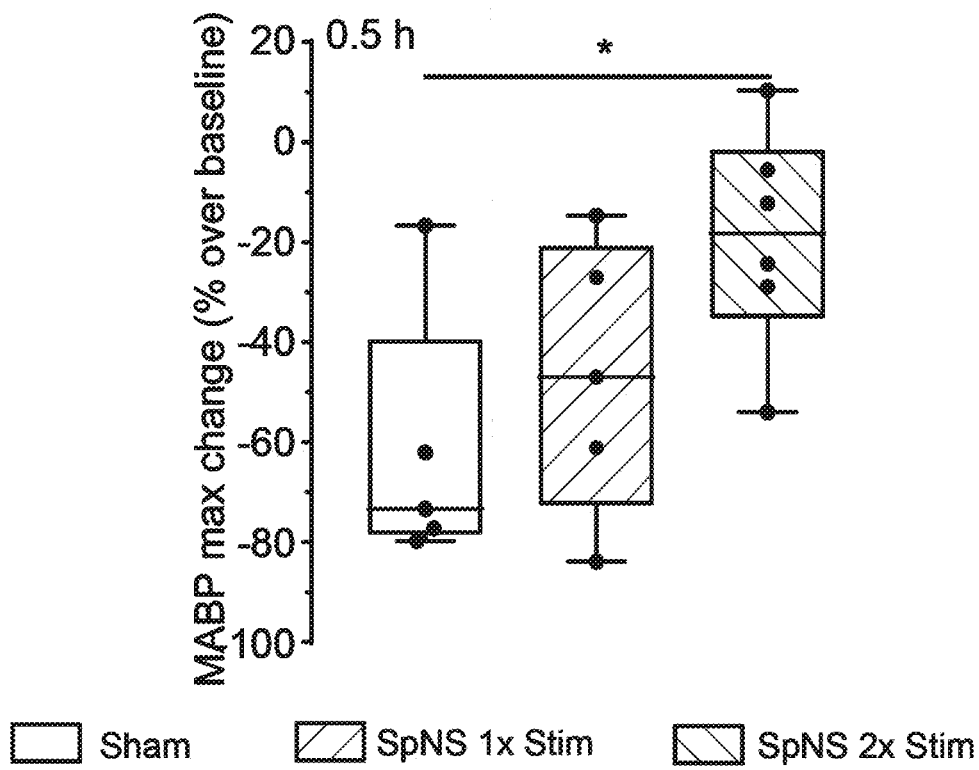
Figure 10C:
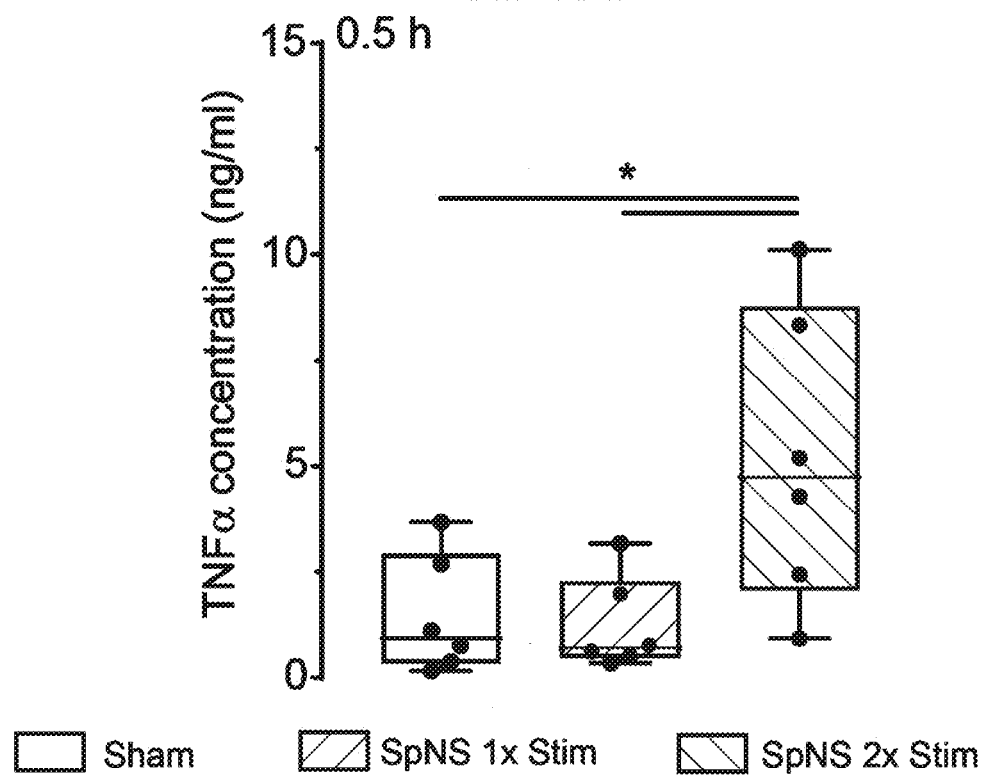
Figure 11A:
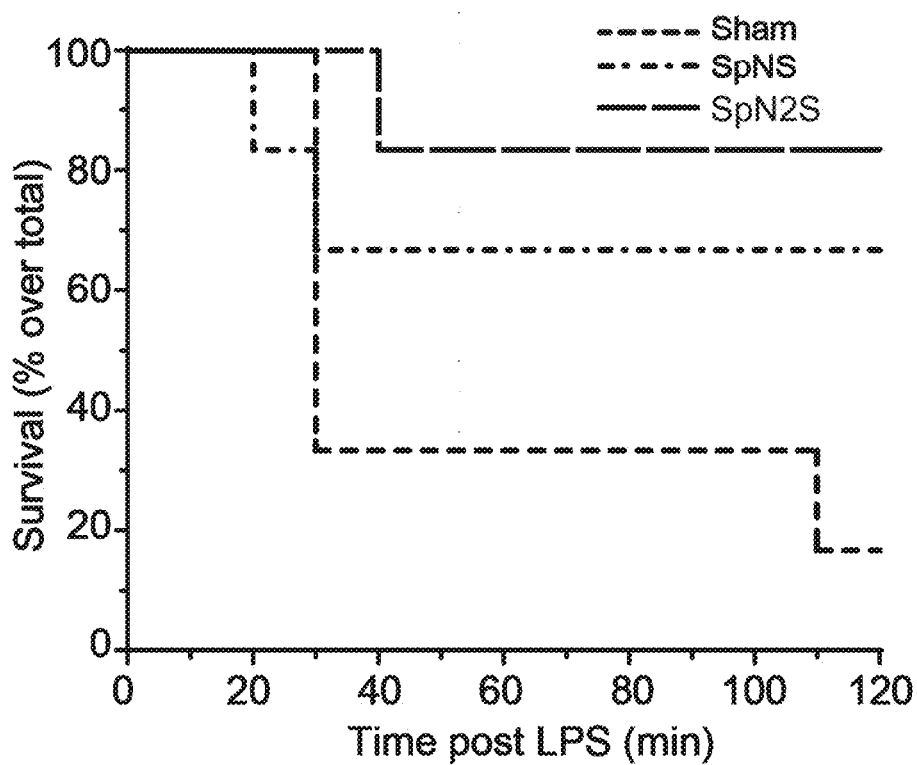
FIGS. 11A-11D show that SpN stimulation promoted survival in a similar manner to FIG. 10, but with additional data.
Figure 11B:
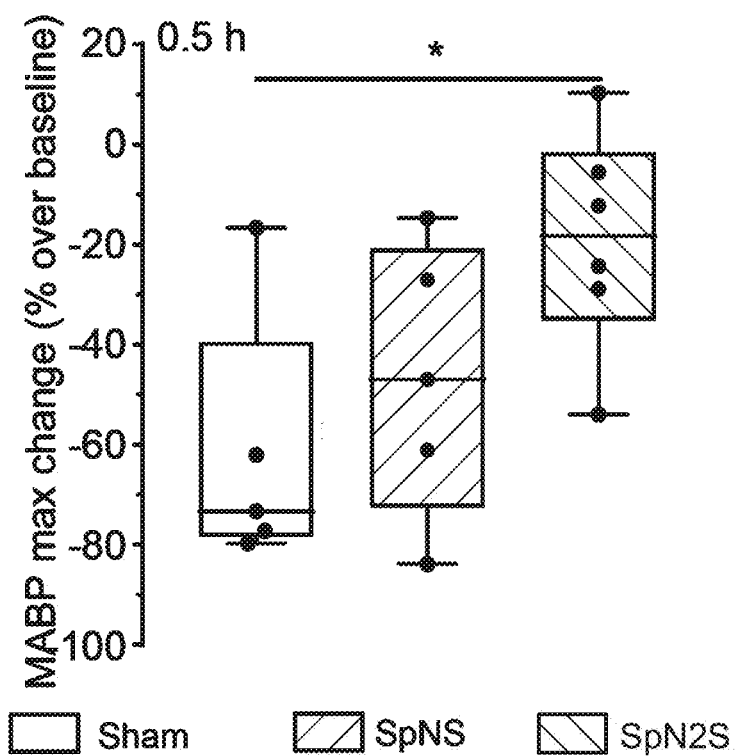

The 2 hours post injection survival rate is reported in FIG. 10A and FIG. 11A. There was a statistical significant difference in survival rate between the SpN-T vs. Sham (P=0.0194). In brief, LPS injection evoked severe cardiovascular compromise within 10-20 minutes in 5/6 sham animals, necessitating euthanasia (MAP≤40 mm Hg despite treatment) prior to reaching the pre-determined endpoint. Conversely, in 5/6 SpN-T stimulated animals, and 4/6 SpN-P stimulated animals, vital parameters including mean arterial blood pressure remained stable throughout the experiment period; for these groups, MAP at 2 hours post injection was 95.3±13.5, 85.9±7.5 and 86.8±9.7% of baseline values, respectively. Likewise, there was a statistically significant difference in maximal reduction in MAP between the SpN-T vs. Sham (P=0.0296, FIG. 10B and FIG. 11B); mean MAP at the time of euthanasia was 87.1±23.5% of baseline in the SpN-T group (mean survival time 1.8±0.5 hours post injection); 62.7±33.0% of baseline in the SpN-P group (mean survival time 1.4±0.8 hours post injection); and 48.6±37.9% of baseline in the Sham group (mean survival time 0.9±0.7 hours post injection).

Cytokine quantification: For all groups, LPS injection resulted in a significant increase in TNFα levels in all post-injection samples compared to baseline (P≤0.001; FIG. 10C to 10D and FIG. 11C to 11D), with the peak response observed at 1 hour post injection. IL-6 was significantly higher at 2 hours post injection compared to baseline across all groups (P≤0.0001).

Figure 10D:
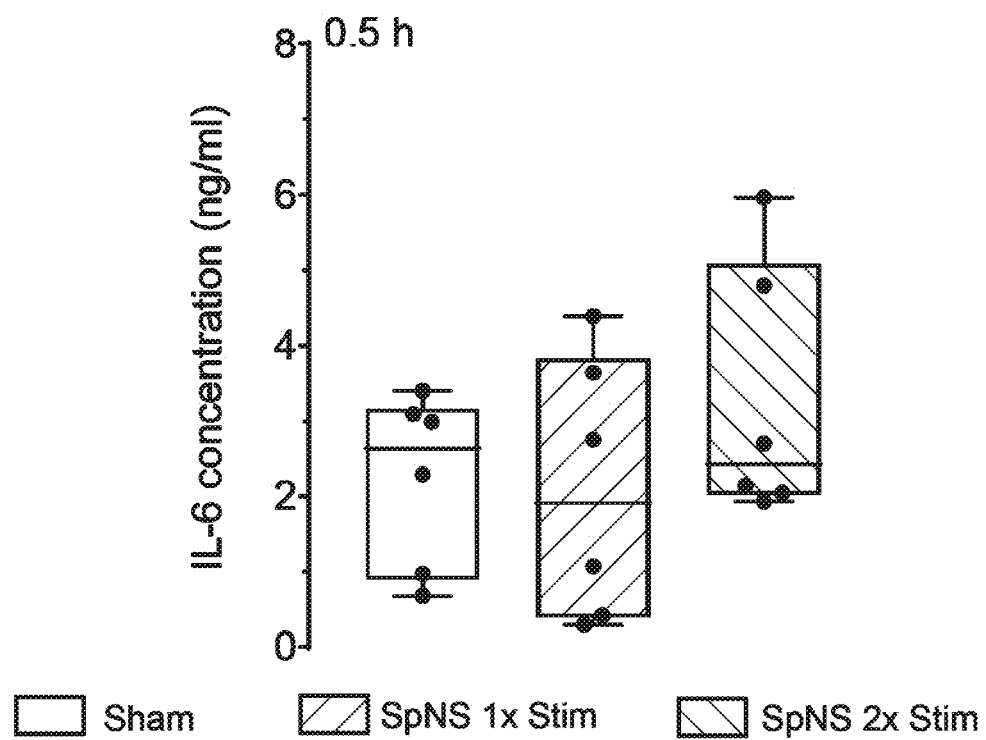
Figure 11C:
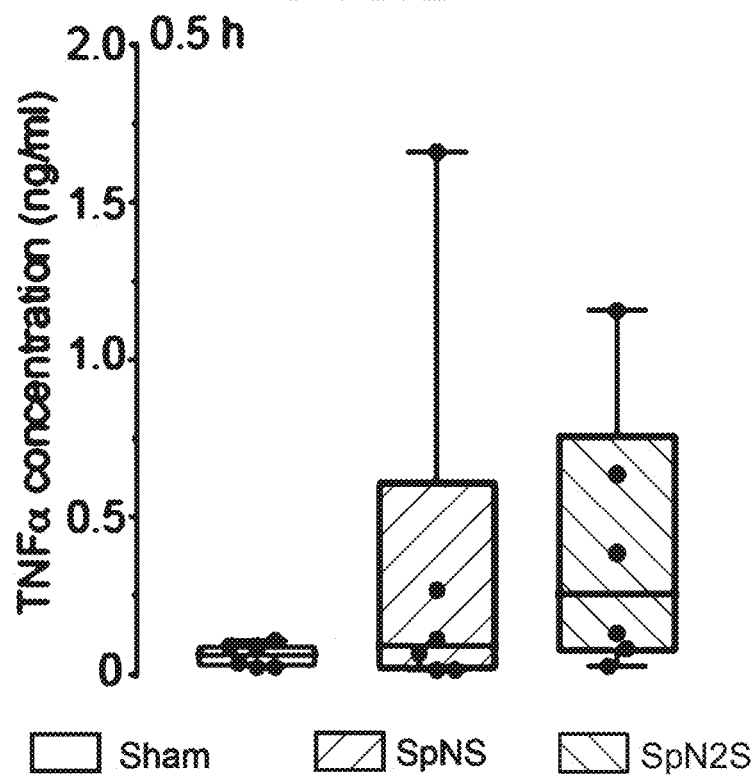
Figure 11D:
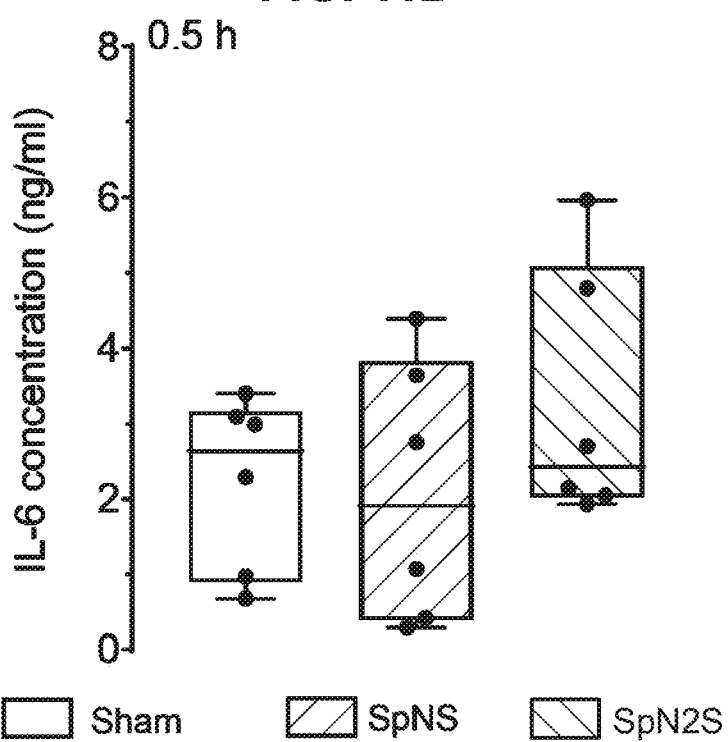

When comparing cytokine levels at 0.5 hours post injection, TNFα levels as well as IL-6 levels were not found significantly different between the sham and stimulated groups (FIGS. 10D, 11C and 11D).

Discussion

The administration of LPS in vivo to mimic an inflammatory response provided a good model to test the efficacy of SpN. The administration of LPS (2.5 µg/Kg of body weight) in 45-50 kg pigs caused upregulation of cytokines (TNFα and IL-6) in the blood of all the animals tested. In particular, TNFα reached a peak value of about 12 ng/ml at 1 h post injection while IL-6 picked around 15 ng/ml at 2 h post LPS. The LPS also caused significant changes in the peripheral blood composition, with reduction in circulating lymphocytes and neutrophils (results not shown). White blood cells in fact probably leaves the circulation to infiltrate tissues and organs during the systemic infection mimicked by the LPS. A significant increase in blood urea, creatinine and total bilirubin as well as an increase in CK and ALP over time was also observed after LPS (results not shown). All these changes indicated that the model was effective and reproducible between animals.

Strikingly sham animals showed a very rapid and strong decrease in systemic MABP, at about 10-15 minutes post LPS administration. Reductions in systemic MABP reached levels that would be rapidly life threatening, thus requiring the administration of vasopressin. However, in most of the controls this was not sufficient to stably restore a normal sMABP. Even when further injections of vasopressin were performed, 4/6 sham controls had to be euthanized at 30 minutes post LPS injection since their sMABP could not be kept above 40 mmHg. One of the sham was instead euthanized 110 minutes post LPS injection for the same reason. In some cases, arrhythmias were also observed.

On the opposite, most of the animals that were stimulated (at either −3 h or at −3 h and 0 h, relative to LPS) did not show such strong changes in sMABP. Most of them did not require any pharmacological intervention (i.e. vasopressin). This pro-survival effect of SpN stimulation, however, could not be explained by a lowering of the concentration of LPS-induced cytokines. TNFα and IL-6, in fact, measured at 30 minutes post LPS injection were not reduced in the stimulated animals when compared to sham animals. Therefore, even though this model provided the proof that SpN stimulation is able to modulate the response to an inflammatory stimulus, this could not be simply explained by a reduction in the inflammatory response. It has to be considered, however, that since most of the controls had to be euthanized within 30 minutes post LPS administration, further comparison of cytokine levels (at 1, 1.5 and 2 h post LPS) could not be performed between stimulated and sham animals. It is possible, therefore, that a difference in cytokine levels could have been observed in later time points, where TNFα and IL-6 reach their peak values.

Therefore, the data suggest that the pro-survival effect was due to the modulation of some other mechanisms.

Summary

In summary, the inventors found that neural stimulation of a nerve supplying the spleen, and in particular, the splenic arterial nerve, showed pro-survival effects in an in vivo LPS animal model. The inventors also found that electrical stimulation of the splenic arterial nerves stabilized blood pressure, which drops dramatically in LPS-treated animals, and reduced the maximum reduction in blood pressure. Hence, stimulation of the neural activity of splenic nerves can be particularly useful for treating acute medical conditions, such as life-threatening conditions having physiological changes associated with shock, and cardiovascular dysfunction (e.g. trauma, hemorrhaging and septic shock).

Study 4: Effects of Electrostimulation in In Vivo LPS Sub-Lethal Animal Model

Materials and Methods

Animals

A total of 8 female Large white pigs (60-70 Kg body weight) were used for this section of the study.

General Design

On the day of the study, one animal was sedated with ketamine/midazolam. Intravenous anesthesia was induced by administration of propofol (2 mg/Kg) via a catheter placed in an auricular (ear) vein. An endotracheal tube was then inserted into the trachea for the primary purpose of establishing and maintaining a patent airway and to maintain general anesthesia using sevoflurane carried in an oxygen/air mixture. After induction of general anesthesia, the animal was instrumented with invasive femoral artery and jugular vein catheters for monitoring blood pressure as well as providing fluids/drugs. Then the animal was positioned in right lateral recumbency. Palpebral reflex, corneal reflex, medioventral eye ball position, and jaw tone were used to monitor an aesthetic depth. Nystagmus as well as lacrimation were also monitored as possible signs of light plane of anesthesia. Electrocardiogram (ECG), Heart rate (HR), respiratory rate (RR), systemic arterial blood pressure (ABP), central venous pressure (CVP), pulse oximetry, capnography, spirometry and body temperature were monitored throughout the surgery. The animals were also instrumented with a continuous cardiac output measurement system (PICCO) as well as with a catheter into the pulmonary artery for cardiac output and pulmonary wedge pressure measurement. All physiological parameters as well as the fraction of inspired sevoflurane were also recorded (every 5 minutes) on the record sheet as well as continuously recorded via a Powerlab acquisition system and Labchart software. Animals were mechanically ventilated with positive-pressure for the duration of the procedure. The splenic artery and nerves were then accessed via a lateral laparotomy. A cuff was placed at the level of the proximal splenic artery to stimulate the splenic nerves. Stimulation was applied for 2 minutes at 10 Hz with a range of amplitudes. Sham animals did not receive any stimulation. Fifteen minutes after the end of the stimulation animals received an intravenous injection of 2.5 µg/kg endotoxin (Purified lipopolysaccharides from the cell membrane of *Escherichia coli* O111:B4; Sigma Aldrich), administered over a period of 5 minutes. This dose was chosen to cause significant cardiovascular effects without shock in the widow of 4-6 ours post LPS administration. About 30 minutes from the LPS injection a second stimulation (or sham stimulation) was delivered.

The stimulation parameters include a 1 minute duration, with square, biphasic, charge balanced symmetrical pulses at 10 Hz, with a 400 µs pulse duration (per phase) and a current amplitude corresponding to a charge density per phase between 40-90 µC/Cm$^2$.

Peripheral venous blood was collected immediately prior to LPS injection (baseline), and then every half hour up to 4 hours post injection. At the end of this time-window pigs were euthanized. For all of these time points, cytokine analysis (TNFα and IL-6), and routine haematology and biochemistry analyses (including lipases and amylases) were performed.

Cardiac Output was measured continuously with the PICCO system and also prior to LPS injection and at 30 min post LPS by using the pulmonary artery catheter in order to obtain Pulmonary capillary wedge pressure (PCWP).

Results

Stimulation Effects on Cardiovascular Parameters

Administration of LPS caused significant changes in ABP, CVP, HR and ET CO2. Interestingly animals subjected to splenic nerve electrical stimulation showed a lower magnitude change in ABP, CVP and HR (FIGS. 13A and B).

Figure 14A:
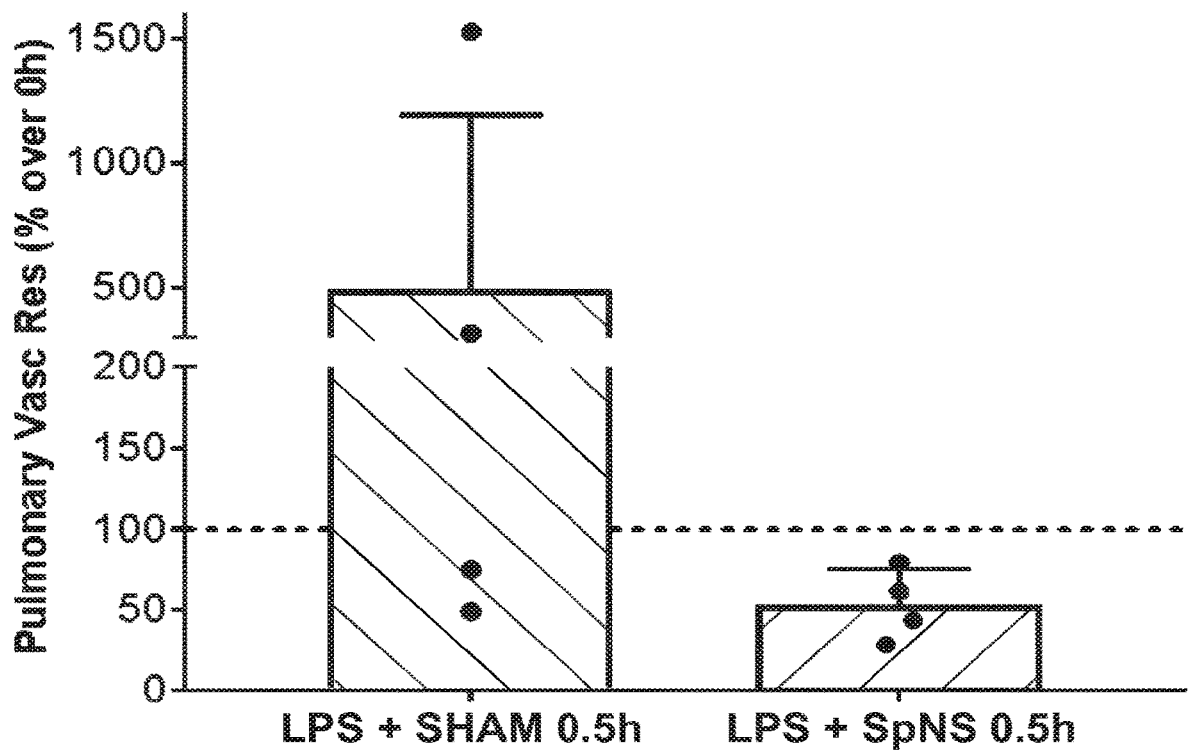
Figure 14B:
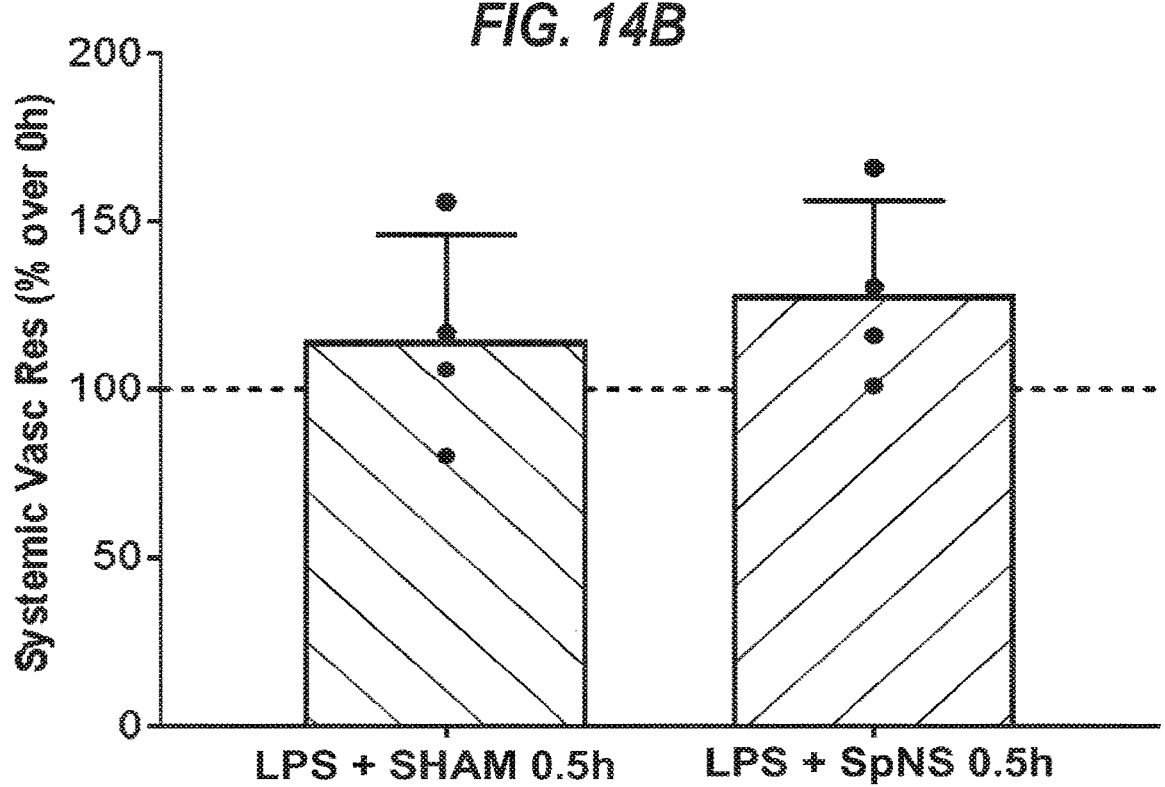

Injection of LPS also cause significant increase in the Pulmonary vascular resistance (PVR) at 30 minutes post-LPS injection. However, when animals were stimulated a stabilization and reduction of the PVR was observed (FIG. 14A). In paralleled the stimulation cause a slight stronger increase in systemic vascular resistance (SVR) as compared to sham animals (FIG. 14B) and a stronger increase in the PCWP (FIG. 14C).

Finally, LPS injection caused significant upregulation of circulating levels of Lipases. This increase was much smaller in splenic nerve stimulated animals (FIG. 15).

Discussion

Stimulation of the splenic nerve in pigs subjected to endotoxemia (sub-lethal dose of systemic LPS administration) caused a significant stabilization of the cardiovascular changes triggered by LPS. In particular the increased SVR and the reduced PVR might explain the positive output in the septic shock model described previously. This is paralleled by a smaller magnitude changes in CVP, ABP and HR following LPS administration as well as a reduction in the LPS-induced increase in lipases, thus indicating a lower level of organ damage and stronger protection compare to sham animals.

Human Data

Study 5: Electrophysiological Characterization of Human Splenic Nerves:

Materials and Methods

Human SpN Specimens

One fresh harvested tissue from a donor patient containing the splenic neurovascular bundle NVB was preserved in organ transplant-suitable solution on ice for transportation. Upon arrival the specimen was placed in ice-cold Kreb's solution under a dissecting microscope, and a minimum of one discrete SpN fascicle per sample was carefully separated from the SpA and subsequently instrumented with two bipolar circumferential cuff electrodes (0.65 mm diameter, 5.5 mm length; CorTec GmbH) placed approximately 10 mm apart, to evoke and record CAPs. Fascicle electrode coverage was estimated to be 100% in all implantations.

Recordings

Nerve activity was continuously monitored using an oscilloscope, and digitally recorded via a 1401 digital acquisition system and Spike2 software (Cambridge Electronic Design Ltd), with the sampling rate set at 20 kHz. Evoked CAPs were averaged (8 pulses) and the peak-to-peak amplitude of the averaged response quantified. The conduction velocity of the eCAP components was calculated from the measured distance between the stimulation site and the recording site and the latency of the eCAP signal (measured from the peak of the stimulation artefact to the peak of the eCAP).

Results

Figure 16B:
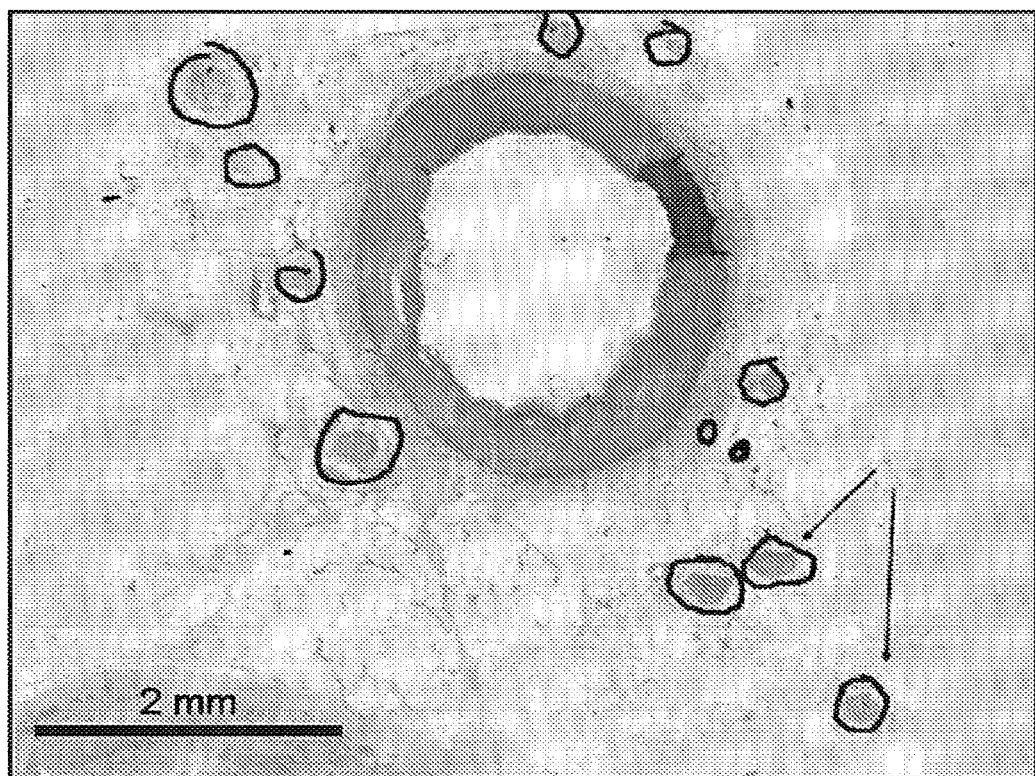
Figure 16C:
Figure 16D:
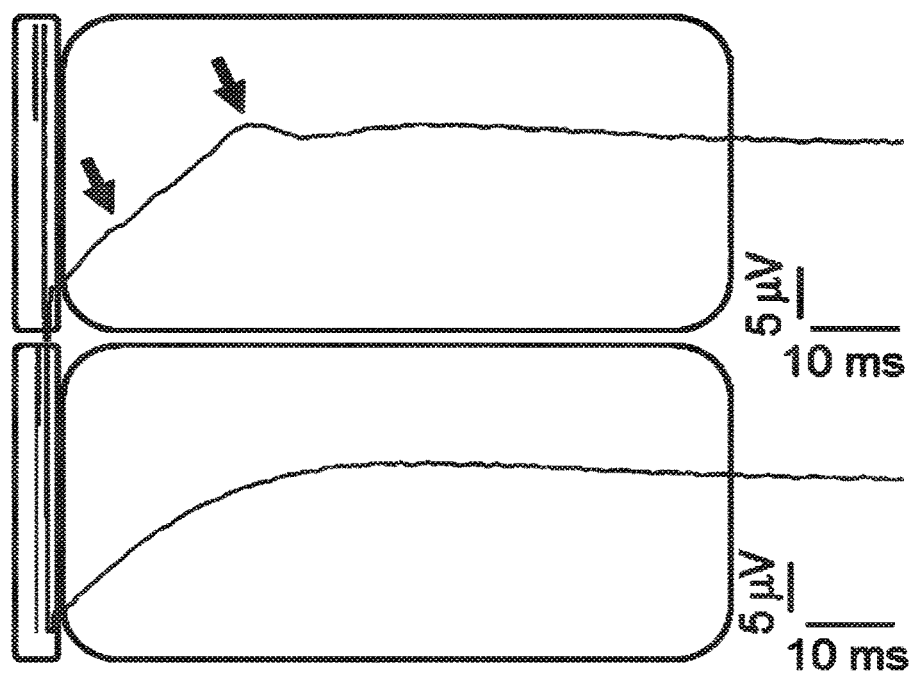
Figure 16E:
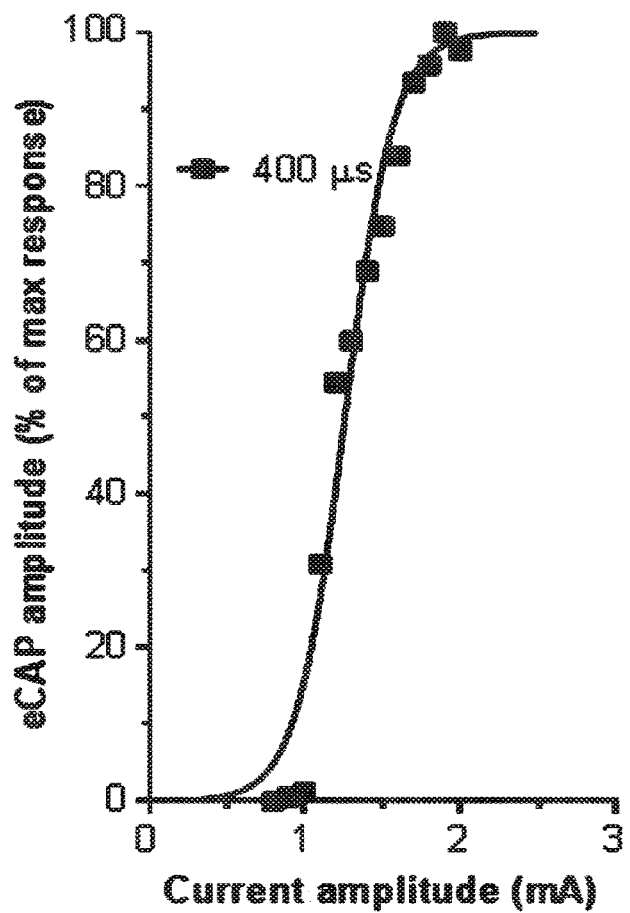

Compared to the porcine samples, the human SpA presented with a more convoluted course as previously described (Michels 1942). Furthermore, the splenic NVB was embedded in extensive amounts of connective tissue and fat (FIG. 16A), making recordings from the entire circumference of the structure challenging. However, using a dissecting microscope, several nerve fascicles were visible and later confirmed as such by histological sections of the specimens (FIG. 16B). After instrumenting some of these fascicles with stimulating and recording cuff electrodes (FIG. 16A, upper and lower image), stimulation generated clear eCAPs (FIG. 16D, upper trace). To confirm the validity of the recording at the end of the experiment the fascicles were crushed between the stimulating and recording electrodes and attempts to re-record were made (FIG. 16D, lower trace). Typical recruitment curves were obtained when applying stimulations at specific pulse durations (e.g. 100, 200, 400, 800 and 1000 µs; PW) and increasing amplitude (FIG. 16E).

Figure 16G:
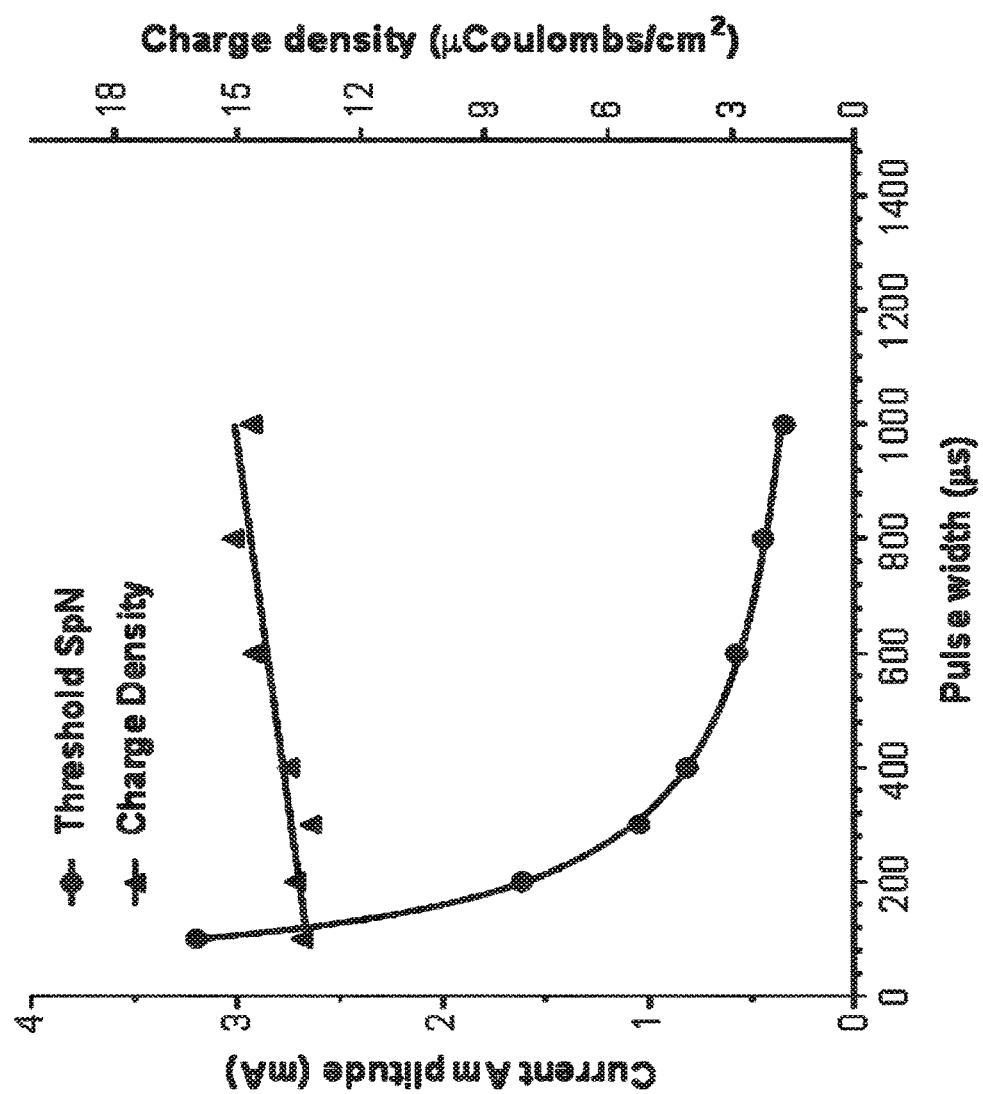
Figure 16F:
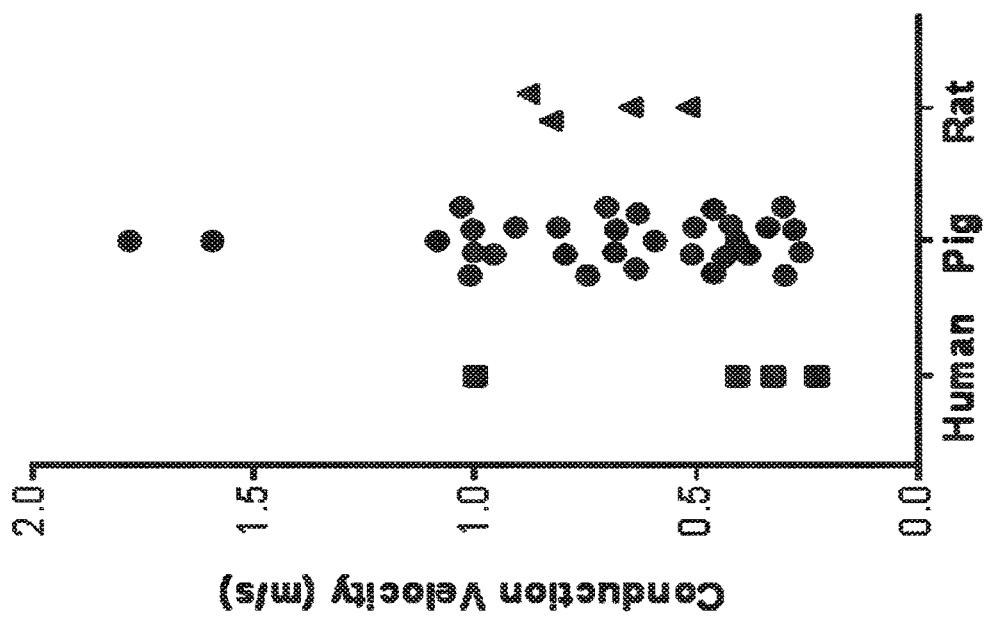
Figure 16H:
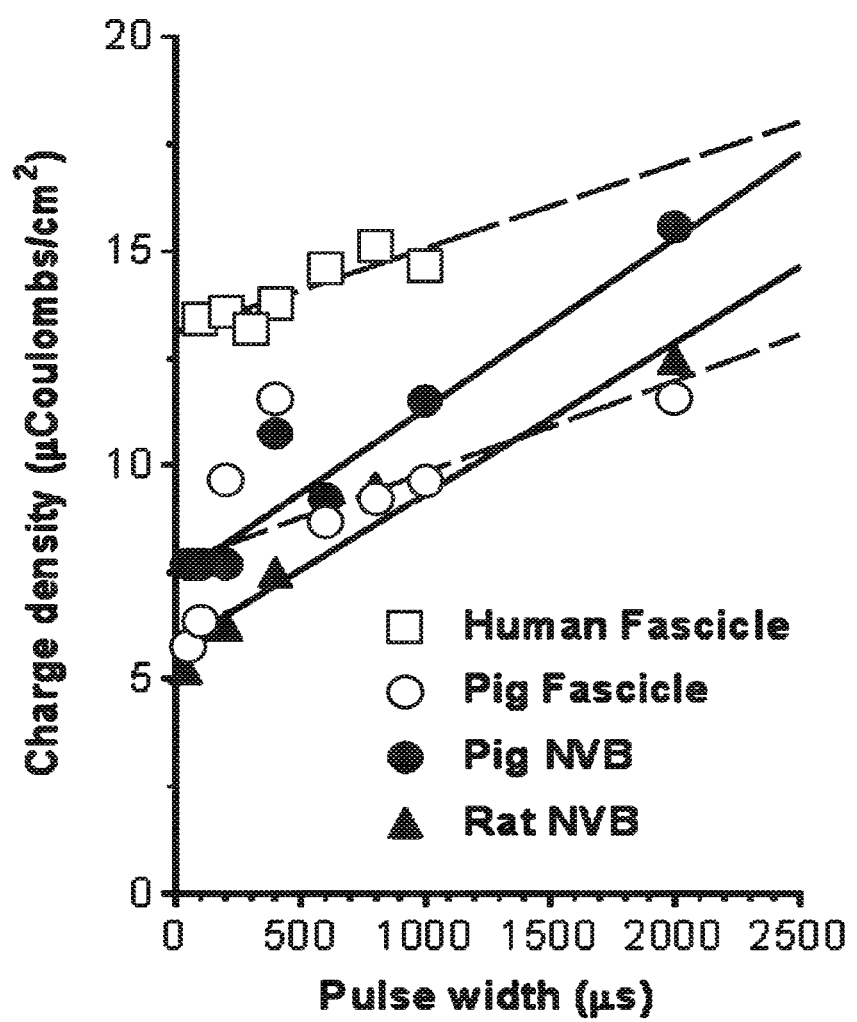
Figure 17A:
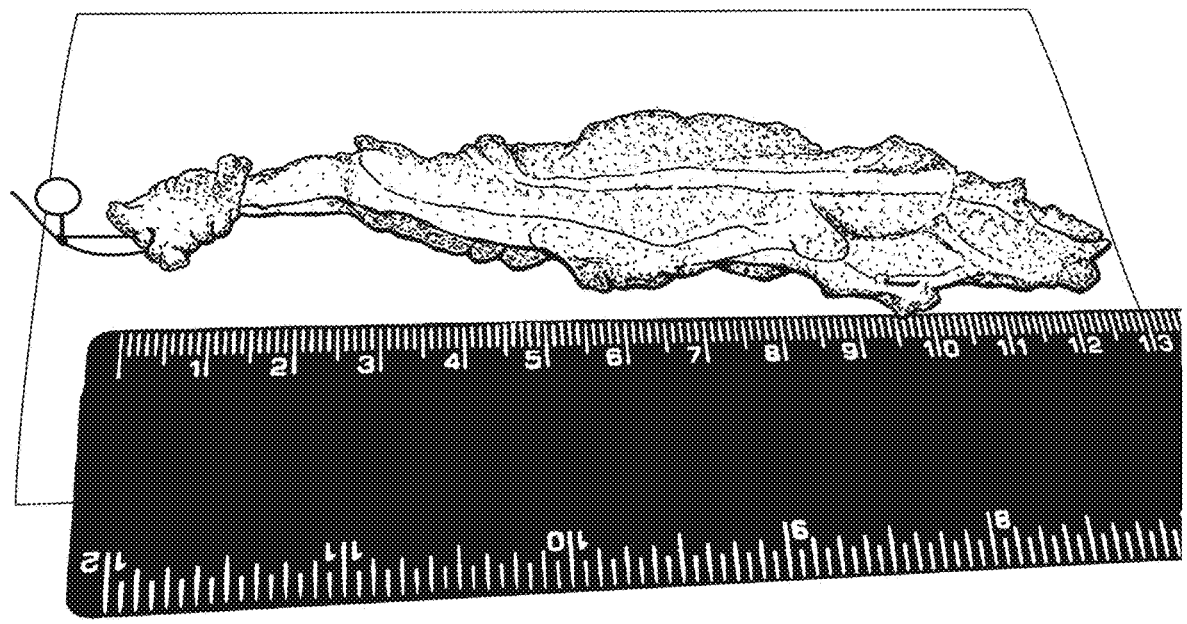
FIG. 17A shows an example of a human splenic sample with suture indicating the proximal end close to celiac.
Figure 17B:
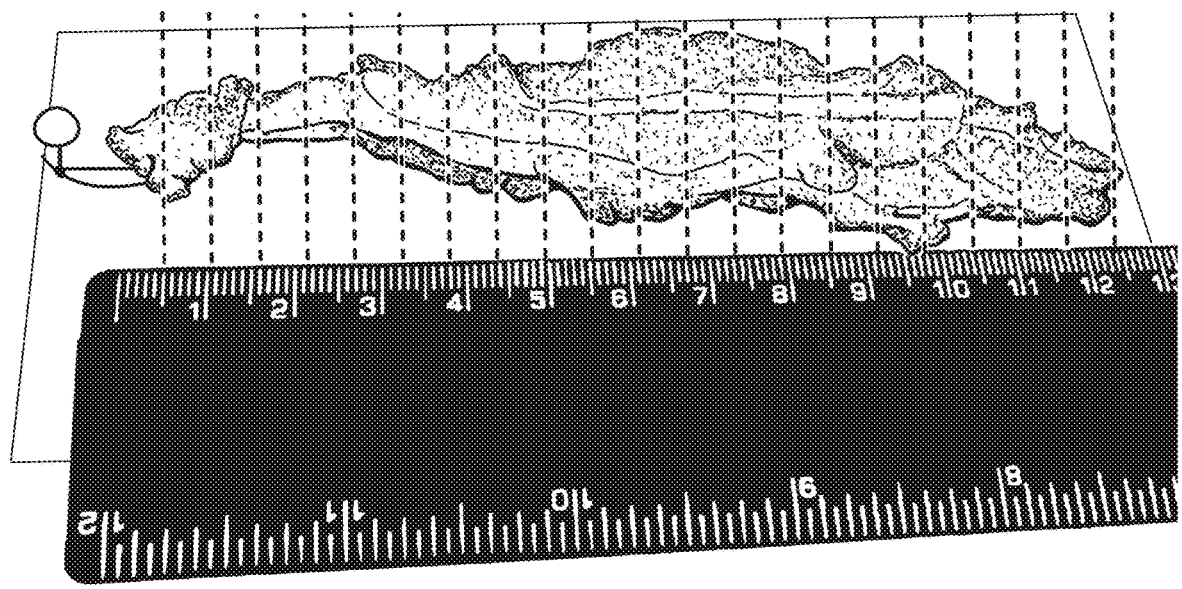
FIG. 17B shows a conceptual representation of slicing of tissue in blocks for histology.
Figure 17C:
FIG. 17C shows a Haematoxylin and Eosin (H&E) stained slide from one of the blocks.
Figure 17D:
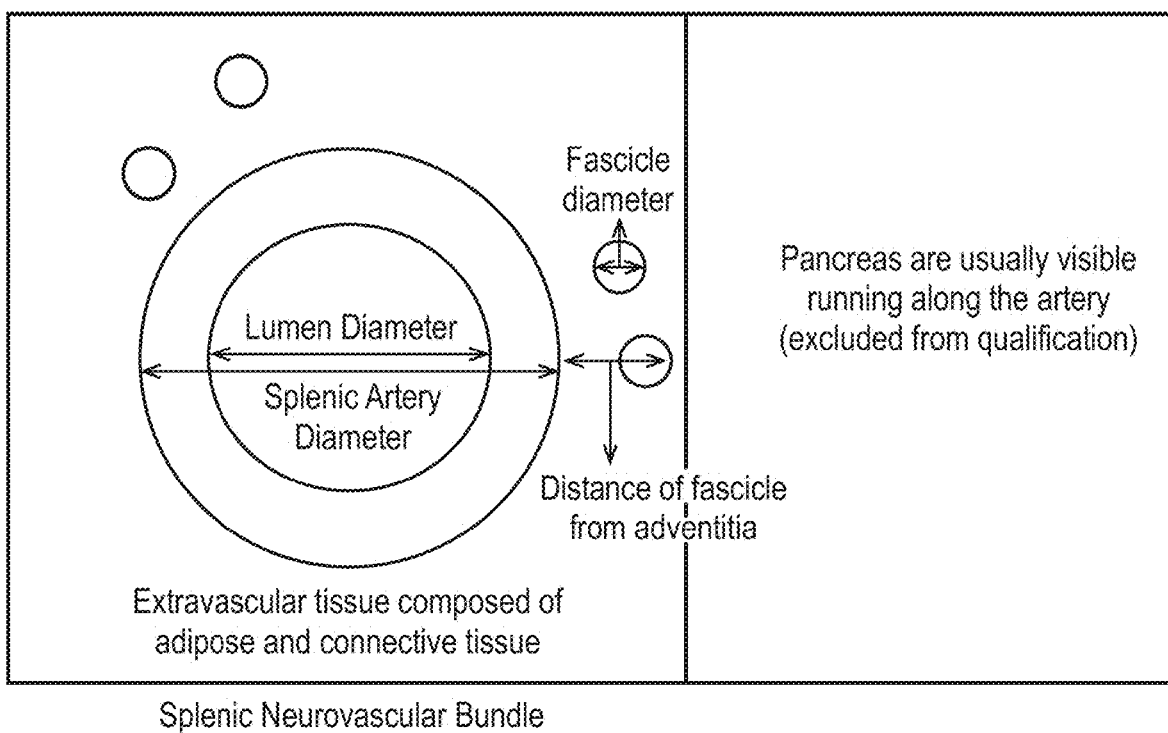
FIG. 17D shows methodology for histomorphometric estimations.

Calculated conduction velocities demonstrated typical values for unmyelinated fibres, where the range and average conduction velocity was 0.49 m/s, compared to porcine (0.7 m/s) and rat (0.72 m/s) SpN (FIG. 16F). In addition, the eCAP recordings of the human SpN showed a typical strength-duration relationship between current amplitude for nerve recruitment and pulse duration (FIG. 16G). Linear regression of the calculated charge density value for eCAP threshold recording showed slopes significantly different from zero (P=0.0084), with the lowest PW (100 μs) requiring 13.44 μC/cm$^2$, and the longest PW (2000 μs) requiring 14.7 μC/cm$^2$. Importantly, the slope in the charge density for the human SpN fascicles was found to be similar to the slope of the charge density for the porcine fascicles (FIG. 16H). In addition, the charge density requirement for nerve activation of the dissected human fascicles was about 1.5-2 times higher than the charge density required for activation of the porcine SpN fascicles at any PW (FIG. 16H).

tial blocks of 0.5 cm-1.5 cm for histology (see FIG. 17B). The tissue around the artery was retained for inclusion in the block. The sections were embedded and sectioned such that the same face of each block (i.e. proximal or distal to spleen) was sampled each time. The sections were usually 4-5 um thick and were stained with hematoxylin and eosin stain (H&E) (see FIG. 17C). Finally, a quality check of the tissue was performed by a pathologist and the glass slides were scanned at ×20. It should be noted that, as per literature, 10% of tissue shrinkage is accounted for. However, the artery diameter is representative of zero pressure. High amounts of adipose tissue was noted in all the samples received from transplant patients and the fascicles were found to be buried in a thick layer of adipose tissue.

TABLE 2

Estimated range for human splenic neurovascular bundle (~7 mm to 10 mm)

| Sample Number | Lumen Diameter | Lumen Wall + Arterial wall | Accounting for shrinkage of the tissue (+10%) | Range of extravascular tissue (based on middle splenic arterial loop) | Total NVB (*Does not account for pulsatile nature of the artery) |
|---|---|---|---|---|---|
| Sample 308B X91165 | 3.01 mm | 5.02 mm | 5.5 mm | 3.5 mm | 9 mm |
| Sample 359B X91252 | 3.92 mm | 5.2 mm | 5.72 mm | 2.4 mm | 8.12 mm |
| Sample 377C X91287 | 3.3 mm | 4.93 mm | 5.42 mm | 3.8 mm | 9.2 mm |
| Sample 380C X91291 | 2.76 mm | 4.72 mm | 5.192 mm | 4.9 mm | 10 mm |
| Sample 382B X91299 | 2.57 mm | 4 mm | 4.4 mm | 2.5 mm | 6.9 mm |

Discussion

The human SpN has anatomical, morphological and electrophysiological characteristics similar to other mammals (porcine and rodent). The human SpN are composed of unmyelinated axons as confirmed by conduction velocities. It is therefore appropriate to assume that the stimulation parameters (frequency and waveform) optimized in the pig will be also suitable for the human splenic nerve. However, requirements for charge need to be calculated from the entire NVB.

Study 6: Histomorphometric Characterization of Human Splenic Anatomy

The objective of this study was to develop an understanding of the human splenic anatomy and estimate the approximate values of splenic neurovascular bundle (NVB) using histology (see Table 2). The study was performed on the splenic tissue received from transplant patients. Histomorphometric estimations for lumen diameter, arterial wall, fascicle diameter (mean Feret diameter) and the approximate distance of each fascicle from adventitia (outer splenic arterial wall) were calculated.

Materials and Methods:

Five human splenic NVBs were provided from transplant patients at Addenbrooke's hospital, Cambridge, UK. The tissue was immersed in 10% neutral buffered formalin (NBF) as soon as possible post-excision. Photographs of the tissue were taken, with a ruler present for gross measurements (see FIG. 17A). The samples were divided in sequen- For quantification purposes, the splenic tissue was divided into three parts: proximal, middle and distal. Each of these parts consisted of several sections. The proximal end is close to the celiac indicated with a suture in FIG. 17A and distal is close to the spleen. Both of these are unlikely to be the intervention site for neural interface placement. The middle part with loops would be the likely intervention site.

Figure 18:
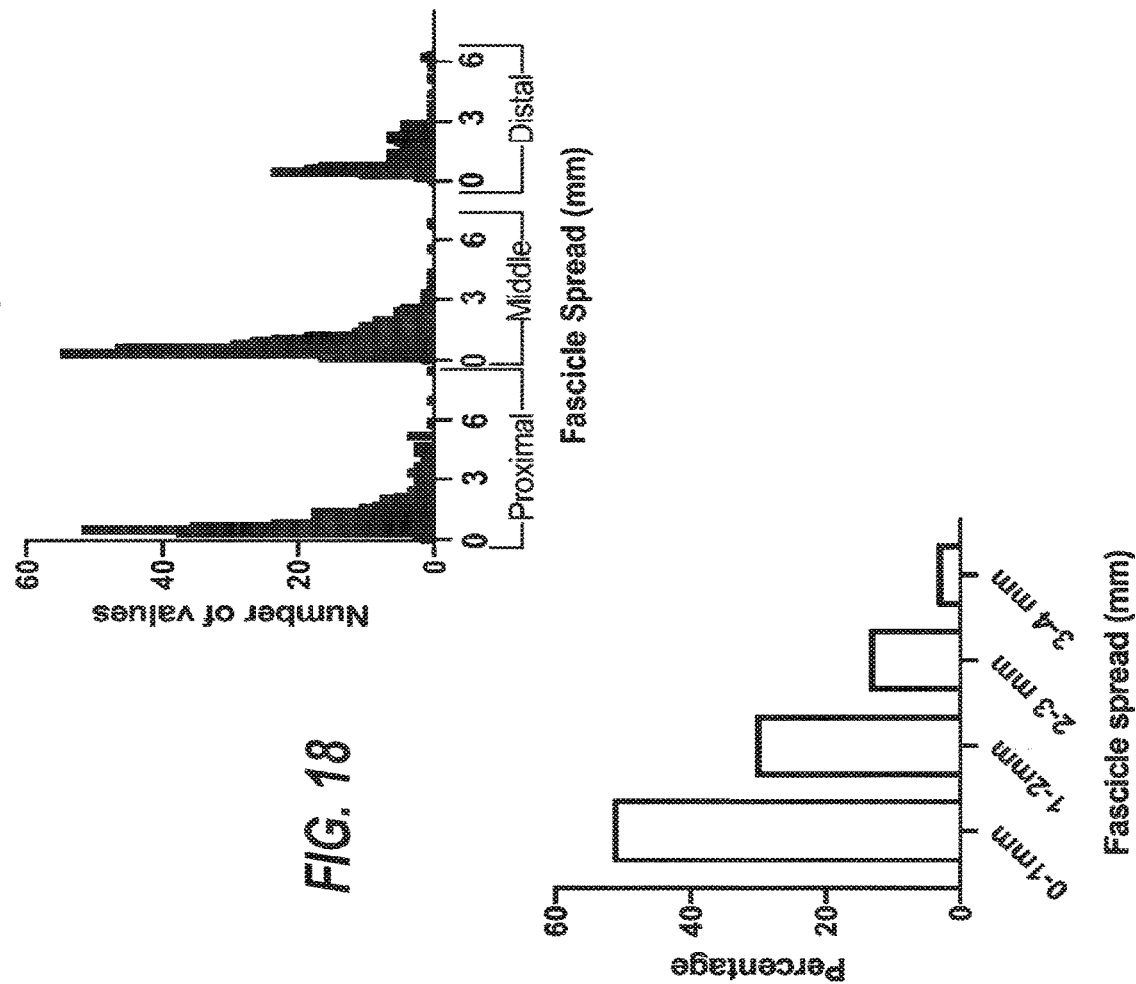
FIG. 18 shows (Left) Fascicle diameter, (Right) Fascicle spread around adventitia (outer splenic arterial wall) for proximal, middle and distal parts of the splenic neurovascular bundle (NVB), and (Middle) Percentage of fascicles vs distance from adventitia.

To summarize, as shown in FIG. 18, fascicle diameters are in the range of 20-400 um. For the fascicle spread approximately half of the nerve fibres were found in 0-1 mm region, 30% in 1-2 mm, 15% in 2-3 mm and the remaining in about 3-4 mm region.

Study 7: Translational Charge Requirements from Porcine to Human Splenic Neurovascular Bundle Materials and Methods:

3D Finite Element Model computer simulations were created using histology data from porcine and human splenic histology. This essentially comprised of splenic artery (lumen+arterial wall) and extravascular tissue. The 'extravascular tissue' is composed of 'adipose tissue' and 'connective tissue', with nerves embedded in the tissue. For porcines, a model with a split in the Cortec cuff (representing the in-vivo cuff) was used. For human models, cuffs with three arms structure were used. The diameter of the used cuff was 9 mm.

Considering the differences between porcine and human histology: the fascicles in porcine are evenly distributed around the artery and are in close proximity, whereas the fascicles in humans appear more dispersed; and b) the histology in porcine indicates negligible adipose tissue extravascularly, converse to substantial amounts in humans.

To translate the estimation of stimulation parameters from porcine to human, modeling was performed in the following two phases:

Phase (a): Development of 3D Finite Element Models (FEM) in Sim4Life simulation tool.

Sim4Life was used to develop representative nerve and artery models (based on histology and image quantification), cuff and electrodes (specifications defined by CAD) and 3D voltage fields.

Phase (b): Analysis of FEM solutions in the same tool. Sim4Life was used to interpolate voltage along axons using Sundt nerve model [19], and axon simulations estimated the strength-duration and population recruitment curves.

Results

Figure 19B:
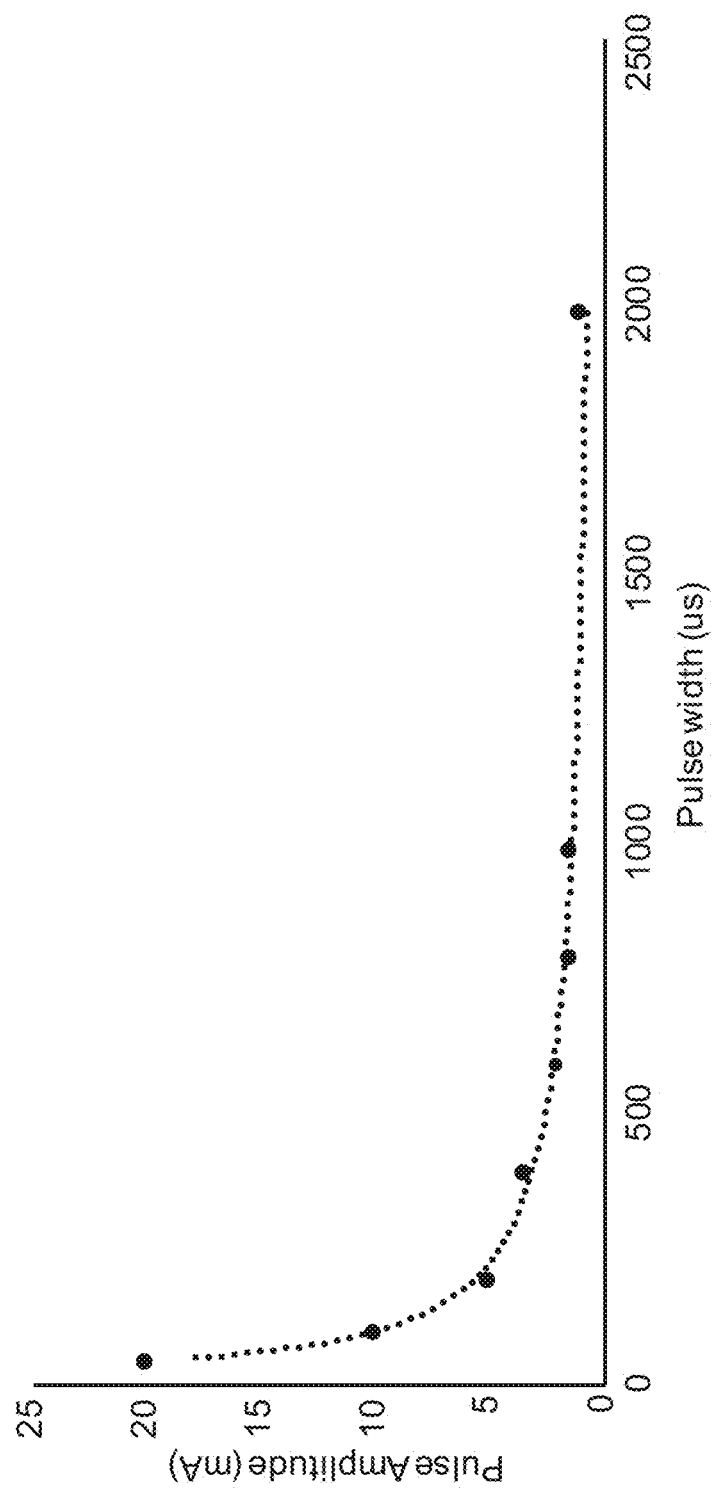
FIG. 19B shows a strength-duration curve for in-vivo data from porcine splenic neurovascular bundle simulation.
Figure 20A:
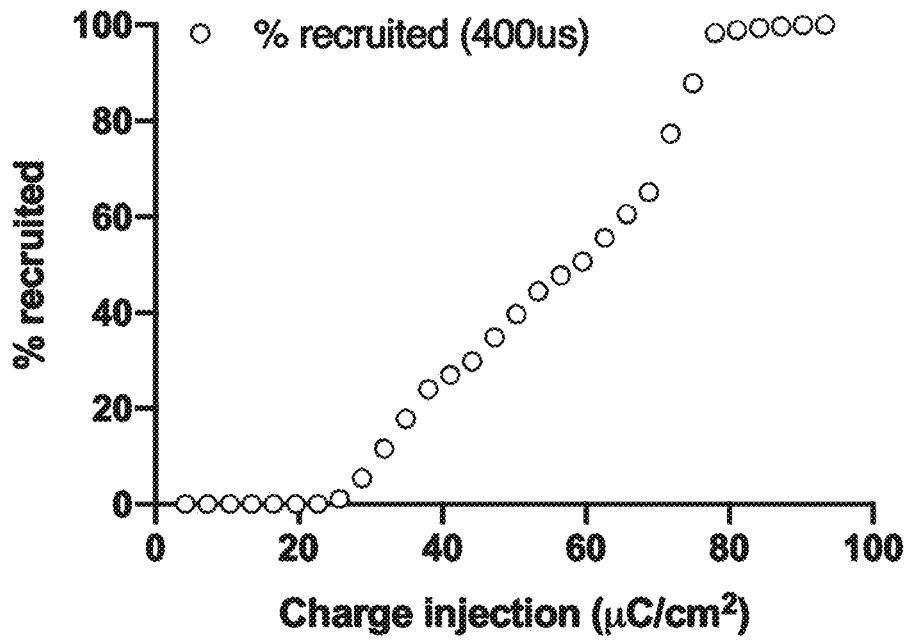
FIG. 20A shows a recruitment curve from in-silico modelling in porcines with x-axis representing charge injection estimates at 400 µs pulses.
Figure 20B:
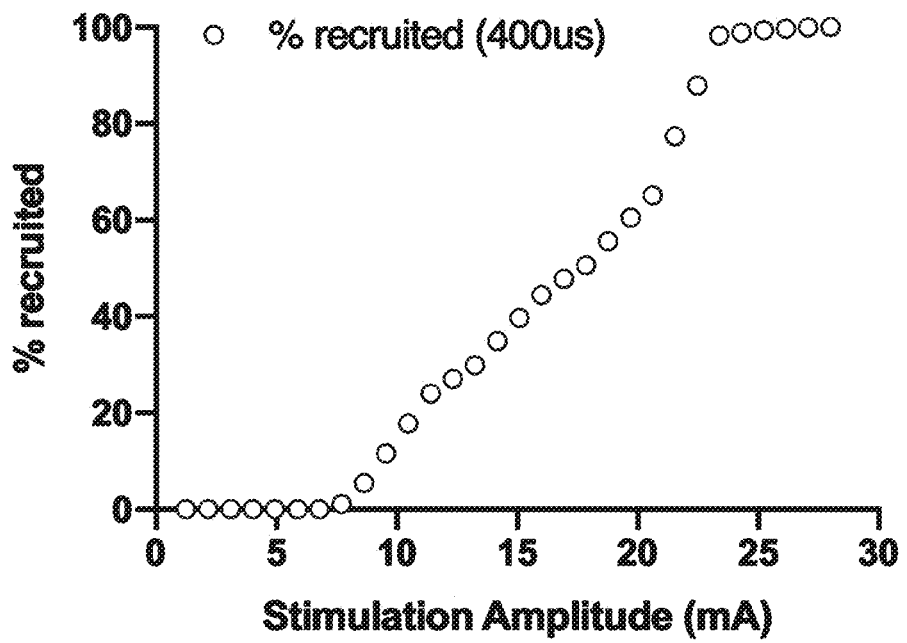
FIG. 20B shows the same but with x-axis reflecting stimulation amplitude.
Figure 20C:
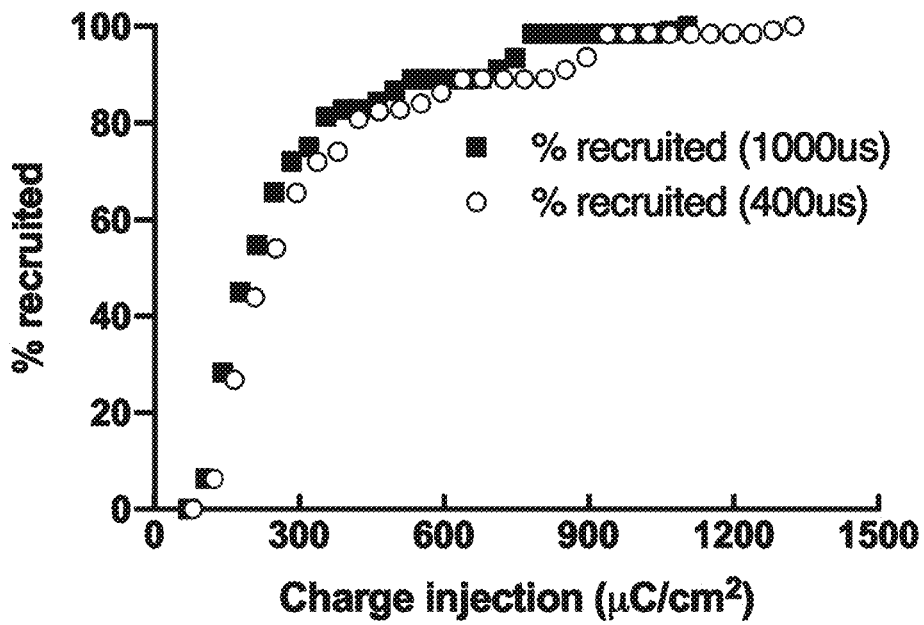
FIG. 20C shows a recruitment curve from in-silico modelling in humans with x-axis representing charge injection estimates at 400 µs (blue) and 1 ms pulses (red).
Figure 20D:
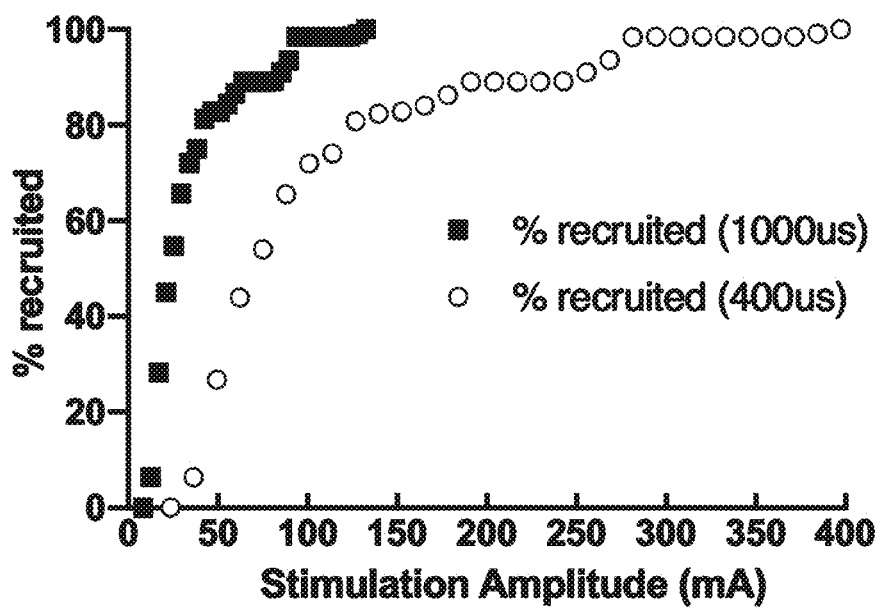
FIG. 20D shows the same but with x-axis reflecting stimulation amplitude (mA).

FIG. 19A represents the in-vivo acute data from porcine splenic neurovascular bundle from five animals. The range from five animals for charge requirements is estimated to be approximately 20-160 uC/cm$^2$ at <50 mA, 400 us and 10 Hz. For the third animal represented in grey the charge requirements are approximately 100 uC/cm$^2$ at 30 mA, 400 us and 10 Hz, which correlates well with the simulated data in-silico (see FIG. 20A). Using the correlation of in-silico vs in-vivo as a validation for the computational model in porcine, the charge requirements were translated to human splenic neurovascular bundle using histology sections for two pulse widths. The data is presented in FIGS. 20C-D and Table 3.

TABLE 3

Charge estimates for human models for two pulse widths i.e. 400 us and 1 ms pulses

| % recruited | Pulse Width | |
|---|---|---|
| | Charge estimates 400 us (µC/phase/cm$^2$) (Approx.) | Charge estimates 1000 us (µC/phase/cm$^2$) (Approx.) |
| Threshold | 79 | 70 |
| 10 | 130 | 110 |
| 30 | 170 | 150 |
| 50 | 225 | 200 |
| 80 | 422.8 | 335 |
| 80-100 | 450-1300 | 350-1100 |

It is estimated that the charge requirements in human acute models for a recruitment of 100% can potentially vary from approximately 80-1300 µC/cm$^2$ (using 400 uS pulse widths, 12 mm$^2$ surface area) and 70-1100 µC/cm$^2$ (using 1 ms pulse widths). Approximately 70% of the recruitment is indicated under 350 µC/cm$^2$. The additional 30% recruitment requires exponential increase in charge requirements beyond what is likely accommodated for by an implantable device. For example, it can be seen that a recruitment of 100% can potentially vary between 70-1300 µC/cm$^2$, between 70-450 µC/cm$^2$ for 80% recruitment, between 70-250 µC/cm$^2$ for 50% recruitment, and between 70-170 µC/cm$^2$ for 30% recruitment.

Discussion

The nerves fibres in the humans are more dispersed in comparison to porcines. The range of the fascicle spread around splenic artery as indicated by histology profiling can be in the range of approximately 1-3 mm. The histomorphomteric data was further used to optimise the stimulation parameters and translate the charge requirements from porcines to humans using computational modelling tools. Using Sundt c-fibre model the charge requirements for humans is indicated to be in range of approximately 70-1000 µC/cm$^2$ for hundred percent recruitment.

REFERENCES

[2] J. M. Huston et al., J Exp Med 203, 1623.
[2] R. Medzhitov, Nature 454, 428-435 (24 Jul. 2008).
[3] Greenway et al., J. Physiol. (1968), 194, 421-433.
[4] G. Vida, G. Pena, E. A. Deitch, L. Ulloa J Immunol 186, 4340.
[5] US 2006/0287678.
[6] US 2005/0075702.
[7] US 20050075701.
[8] F. Tischendorf F, Biol Lat 9:307-342, 1956.
[9] M. Fillenz, Proc R Soc Lond B Biol Sci 174:459-468, 1970.
[10] I. G. Zelenova, Arkh Anat Gistol Embriol 60:88-90, 1971.
[11] F. D. Reilly, Experientia 41:187-192, 1985.
[12] D. L. Felten et al., J Neurosci Res 18:28-36, 118-121, 1987.
[13] D. G. Onkar, J Morphol Sci 30: p. 16-20, 2013.
[14] D. Bakovic et al., Clin Exp Pharmacol Physiol 32:944-951, 2005.
[15] A. Lodin-Sundstrom, E. Schagatay, Aviat Space Environ Med 81:545-549, 2010.
[16] Schafer, E. A. and Moore, B., J Physiol., 1896.
[17] G. L. Brown, J. S. Gillespie J S, J Physiol, 138:81-102, 1957.
[18] A. G. Garcia, et al., J Physiol, 261:301-317, 1976.
[19] Sundt D, et al., Journal of neurophysiology. 114:3140-53, 2015.

The invention claimed is:

1. A system for stimulating neural activity of one or more nerves adjacent to a splenic arterial loop, for treating an acute medical condition, wherein the acute medical condition is trauma, shock, allograph/graph rejection, or an effect of a bacterial endotoxin, the system comprising:
    at least one electrode in signaling contact with the one or more nerves; and
    at least one controller electrically coupled to the at least one electrode, the at least one controller configured to control operation of the at least one electrode to apply an electrical signal to the one or more nerves,
    wherein the electrical signal has a waveform that comprises one or more pulse trains,
    wherein a charge density per phase applied to the one or more nerves by the electrical signal is ≥40 µC per cm$^2$ per phase and ≤1100 µC per cm$^2$ per phase,
    wherein the electrical signal produces an improvement in a physiological parameter indicative of treatment of the acute medical condition,
    wherein the improvement in the physiological parameter is any of the group consisting of: restoring a body temperature to between 36° C. and 38° C., restoring a heart rate to 60-100 bpm, restoring a systemic arterial pressure to between 90/60 mmHg and 150/90 mmHg, restoring a systemic venous pressure to 5 mmHg in a right atrium and 8 mmHg in a left atrium, restoring a pulmonary pressure to 15 mmHg, restoring a central venous pressure to in a range of 3 to 8 mmHg, restoring a breathing rate to 8-14 breaths per minute, an increase in oxygen saturation to ≥94%, an increase in an arterial partial pressure of oxygen to 12-15 kPa, restoring an arterial partial pressure of carbon dioxide to 4.4-6.1 kPa, a reduction of pain sensation, restoring urine output to ≥5 ml/kg/hr, a reduction in a level of lactate, a change in a level of blood glucose, a change in a level of base deficit in blood, a change in a level of arterial pH, lowering levels of pulmonary vascular resistance while increasing systemic vascular resistance and increasing pulmonary capillary wedge pressure, reducing levels of lipases, and reducing levels of amylases.

2. The system of claim 1, wherein the trauma is blunt trauma, penetrating trauma, blast injury or burns.

3. The system of claim 1, wherein the shock is anaphylactic shock, toxic shock syndrome, cardiogenic shock, hypovolemic shock, neurogenic shock, or endotoxic shock.

4. The system of claim 1, wherein the acute medical condition is the effect of a bacterial endotoxin.

5. The system of claim 1, further comprising a neural interface, the neural interface comprising the at least one electrode.

6. The system of claim 5, wherein the neural interface is configured to be placed around the splenic arterial loop.

7. The system of claim 5, wherein the neural interface is configured to be placed on the splenic arterial loop.

8. A method of reversibly stimulating neural activity of one or more nerves adjacent to a splenic arterial loop, the method comprising:
providing the system of claim 1;
positioning the at least one electrode in signaling contact with the one or more nerves; and
controlling the operation of the at least one electrode with the at least one controller to apply the electrical signal to the one or more nerves to stimulate the neural activity.

9. The method of claim 8, further comprising a neural interface, the neural interface comprising the at least one electrode.

10. The method of claim 9, wherein the neural interface is configured to be placed around the splenic arterial loop.

11. The method of claim 9, wherein the neural interface is configured to be placed on the splenic arterial loop.

12. A method for treating an acute medical condition, wherein the acute medical condition is trauma, shock, allograph/graph rejection, or an effect of a bacterial endotoxin, the method comprising applying an electrical signal with a waveform that comprises one or more pulse trains, to stimulate neural activity of one or more nerves adjacent to a splenic arterial loop, wherein a charge density per phase applied to the one or more nerves by the electrical signal is ≥40 μC per cm$^2$ per phase and ≤1100 μC per cm$^2$ per phase, such that the electrical signal produces an improvement in a physiological parameter indicative of treatment of an acute medical condition, wherein the improvement in the physiological parameter is any of the group consisting of: restoring a body temperature to between 36° C. and 38° C., restoring a heart rate to 60-100 bpm, restoring a systemic arterial pressure to between 90/60 mmHg and 150/90 mmHg, restoring a systemic venous pressure to 5 mmHg in a right atrium and 8 mmHg in a left atrium, restoring a central venous pressure to in a range of 3-8 mmHg, restoring a pulmonary pressure to 15 mmHg, restoring a breathing rate to 8-14 breaths per minute, an increase in oxygen saturation to 94%, an increase in an arterial partial pressure of oxygen to 12-15 kPa, restoring an arterial partial pressure of carbon dioxide to 4.4-6.1 kPa, a reduction of pain sensation, restoring urine output to 115 ml/kg/hr, a reduction in a level of lactate, a change in a level of blood glucose, a change in a level of base deficit in blood, a change in a level of arterial pH, lowering levels of pulmonary vascular resistance while increasing systemic vascular resistance and increasing pulmonary capillary wedge pressure, reducing levels of lipases, and reducing levels of amylases.

13. The method of claim 12, wherein the trauma is blunt trauma, penetrating trauma, blast injury or burns.

14. The method of claim 12, wherein the shock is anaphylactic shock, toxic shock syndrome, cardiogenic shock, hypovolemic shock, neurogenic shock, or endotoxic shock.

15. The method of claim 12, wherein the acute medical condition is the effect of a bacterial endotoxin.

16. The method of claim 12, wherein the acute medical condition is the allograph/graph rejection.

* * * * *